US010274481B2

(12) United States Patent
Radtke et al.

(10) Patent No.: US 10,274,481 B2
(45) Date of Patent: Apr. 30, 2019

(54) METHOD FOR IDENTIFYING MODULATORS OF NOTCH SIGNALING

(71) Applicant: ECOLE POLYTECHNIQUE FEDERALE DE LAUSANNE (EPFL), Lausanne (CH)

(72) Inventors: Freddy Radtke, Epalinges (CH); Rajwinder Lehal, Lausanne (CH); Viktoria Reinmüller, Lausanne (CH); Jieping Zhu, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/017,986

(22) Filed: Feb. 8, 2016

(65) Prior Publication Data
US 2016/0266095 A1  Sep. 15, 2016

Related U.S. Application Data

(63) Continuation of application No. 14/366,917, filed as application No. PCT/IB2012/057622 on Dec. 21, 2012, now Pat. No. 9,296,682.

(30) Foreign Application Priority Data

Dec. 21, 2011 (EP) ..................... 11010130

(51) Int. Cl.
| C07K 14/705 | (2006.01) |
| C07K 16/18 | (2006.01) |
| C07K 16/28 | (2006.01) |
| C12N 15/63 | (2006.01) |
| C12Q 1/68 | (2018.01) |
| C12Q 1/6897 | (2018.01) |
| G01N 33/53 | (2006.01) |
| G01N 33/533 | (2006.01) |
| G01N 33/574 | (2006.01) |
| G01N 33/50 | (2006.01) |
| G01N 33/68 | (2006.01) |
| C12N 15/09 | (2006.01) |
| A61K 31/351 | (2006.01) |
| A61K 31/407 | (2006.01) |
| A61K 31/44 | (2006.01) |
| A61K 31/09 | (2006.01) |
| A61K 45/06 | (2006.01) |
| A61N 5/10 | (2006.01) |
| C07C 205/38 | (2006.01) |
| C07C 217/90 | (2006.01) |
| C07D 213/64 | (2006.01) |
| C07D 213/73 | (2006.01) |
| A61P 35/00 | (2006.01) |

(52) U.S. Cl.
CPC .......... *G01N 33/5011* (2013.01); *A61K 31/09* (2013.01); *A61K 31/351* (2013.01); *A61K 31/407* (2013.01); *A61K 31/44* (2013.01); *A61K 45/06* (2013.01); *A61N 5/10* (2013.01); *A61P 35/00* (2018.01); *C07C 205/38* (2013.01); *C07C 217/90* (2013.01); *C07D 213/64* (2013.01); *C07D 213/73* (2013.01); *C12N 15/09* (2013.01); *C12N 15/63* (2013.01); *C12Q 1/6897* (2013.01); *G01N 33/53* (2013.01); *G01N 33/57492* (2013.01); *G01N 33/57496* (2013.01); *G01N 33/6872* (2013.01); *C07K 14/705* (2013.01); *C07K 16/18* (2013.01); *C07K 16/28* (2013.01); *C12N 2501/42* (2013.01); *G01N 2333/4703* (2013.01); *G01N 2333/705* (2013.01); *G01N 2333/75* (2013.01)

(58) Field of Classification Search
CPC ...... C07K 16/28; C07K 16/18; C07K 14/705; G01N 2333/705; G01N 33/53; G01N 33/6872; G01N 33/57492; G01N 33/57496; C12N 2501/42; C12N 15/63; C12N 15/09

See application file for complete search history.

(56) References Cited

U.S. PATENT DOCUMENTS

| 4,816,373 A | 3/1989 | Ohashi et al. |
| 6,692,919 B1* | 2/2004 | Artavanis-Tsakonas ..................... C07K 14/705 435/7.1 |
| 10,054,581 B1 | 8/2018 | Radtke et al. |
| 2006/0002924 A1* | 1/2006 | Bodmer ................. C07K 14/47 424/143.1 |
| 2009/0081238 A1* | 3/2009 | Siebel ................ A61K 39/3955 424/172.1 |

(Continued)

FOREIGN PATENT DOCUMENTS

| JP | 2001-089412 | 4/2001 |
| WO | 93/25225 | 12/1993 |
| WO | 00/42012 | 7/2000 |

(Continued)

OTHER PUBLICATIONS

Artavanis-Tsakonas et al. Notch signaling: cell fate control and signal integration in development. Science 284(5415): 770-776, 1999.*

(Continued)

*Primary Examiner* — Bridget E Bunner
(74) *Attorney, Agent, or Firm* — Wenderoth, Lind & Ponack, L.L.P.

(57) ABSTRACT

The present invention relates to use of inhibitors of Notch signalling pathway selected from the group consisting of 6-(4-Tert-Butylphenoxy)Pyridin-3-Amine (I3), its derivatives, in treating and/or preventing cancers.

25 Claims, 5 Drawing Sheets

(56) References Cited

U.S. PATENT DOCUMENTS

2010/0234463 A1* 9/2010 Churcher ............... C12Q 1/37
514/570
2010/0292193 A1 11/2010 McBride et al.

FOREIGN PATENT DOCUMENTS

| WO | 2003/051825 | 6/2003 |
| WO | 2009/146875 | 12/2009 |
| WO | 2010/033655 | 3/2010 |

OTHER PUBLICATIONS

Bray, S.J. Notch signalling: a simple pathway becomes complex. Nature Rev (Molec Cell Biol) 7: 678-689, 2006.*

Emuss et al. KSHV manipulates Notch signaling by DLL4 and JAG1 to alter cell cycle genes in lymphatic endothelia. PLoS Pathog 5(10): e1000616, 2009 (12 total pages).*

Jaleco et al. Differential effects of Notch ligands Delta-1 and Jagged-1 in human lymphoid differentiation. J Exp Med 194(7): 991-1001, 2001.*

Kavian et al. New insights into the mechanism of Notch signalling in fibrosis. Open Rheumatol J 6(Suppl 1: M5): 96-102, 2012.*

Miele, L. Transcription factor RBPJ/CSL: A genome-wide look at transcriptional regulation. Proc Natl Acad Sci USA 108(39): 14715-14716, 2011.*

Oberbek et al. Generation of stable, high-producing CHO cell lines by lentiviral vector-mediated gene transfer in serum-free suspension culture. Biotechnol Bioeng 108: 600-610, 2011.*

Schroeter et al. Notch-1 signalling requires ligand-induced proteolytic release of intracellular domain. Nature 393: 382-386, 1998.*

European Patent Office, International Search Report and Written Opinion of the International Searching Authority dated Apr. 26, 2013, issued in corresponding International Application No. PCT/IB2012/057622.

3-Pyridinamine, 6-[3-(1,1-dimethylethyl)phenoxy]-, Feb. 1, 2009, CAS Registry No. 1098366-43-8 (3 pages).

3-Pyridinamine, 6-[4-(1,1-dimethylpropyl)phenoxy]-, Jul. 27, 2008, CAS Registry No. 1036533-91-1 (3 pages).

Benzenamine, 4-[4-(1,1-dimethylethyl)phenoxy]-3-fluoro-, Sep. 12, 2007, CAS Registry No. 946785-77-9 (3 pages).

Benzenamine, 4-[4-(1,1-dimethylpropyl)phenoxy]-3-fluoro-, Sep. 12, 2007, CAS Registry No. 946742-50-3 (3 pages).

Official Action dated Mar. 3, 2015 in U.S. Appl. No. 14/366,917.

Sabrina G. Desbordes et al., "High-Throughput Screening Assay for the Identification of Compounds Regulating Self-Renewal and Differentation in Human Embryonic Stem Cells", Cell Stem Cell. Jun. 5, 2008; 2(6): 602-612.

Harris L. Friedman et al., "Tuberculostatic Compounds. I. Ethers of 2-Hydroxy-5-aminopyridine", J. Amer. Chem Soc., 1947, vol. 69, pp. 1204-1206.

Extended European Search Report dated Jun. 6, 2012 in European Application No. 11010130.0.

Written Opinion of International Search Authority dated Jun. 21, 2014 in International Application No. PCT/IB2012/057622.

Neehar Bhatia et al., Identification of novel small molecules that inhibit protein-protein interactions between MAGE and KAP-1:, Arch Biochem Biophys., 2011, vol. 508, No. 2, pp. 217-221.

Leonor M. Sarmento et al., "Therapeutic potential of Notch inhibition in T-cell acute lymphoblastic leukemia: rationale, caveats and promises", Expert Review of Anticancer Therapy, 2011, vol. 11, No. 9, pp. 1403-1415.

Sheng-Huei Hsiao et al., "Electroactive aromatic polyamides and polyimides with adamantylphenoxy-substituted triphenylamine units", European Polymer Journal, vol. 45, Issue 8, 2009, pp. 2234-2248.

* cited by examiner

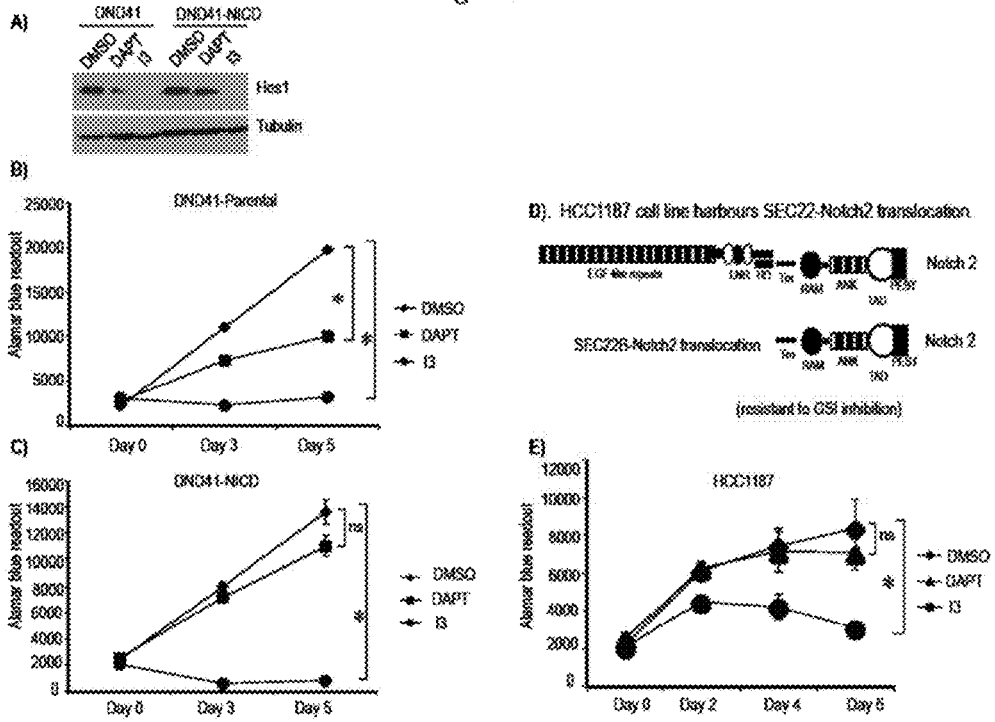
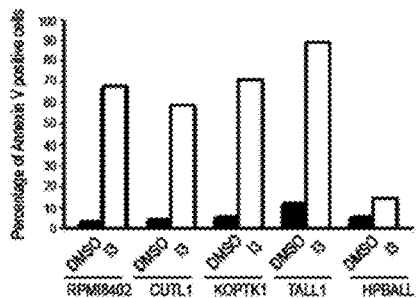
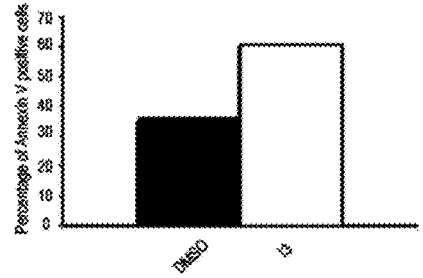

METHOD FOR IDENTIFYING MODULATORS OF NOTCH SIGNALING

FIELD OF THE INVENTION

The present invention relates to the use of inhibitors of Notch signalling pathway in particular 6-(4-Tert-Butylphenoxy)Pyridin-3-Amine (I3) (CAS number 218457-67-1) and its derivatives, in the treatment and/or prevention of cancers.

BACKGROUND OF THE INVENTION

The Notch signalling pathway represents a critical component in the molecular circuits that control cell fate during development, cell survival and cell proliferation (Shih IeM, Wang T L in Cancer Res 2007; 67(5):1879-82). Aberrant activation of this pathway contributes to tumorigenesis. The Notch family members are being revealed as oncogenes in an ever-increasing number of cancers. The role of Notch in human cancer has been highlighted recently by the presence of activating mutations and amplification of Notch genes in human cancer and by the demonstration that genes in the Notch signalling pathway could be potential therapeutic targets. It has become clear that one of the major therapeutic targets in the Notch pathway are the Notch receptors, in which γ-secretase inhibitors prevent the generation of the oncogenic (intracellular) domain of Notch molecules and suppress the Notch activity.

Though significant progress has been made in dissecting the complex workings of this signalling pathway, there are very limited options available for Notch inhibitors. However, the pioneering class of Notch inhibitors is already in clinical trials for few cancer types, such as γ-secretase inhibitors MK0752 of Merck Sharp & Dohme Corp. MK0752, and RO4929097 (Roche), a synthetic small molecule, inhibits the Notch signalling pathway, which may result in induction of growth arrest and apoptosis in tumor cells in which the Notch signalling pathway is overactivated.

One of the drawbacks of use of γ-secretase inhibitors to block Notch signaling, as currently on the market or under investigation, is their wide range of additional targets such as amyloid precursor protein as well as non-selectivity in blocking Notch signalling via all four ligands (Notch1, 2, 3 and 4). Due to their ability to block Notch signalling via all four receptors γ-secretase inhibitors are known to cause goblet cell metaplasia in the intestine. In addition, some of the hematological malignancies and solid tumors harbor mutations in the Notch receptors (such as chromosomal translocations) resulting in constitutive expression of dominant active form of NICD independent of cleavage by γ-secretase complex. Therefore these tumors fail to respond to γ-secretase inhibitors treatment.

Therefore, there is still a need to identify and develop further specific and selective inhibitors of Notch signalling pathway useful for treating and/or preventing cancers.

SUMMARY OF THE INVENTION

The present invention concerns an 6-(4-Tert-Butylphenoxy)Pyridin-3-Amine (I3) of Formula I

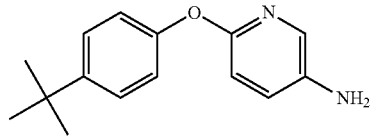

Formula I or one of its derivatives having Notch signalling pathway inhibition properties, salts, solvates, tautomers, isomers thereof for use in the treatment and/or prevention of a cancer.

A further object of the present invention is to provide a pharmaceutical composition comprising pharmaceutical composition comprising 6-(4-Tert-Butylphenoxy)Pyridin-3-Amine (I3) of Formula I, or one of its derivatives having Notch signalling pathway inhibition properties, or pharmaceutically acceptable salts, solvates, tautomers, isomers thereof, and a pharmaceutically acceptable carrier.

The invention also contemplates a kit comprising one or more doses of 6-(4-Tert-Butylphenoxy)Pyridin-3-Amine (I3), or one of its derivatives having Notch signalling pathway inhibition properties, for use in a method for treatment and/or prevention of cancer, optionally with reagents and/or instructions for use.

A further object of the invention is to provide the use of 6-(4-Tert-Butylphenoxy)Pyridin-3-Amine (I3) of Formula I or one of its derivatives having Notch signalling pathway inhibition properties, for inhibiting in vitro or in vitro the Notch signalling pathway in cells.

Another object of the invention is to provide a method of treating a subject for Notch dependent cancer.

DESCRIPTION OF THE FIGURES

FIG. 5 shows 6-(4-Tert-Butylphenoxy)Pyridin-3-Amine (I3) blocks NICD dependent growth of human cancer cells. A) DND41-Parental and DND41-NICD cells were treated with 6-(4-Tert-Butylphenoxy)Pyridin-3-Amine (I3) and DAPT for 24 hours. Western blot analyses were carried out for Hes1 protein using Hes1 specific antibodies. Both DAPT and 6-(4-Tert-Butylphenoxy)Pyridin-3-Amine (I3) caused a downregulation of Hes1 in DND41-Parental cells. DND41-NICD cells showed a downregulation of Hes1 only when treated with 6-(4-Tert-Butylphenoxy)Pyridin-3-Amine (I3). B) Five thousand DND41-Parental cells were seeded and treated with DMSO, 6-(4-Tert-Butylphenoxy)Pyridin-3-Amine (I3) and DAPT in a 96 well plate. Growth kinetics of the parental cell line was followed over 5 days using Alamar blue readout. Treatment of DND41-Parental cell line with both 6-(4-Tert-Butylphenoxy)Pyridin-3-Amine (I3) and DAPT caused a proliferation arrest. C) Similarly, DND41-NICD cells treated with DMSO, 6-(4-Tert-Butylphenoxy)Pyridin-3-Amine (I3) and DAPT and their growth kinetics were monitored using Alamar blue readout over 5 days. The treatment of DND41-NICD cells with DAPT did not have a significant impact on their proliferation, while 6-(4-Tert-Butylphenoxy)Pyridin-3-Amine (I3) treatment induced a proliferation arrest. D) Human breast cancer cell line HCC1187 harbors a SEC22B-Notch2 chromosomal translocation, thus leading to an expression of constitutively active form of NICD independent of cleavage by the γ-secretase complex. This mutation renders this cell line insensitive to γ-secretase inhibitor treatment. E) Two thousand HCC1187 cells were seeded per well in a 96 well plate. The cells were treated with DMSO, γ-secretase inhibitor DAPT and I3 for 6 days. Alamar blue readout was taken at day 0, day 2, day 4 and day 6. Eight replicates were used for each treatment and time point. The treatment of HCC1187 human breast cancer cell line with γ-secretase inhibitor DAPT did not alter the growth kinetics when compared to DMSO treated counterparts, while I3 treatment caused statistically significant inhibition of cell proliferation. P values were calculated using Student's t.test. *=p value<0.05. ns=not significant.

FIG. 6 shows 6-(4-Tert-Butylphenoxy)Pyridin-3-Amine (I3) induces G0/G1 cell cycle arrest and apoptosis in human T cell acute lymphoblastic leukemia cell lines and human breast cancer cell line HCC1187. A) Human leukemic cell lines (RPMI8402, CUTL1, KOPTK1, TALL1 and HPBALL) were treated with I3 (10 μM). Percentage of Annexin V positive (apoptotic) cell population was measured using flow cytometry. B) Cell cycle analyses: RPMI8402, KOPTK1 and TALL1 cell lines were treated with I3 (10 μM) and stained with Ki67 and Hoechst stain to determine cell cycle status. The cell cycle analyses suggest that I3 treatment causes 20-30% increase in cells arrested in G0/G1 phase of the cell cycle. C) HCC1187 cells were treated with DMSO or 10 μM of I3 and percentage of apoptotic population was measured using Annexin V stain. D) I3 treated HCC1187 cells analyzed for cell cycle status. Ki67 and Hoechst stain revealed that I3 induces G0/G1 arrest in HCC1187 cells.

SCID γc$^{-/-}$ mice were transplanted with 5×10$^5$ RPMI 8402 (luciferase expressing) cells. Leukemia development was followed using Caliper IVIS (Xenogen) live imaging system. On day 13, a daily treatment was started using oil (n=3) or 6-(4-Tert-Butylphenoxy)Pyridin-3-Amine (I3) (n=4). Animals were treated for 27 days (end point of the experiment).

Figure 9:
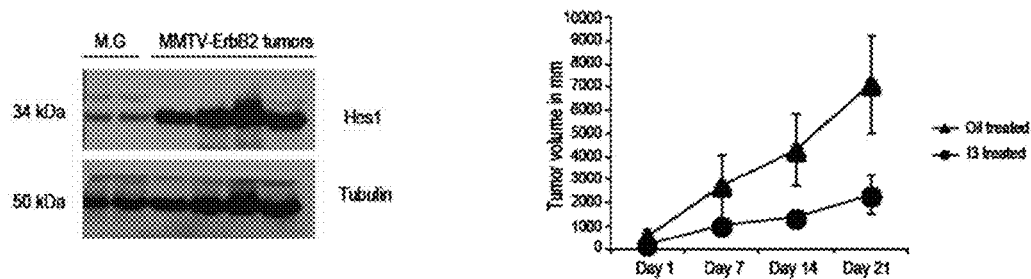

FIG. 9 shows 6-(4-Tert-Butylphenoxy)Pyridin-3-Amine (I3) treatment blocks MMTV-ErbB2 mouse mammary tumors. A) Hes1 protein expression levels in MMTV-ErbB2 mammary tumors and normal age matched mammary glands (M.G) were compared using Anti-Hes1 antibody. Western blot analyses showed a very high expression of Hes1 protein in MMTV-ErbB2 mammary tumors. Tubulin served as a loading control. B) A single cell suspension of MMTV-ErbB2 mammary tumor was prepared and 1×10$^6$ cells were injected into the cleared fat pad of recipient FVB mice. Tumor formation was monitored on a regular basis. Once the tumor developed to a volume of 100-300 mm$^3$, mice were treated with oil (n=2) or 25 mg/kg of 6-(4-Tert-Butylphenoxy)Pyridin-3-Amine (I3) (n=2). Tumor volume was measured every 6-7 days. Mice treated with 6-(4-Tert-Butylphenoxy)Pyridin-3-Amine (I3) exhibited a slow tumor progression compared to oil treated mice.

Figure 10:
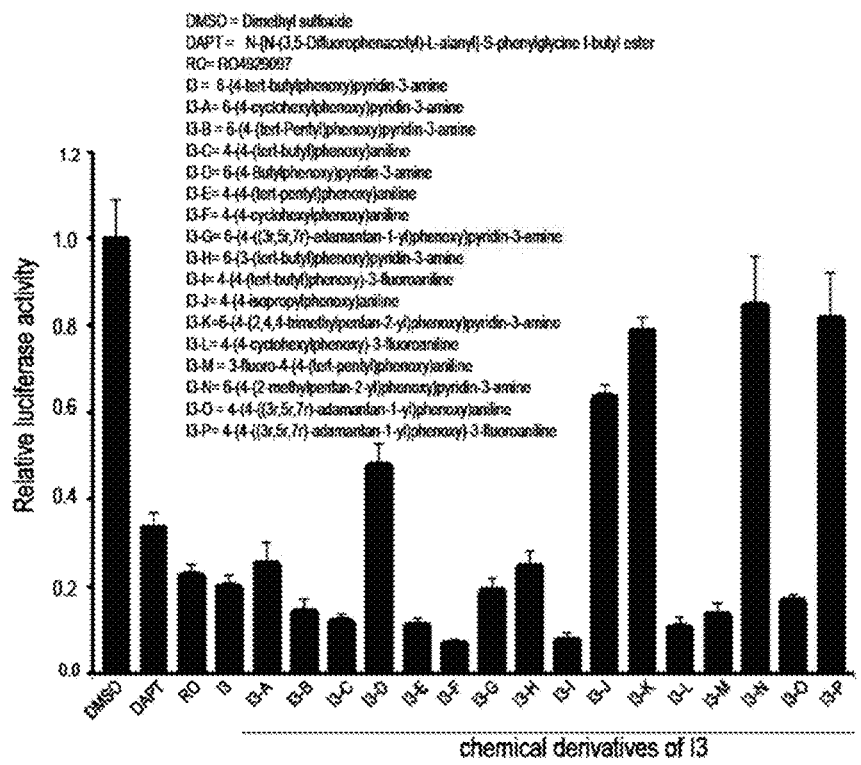

FIG. 10 shows Notch inhibitory activity of chemical derivatives of 6-(4-Tert-Butylphenoxy)Pyridin-3-Amine (I3). Different chemical derivatives of 6-(4-Tert-Butylphenoxy)Pyridin-3-Amine (I3) were tested in DL4-N1 coculture assay and Notch activity levels were measured using Notch driven luciferase reporter gene. Derivatives I3-A, I3-B, I3-C, I3-E, I3-G, I3-H, I3-M and I3-N exhibit anti-Notch activity comparable to 6-(4-Tert-Butylphenoxy)Pyridin-3-Amine (I3), while derivatives I3-F and I3-I appear to have enhanced activity.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term "comprise/comprising" is generally used in the sense of include/including, that is to say permitting the presence of one or more features or components. The terms "comprise" and "comprising" also encompass the more restricted ones "consist" and "consisting".

As used in the specification and claims, the singular form "a", "an" and "the" include plural references unless the context clearly dictates otherwise.

For the ease of reading, the term "compound(s) of the invention" or "compound(s) according to the invention" used throughout the description refers to the compound 6-(4-Tert-Butylphenoxy)Pyridin-3-Amine (I3) (CAS number 218457-67-1), derivatives of said I3, salts or solvates of the compound I3 or of the derivatives, and to isomers, including enantiomers, stereoisomers, rotamers, tautomers and racemates of the compound I3, chemical modified I3 compounds and derivatives of said I3 compounds.

As used herein the terms "subject" is well-recognized in the art, and, refers to a mammal, including dog, cat, rat, mouse, monkey, cow, horse, goat, sheep, pig, camel, and, most preferably, a human. In some embodiments, the subject is a subject in need of treatment or a subject with a disease or disorder, such as cancer. However, in other embodiments, the subject can be a normal subject or a subject who has already undergone a treatment against cancer. The term does not denote a particular age or sex. Thus, adult, children and newborn subjects, whether male or female, are intended to be covered.

The terms "cancer", "cancer cells", "cell proliferative diseases" and "cell proliferative disorders" as used herein refer to or describe the physiological condition in mammals that is typically characterized by unregulated cell growth. According to the present invention, cancer refers preferably to solid tumors, such as brain, breast, prostate, colorectum, kidney, lung, sarcoma, or melanoma and liquid tumors, affecting the blood, such as leukemia. More preferably according to the present invention, cancers are Notch dependent cancers selected from the group comprising T cell-Acute lymphoblastic leukemia (T-ALL), chronic myeloid leukemia (CML), chronic lymphocytic leukemia (CLL), Mantle cell lymphoma, breast cancer, pancreatic cancer, prostate cancer, melanoma, brain tumors, tumor angiogenesis, colorectal cancer. Alternatively, the Notch dependent cancer is resistant to γ-secretase inhibitor treatment. Examples of γ-secretase inhibitor treatment comprise 1) Gamma secretase inhibitor RO4929097 and Cediranib Maleate in treating patients with advanced solid tumors (NCT01131234), 2) Gamma-Secretase Inhibitor RO4929097 in Treating Young Patients With Relapsed or Refractory Solid Tumors, CNS Tumors, Lymphoma, or T-Cell Leukemia (NCT01088763), 3) Study of MK-0752 in combination with Tamoxifen or Letrozole to treat early stage breast cancer (NCT00756717), 4) GDC-0449 and RO4929097 in treating patients with Advances or metastatic sarcoma (NCT01154452) 5) RO4929097 and Erlotinib Hydrochloride in treating patients with stage IV or recurrent Non-Small Cell Lung Cancer (NCT01193881), 6) Bicalutamide and RO4929097 in treating patients with previously treated prostate cancer (NCT01200810), 7) RO4929097 in treating patients with recurrent invasive Gliomas (NCT01269411), 8) A Notch signaling pathway inhibitor for patients with T-cell Acute Lymphoblastic Leukemia/Lymphoma (ALL) (NCT00100152) and 9) RO4929097 in treating patients with metastatic colorectal cancer (NCT01116687).

The Notch signalling pathway is evolutionarily conserved and the basic molecular players in this pathway are ligands (Delta and Jagged), Notch receptors, and the transcription factors (Shih IeM, Wang T L in Cancer Res 2007; 67(5): 1879-82). Notch is a transmembrane heterodimeric receptor and there are four distinct members (Notch1, Notch2, Notch3 and Notch4) in humans and rodents. In a physiologic condition, binding of the Notch ligand to its receptor initiates Notch signalling by releasing the intracellular domain of the Notch receptor (Notch-ICD) through a cascade of proteolytic cleavages by both α-secretase (also called tumor necrosis factor-α-converting enzyme) and γ-secretase. The released intracellular Notch-ICD then translocates into the nucleus where it modulates gene expression primarily by binding to a ubiquitous transcription factor, CBF1, suppressor of hairless, Lag-1 (CSL). This binding recruits transcription activators to the CSL complex and converts it from a transcriptional repressor into an activator, which turns on several downstream effectors. The physiologic functions of Notch signalling are multifaceted, including maintenance of stem cells, specification of cell fate, and regulation of differentiation in development as well as in oncogenesis.

In cancers, molecular genetic alterations, such as chromosomal translocation, point mutations, and chromosomal amplification at the Notch receptor loci, are the known mechanisms for constitutive activation of Notch pathway. Despite the different mechanisms, they all result in increased levels of intracellular Notch-IC. The oncogenic potential of Notch was first discovered in human T-cell acute lymphoblastic leukemia (T-ALL). While Notch1 signalling is essential for normal development of T-cell progenitors, constitutive activation of Notch1 signalling due to molecular genetic alterations is associated with T-ALL. For example, interstitial deletions of the extracellular portion of human Notch1 due to (7; 9) chromosomal translocation are associated with ~1% of T-ALL cases and activating point mutations of Notch1 are present in about 50% of T-ALL cases. Formation of T-cell leukemia/lymphoma was observed in a Notch-ICD transgenic mouse model, which indicates a causal role of Notch activation in T-ALL development. In non-small cell lung cancer, chromosomal translocation (15; 19) has been identified in a subset of tumors, and the translocation is thought to elevate Notch3 transcription in tumors. In ovarian cancer, Notch3 gene amplification was found to occur in about 19% of tumors, and overexpression of Notch3 was found in more than half of the ovarian serous carcinomas. Similarly, Notch signalling activation has been shown in the development of breast cancer. In animal models, constitutively active Notch4 expression causes mammary tumors in mice and Notch1-activating mutations contribute to the development of T-ALL. A recent study further shows that overexpression of activated Notch1 and Notch3 in transgenic mice blocks mammary gland development and induces mouse breast tumors. Notch signalling activation has also been implicated in lung and bone metastasis of breast cancer cells. Overexpression of Notch3 is sufficient to induce choroid plexus tumor formation in a mouse model, suggesting a role of Notch3 in the development of certain types of brain tumors.

With the aim of conducting a High-Through put Screening (HTS) to identify novel modulators (inhibitors) of Notch signalling, Applicants have established a coculture assay to induce a ligand-receptor mediated activation of the pathway. The coculture assay was established using Notch ligand DL4 and Notch1 receptor specifically, because DL4-N1 ligand-receptor mediated pathway activation plays an important role in pathophysiological conditions such as tumor angiogenesis and the role of Notch1 receptor in inducing T cell leukemia. Since this assay depends on the expression and interaction between DL4 ligand and Notch1 receptor, it provides an opportunity to interrogate ligand-receptor interactions-induced Notch signalling in a controlled manner. The miniaturization of this assay into a 96 well plate and 384 well plate format helped Applicants to adapt this assay to conduct HTS. The use of this coculture assay to screen siRNA or small molecule libraries can lead to the identification of proteins or chemical compounds that are able to modulate Notch signalling at different steps along the pathway. For example, a HTS using siRNA or small molecule libraries can yield modulators of the pathway able to act in the signal sending or signal receiving cells. Small molecule or protein mediated alterations in the recycling or trafficking of the ligands and receptors to the plasma membrane can potentially block the Notch pathway and could be studied using this assay. In addition, this assay can also help identify proteins or chemical entities able to block ligand-receptor interactions, ADAM10/17 mediated S2 cleavage or γ-secretase catalyzed S3 cleavage of the Notch receptor, nuclear translocation of the active form of Notch or entities able to block transcriptional activation complex.

Applicants have also been able to screen three different chemical compound libraries (Microsource NIMDS, Prestwick and Maybridge Hit finder) that have led to the identification of several chemicals, which are able to block Notch signalling at different levels along the pathway.

The use of the Notch-independent *renilla* system as an internal control allowed Applicants to eliminate cytotoxic chemical compounds, thereby limiting the rate of false positive hits. In addition, this cell-based assay also helped to circumvent issues related to the cell permeability of the chemical compounds for further hit validation.

The development of DL4:N1 coculture assay system laid the foundation for a HTS campaign. This assay provided a robust and sensitive readout system to identify novel modulators (inhibitors) of the Notch pathway.

Applicants identified several chemical compounds for their ability to block the Notch pathway activation. Among those, they identified the compound 6-(4-Tert-Butylphenoxy)Pyridin-3-Amine (I3) (CAS number 218457-67-1) for its ability to block the Notch pathway activation.

Thus, the present invention relates to 6-(4-Tert-Butylphenoxy)Pyridin-3-Amine (I3) of Formula I

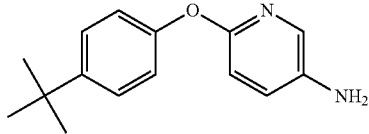

Formula I for use in the treatment and/or prevention of a cancer.

The present invention also encompasses chemical modifications of the 6-(4-Tert-Butylphenoxy)Pyridin-3-Amine (I3) (CAS number: 218457-67-1) to prolong their circulating lifetimes. Non-limiting examples of methods for transiently, or reversibly, pegylating drugs, including polypeptide-based drugs, are provided in U.S. Pat. No. 4,935,465 (issued in Jun. 19, 1990) and U.S. Pat. No. 6,342,244 (issued Jan. 29, 2002); and in U.S. published applications number US2006/0074024. One skilled in the art would typically find more details about PEG-based reagents in, for example, published applications WO2005047366, US2005171328, and those listed on the NEKTAR PEG Reagent Catalog® 2005-2006 (Nektar Therapeutics, San Carlos, Calif.).

The present invention further encompasses chemical derivatives of said I3 having Notch signalling pathway inhibition properties. Applicants have shown that 6-(4-Tert-Butylphenoxy)Pyridin-3-Amine (I3) and its derivatives target Notch signalling at the transcriptional activation complex in the nucleus, human tumors resistant to γ-secretase inhibitors due to above mentioned mutations are expected to respond to 6-(4-Tert-Butylphenoxy)Pyridin-3-Amine (I3)

treatment. In addition, 6-(4-Tert-Butylphenoxy)Pyridin-3-Amine (I3) appears to selectively target Notch signalling, thus limiting its off-target toxic effects.

These derivatives all share the follow common structure:

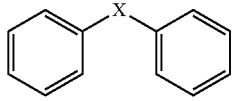

Preferably, in said derivatives X is O and position 3 (or para) is NH2.

Most preferably, the derivative having Notch signalling pathway inhibition properties is selected from the non-limiting group comprising

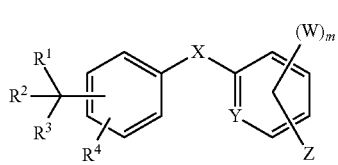

Formula II wherein m is an integer selected from 1 to 4;
W is selected from H and halogens; the halogen is selected from F—, Cl—, Br— or I—;
R1, R2, R3, R4 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 1 to 15;
X is O, S, CR5R6, NR7, NHCOR8, or NHSO2R9; where R5, R6, R7, R8, R9 are each independently selected from the group consisting in selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, or $(CH_2)_nCH_3$, the subscript n is an integer independently selected from 1 to 15;
Y is N or CH;
Z is H, $NO_2$, OH, NR10R11 where R10 and R11 are each independently selected from the group consisting in H and $(CH_2)_nCH_3$, NHCOR12 where R12 is selected from the group consisting of $(CH_2)_nCH_3$, aromatic and heteroaromatics such as phenyl, naphthyl, pyrrolyl, furanyl, thiofuranyl, pyrimidinyl, imidazolyl, COOR13 where R13 is selected from the group consisting of H, $(CH_2)_nCH_3$, aromatic and heteroaromatics such as phenyl, naphthyl, pyrrolyl, furanyl, thiofuranyl, pyrimidinyl, imidazolyl, $NHSO_2R14$ where R14 is selected from the group consisting of phenyl, 2-, 3- or 4, substituted phenyl, naphthyl, heteroaromatics such as pyrrolyl, furanyl, thiofuranyl, pyrimidinyl, imidazolyl, benzyl, $(CH_2)_nCH_3$, the subscript n is an integer independently selected from 1 to 15;

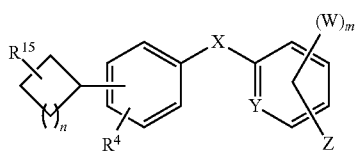

Formula III wherein m is an integer selected from 1 to 4;
W is selected from H and halogens; the halogen is selected from F—, Cl—, Br— or I—;
R4, R15 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 1 to 15;
X is O, S, CR5R6, NR7, NHCOR8 or NHSO2R9; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, $(CH_2)_nCH_3$; the subscript n is an integer independently selected from 1 to 15;
Y is N or CH;
Z is H, $NO_2$, OH, NR10R11 where $R^{11}$ and are each independently selected from the group consisting in H, $(CH_2)_nCH_3$, $NHCOR^{12}$ where R12 is $(CH_2)_nCH_3$, aromatic and heteroaromatics selected from the group comprising phenyl, naphthyl, pyrrolyl, furanyl, thiofuranyl, pyrimidinyl, imidazolyl, COOR13 where R13 is H, $(CH_2)_nCH_3$, aromatic and heteroaromatics selected from the group comprising phenyl, naphthyl, pyrrolyl, furanyl, thiofuranyl, pyrimidinyl, imidazolyl, $NHSO_2R14$ where R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, $(CH_2)_nCH_3$, the subscript n is an integer independently selected from 1 to 15;

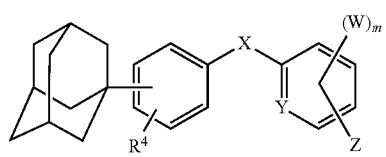

Formula IV wherein m is an integer selected from 1 to 4;
W is selected from H and halogens; the halogen is selected from F—, Cl—, Br— or I—;
R4 is H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 1 to 15;
X is O, S, CR5R6, NR7, NHCOR8 or NHSO2R9; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, $(CH_2)_nCH_3$; the subscript n is an integer independently selected from 1 to 15;
Y is N or CH;
Z is H, $NO_2$, OH, NR10R11 where $R^{11}$ and are each independently selected from the group consisting in H, $(CH_2)_nCH_3$, $NHCOR^{12}$ where R12 is $(CH_2)_nCH_3$, aromatic and heteroaromatics selected from the group comprising phenyl, naphthyl, pyrrolyl, furanyl, thiofuranyl, pyrimidinyl, imidazolyl, COOR13 where R13 is H, $(CH_2)_nCH_3$, aromatic and heteroaromatics selected from the group comprising phenyl, naphthyl, pyrrolyl, furanyl, thiofuranyl, pyrimidinyl, imidazolyl, $NHSO_2R14$ where R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, $(CH_2)_nCH_3$, the subscript n is an integer independently selected from 1 to 15;

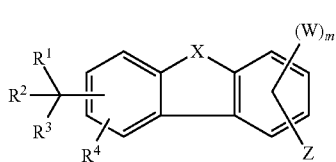

Formula V wherein m is an integer selected from 1 to 4;

W is selected from H and halogens; the halogen is selected from F—, Cl—, Br— or I—;

R1, R2, R3, R4 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 1 to 15;

X is O, S, CR5R6, NR7, NHCOR8 or $NHSO_2R9$; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, $(CH_2)_nCH_3$; the subscript n is an integer independently selected from 1 to 15;

Z is H, $NO_2$, OH, NR10R11 where R10 and R11 are each independently selected from the group consisting in H, $(CH_2)_nCH_3$, NHCOR12 where R12 is $(CH_2)_nCH_3$, aromatic and heteroaromatics selected form the group comprising phenyl, naphthyl, pyrrolyl, furanyl, thiofuranyl, pyrimidinyl, imidazolyl, COOR13 where R13 is H, $(CH_2)_nCH_3$, aromatic and heteroaromatics selected from the group comprising phenyl, naphthyl, pyrrolyl, furanyl, thiofuranyl, pyrimidinyl, imidazolyl, $NHSO_2R14$ with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, $(CH_2)_nCH_3$; the subscript n is an integer independently selected from 1 to 15;

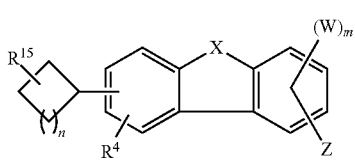

Formula VI wherein m is an integer selected from 1 to 4;
W is selected from H and halogens; the halogen is selected from F—, Cl—, Br— or I—;

R4, R15 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 0 to 15;

X is O, S, CR5R6, NR7, NHCOR8 or $NHSO_2R9$; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, $(CH_2)_nCH_3$; the subscript n is an integer independently selected from 0 to 15;

Z is H, $NO_2$, OH, NR10R11 where R10 and R11 are each independently selected from the group consisting in H, $(CH_2)_nCH_3$, NHCOR12 where R12 is $(CH_2)_nCH_3$, aromatic and heteroaromatics selected form the group comprising phenyl, naphthyl, pyrrolyl, furanyl, thiofuranyl, pyrimidinyl, imidazolyl, COOR13 where R13 is H, $(CH_2)_nCH_3$, aromatic and heteroaromatics selected from the group comprising phenyl, naphthyl, pyrrolyl, furanyl, thiofuranyl, pyrimidinyl, imidazolyl, $NHSO_2R14$ with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, $(CH_2)_nCH_3$; the subscript n is an integer independently selected from 0 to 15;

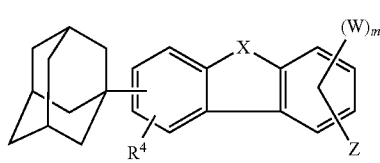

Formula VII wherein m is an integer selected from 1 to 3;
W is selected from H and halogens; the halogen is selected from F—, Cl—, Br— or I—;

R4 is H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$ alkenyl, alkynyl; the subscript n is an integer independently selected from 0 to 15;

X is O, S, CR5R6, NR7, NHCOR8 or $NHSO_2R9$; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, $(CH_2)_nCH_3$; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, $(CH_2)_nCH_3$; the subscript n is an integer independently selected from 0 to 15;

Z is H, $NO_2$, OH, NR10R11 where R10 and R11 are each independently selected from the group consisting in H, $(CH_2)_nCH_3$, NHCOR12 where R12 is $(CH_2)_nCH_3$, aromatic and heteroaromatics selected form the group comprising phenyl, naphthyl, pyrrolyl, furanyl, thiofuranyl, pyrimidinyl, imidazolyl, COOR13 where R13 is H, $(CH_2)_nCH_3$, aromatic and heteroaromatics selected from the group comprising phenyl, naphthyl, pyrrolyl, furanyl, thiofuranyl, pyrimidinyl, imidazolyl, NHSO₂R14 with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15;

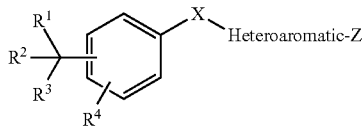

Formula VIII wherein the heteroaromatic is an aminopyrrole, aminofurane, aminothiofurane, or a pyrimidine;
R1, R2, R3, R4 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, (CH₂)$_n$CH₃ alkenyl, alkynyl; the subscript n is an integer independently selected from 0 to 15;
X is O, S, CR5R6, NR7, NHCOR8, or NHSO2R9; where R5, R6, R7, R8, R9 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, or (CH2)$_n$CH3, the subscript n is an integer independently selected from 0 to 15;
Z is H, NO₂, OH, NR10R11 where R10 and R11 are each independently selected from the group consisting in H, (CH₂)$_n$CH₃, NHCOR12 where R12 is (CH₂)$_n$CH₃, aromatic and heteroaromatics selected form the group comprising phenyl, naphthyl, pyrrolyl, furanyl, thiofuranyl, pyrimidinyl, imidazolyl, COOR13 where R13 is H, (CH₂)$_n$CH₃, aromatic and heteroaromatics selected from the group comprising phenyl, naphthyl, pyrrolyl, furanyl, thiofuranyl, pyrimidinyl, imidazolyl, NHSO₂R14 with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15;

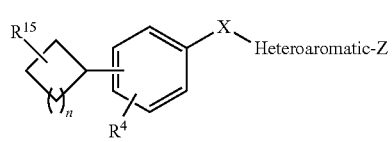

Formula IX wherein the subscript n is an integer independently selected from 1 to 15;
the heteroaromatic is an aminopyrrole, aminofurane, aminothiofurane, or a pyrimidine;
R4, R15 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, (CH₂)$_n$CH₃ alkenyl, alkynyl; the subscript n is an integer independently selected from 0 to 15;
X is O, S, CR5R6, NR7, NHCOR8 or NHSO₂R9; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, (CH₂)$_n$CH₃; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15;
Z is H, NO₂, OH, NR10R11 where R10 and R11 are each independently selected from the group consisting in H, (CH₂)$_n$CH₃, NHCOR12 where R12 is (CH₂)$_n$CH₃, aromatic and heteroaromatics selected form the group comprising phenyl, naphthyl, pyrrolyl, furanyl, thiofuranyl, pyrimidinyl, imidazolyl, COOR13 where R13 is H, (CH₂)$_n$CH₃, aromatic and heteroaromatics selected from the group comprising phenyl, naphthyl, pyrrolyl, furanyl, thiofuranyl, pyrimidinyl, imidazolyl, NHSO₂R14 with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15;

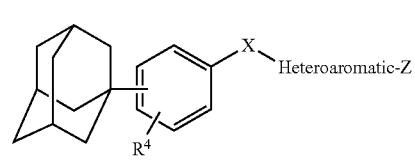

Formula X wherein the heteroaromatic is an aminopyrrole, aminofurane, aminothiofurane, or a pyrimidine;
R4 is H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, (CH₂)$_n$CH₃ alkenyl, alkynyl; the subscript n is an integer independently selected from 0 to 15;
X is O, S, CR5R6, NR7, NHCOR8 or NHSO₂R9; R5, R6 and R7 are each independently selected from the group consisting in H, phenyl, 2-, 3- or 4-substituted phenyl, 2- or 3-naphthyl, pyrrolyl, furanyl, thiofuranyl, pyrimidinyl, imidazolyl, benzyl, isoPropyl, tertButyl, (CH₂)$_n$CH₃; R8 and R9 are each independently selected from the group consisting in phenyl, 2-, 3- or 4-substituted phenyl, 2- or 3-naphthyl, or heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15;
Z is H, NO₂, OH, NR10R11 where R10 and R11 are each independently selected from the group consisting in H, (CH₂)$_n$CH₃, NHCOR12 where R12 is (CH₂)$_n$CH₃, aromatic and heteroaromatics selected form the group comprising phenyl, naphthyl, pyrrolyl, furanyl, thiofuranyl, pyrimidinyl, imidazolyl, COOR13 where R13 is H, (CH₂)$_n$CH₃, aromatic and heteroaromatics selected from the group comprising phenyl, naphthyl, pyrrolyl, furanyl, thiofuranyl, pyrimidinyl, imidazolyl, NHSO₂R14 with R14 is phenyl, 2-, 3- or 4, substituted phenyl, naphthyl, heteroaromatics selected from the group comprising pyrrolyl, furanyl, thiofuranyl, pyrimidinyl, imidazolyl, benzyl, (CH₂)$_n$CH₃; the subscript n is an integer independently selected from 0 to 15.

Even more preferably, the derivative having Notch signalling pathway inhibition properties is selected from the group consisting in

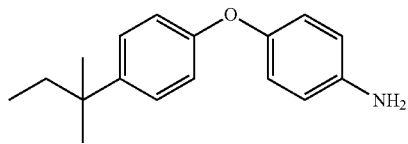
Formula II d 4-(4-(tert-pentyl)phenoxy)aniline

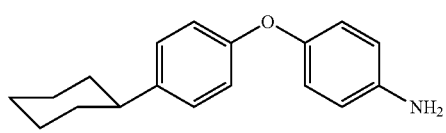
Formula III a 4-(4-cyclohexylphenoxy)aniline

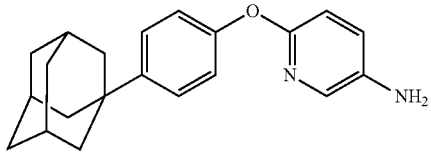
Formula IV a 6-(4-((3r,5r,7r)-adamantan-1-yl)phenoxy)pyridin-3-amine

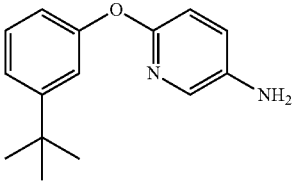
Formula II e 6-(3-(tert-butyl)phenoxy)pyridin-3-amine

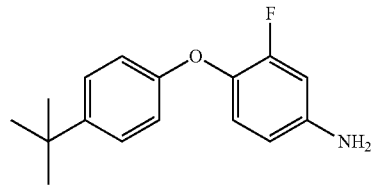
Formula II f 4-(4-(tert-butyl)phenoxy)-3-fluoroaniline

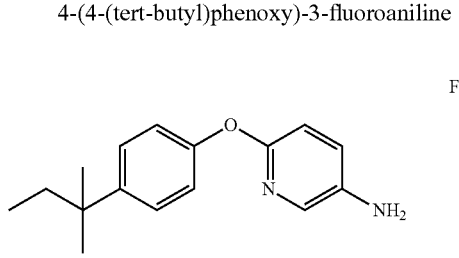
Formula II g 6-(4-(tert-Pentyl)phenoxy)pyridin-3-amine

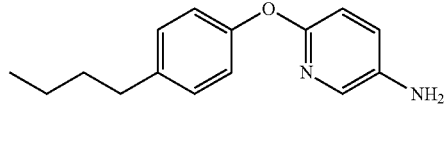
Formula II h 6-(4-Butylphenoxy)pyridin-3-amine

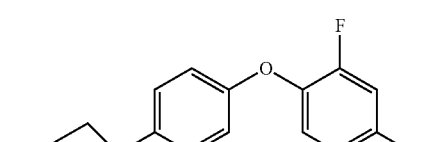
Formula III b 4-(4-Cyclohexylphenoxy)-3-fluoroaniline

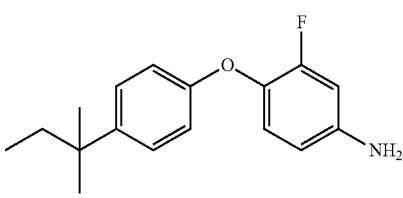
Formula II i

3-Fluoro-4-(4-(tert-pentyl)phenoxy)aniline

Formula II j 6-(4-(2-Methylpentan-2-yl)phenoxy)pyridin-3-amine

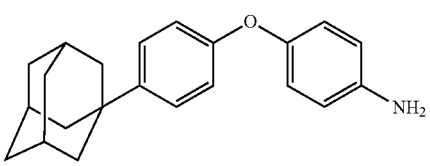
Formula IV b 4-(4-((3r,5r,7r)-Adamantan-1-yl)phenoxy)aniline

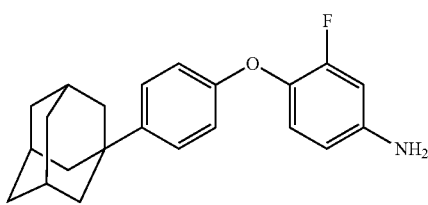

4-(4-((3r,5r,7r)-Adamantan-1-yl)phenoxy)-3-fluoroaniline

Formula IV c

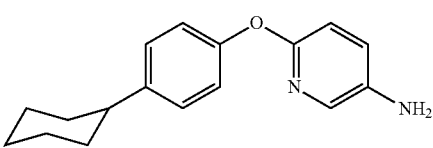

6-(4-cyclohexylphenoxy)pyridin-3-amine

Formula III c

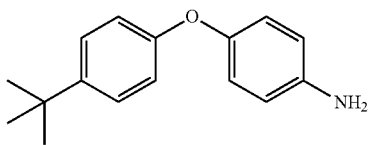

4-(4-(tert-butyl)phenoxy)aniline

Formula II k

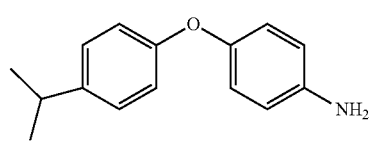

4-(4-isopropylphenoxy)aniline, and

Formula II l

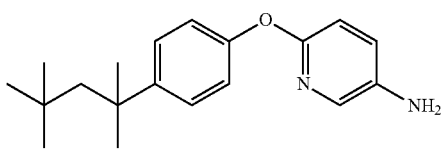

6-(4-(2,4,4-trimethylpentan-2-yl)phenoxy)pyridin-3-amine

Formula II m

The invention also relates to salts or solvates of the compound I3, chemical modified I3 compounds and derivatives of said I3 compounds of the invention. Preferably, these salts and/or solvates are pharmaceutically acceptable. According to the present invention, pharmaceutically acceptable salts are produced from acidic inorganic or organic compounds, or alkaline inorganic or organic compounds. As used herein, the phrase "pharmaceutically acceptable salt" refers to a salt that retains the biological effectiveness of the free acids and bases of a specified compound and that is not biologically or otherwise undesirable.

Unless specified otherwise, it is further understood that all isomers, including enantiomers, stereoisomers, rotamers, tautomers and racemates of the compound I3, chemical modified I3 compounds and derivatives of said I3 compounds of the invention are contemplated as being part of this invention. The invention includes stereoisomers in optically pure form and in admixture, including racemic mixtures. Isomers can be prepared using conventional techniques, either by reacting optically pure or optically enriched starting materials or by separating isomers of compounds of the present invention.

"Racemates" refers to a mixture of enantiomers.

"Stereoisomer" or "stereoisomers" refer to compounds that differ in the chirality of one or more stereocenters. Stereoisomers include enantiomers and diastereomers. The compound I3, chemical modified I3 compounds and derivatives of said I3 compounds of this invention may exist in stereoisomeric form if they possess one or more asymmetric centres or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring=N-moiety such as pyrazoles, imidazoles, benzimidazoles, triazoles, and tetrazoles.

A skilled person will know that, if compound I3, chemical modified I3 compounds and derivatives of said I3 compounds of the invention contain charged group, a suitable counterion will be derived from an organic or inorganic acid. Such counterions include halide (such as chloride, bromide, fluoride, iodide), sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. If the polar moiety is a negatively charged group, a suitable counterion will be selected from sodium, ammonium, barium, calcium, copper, iron, lithium, potassium and zinc, and the like.

Figure 1:
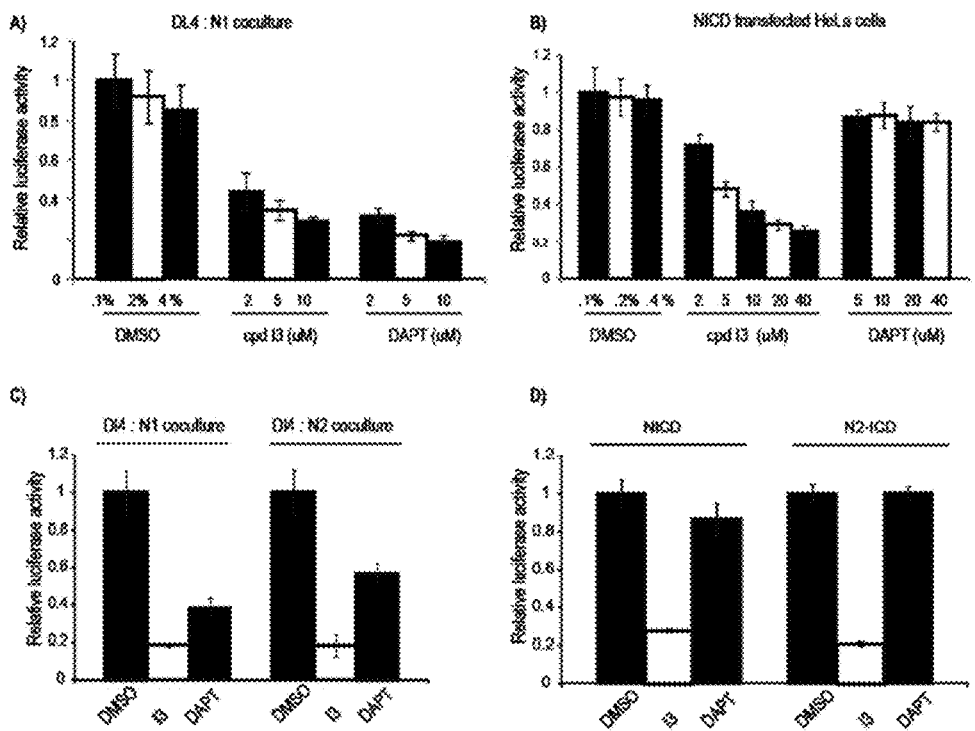
FIG. 1 shows 6-(4-Tert-Butylphenoxy)Pyridin-3-Amine (I3) (CAS number 218457-67-1) blocks NICD mediated Notch signalling activation. A) N1-HeLa cells were co-transfected with pcDNA3.Notch1 expression plasmid, pGL4.26-12×CSL luciferase and SV40 *renilla* plasmids. DL4- and N1-HeLa cells were cocultured in a 96 well plate in 1:1 ratio (20,000:20,000 cells/well) and treated with DMSO or with 2, 5 and 10 µM of I3 and DAPT for 24 hours. The Notch pathway activation was measured by quantifying Notch signalling driven luciferase reporter assay. Treatment of DL4:N1 coculture assay with 6-(4-Tert-Butylphenoxy) Pyridin-3-Amine (I3) and DAPT causes a concentration dependent decrease in Notch signalling activation. B) HeLa cells were transfected with NICD and treated with DMSO or with 2, 5, 10, 20 and 40 µM of 6-(4-Tert-Butylphenoxy) Pyridin-3-Amine (I3). As a control co-cultured cells were also treated with 5, 10, 20 and 40 µM of DAPT. The pathway activation was measured using Notch driven luciferase reporter assay. 6-(4-Tert-Butylphenoxy)Pyridin-3-Amine (I3) treatment of NICD expressing cells led to an attenuation of the signalling, while DAPT treatment had no effect on Notch signalling activation mediated by NICD. C) DL4:N1 and DL4:N2 coculture assay was treated with I3 and DAPT (each 10 µM) for 24 hours. The effect of 6-(4-Tert-Butylphenoxy)Pyridin-3-Amine (I3) and DAPT on DL4-N1 and DL4-N2 driven pathway activation was measured by Notch driven luciferase activity. Both I3 and DAPT treatment block Notch1 and Notch2 induced pathway activation. D) 6-(4-Tert-Butylphenoxy)Pyridin-3-Amine (I3) inhibits pathway activation via intracellular domains of Notch1 (NICD) and Notch2 (N2-ICD).
Figure 2:
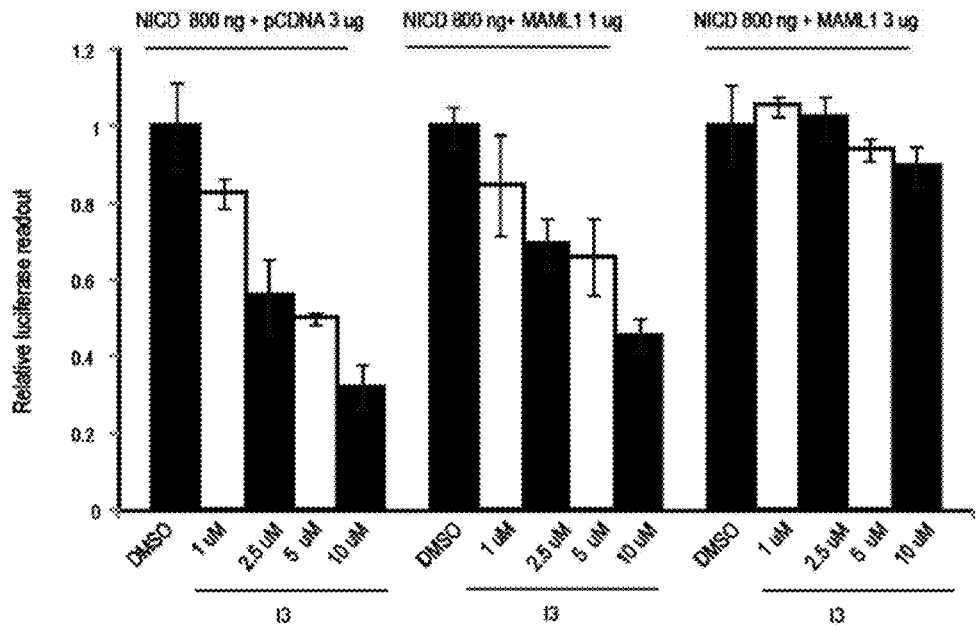
FIG. 2 shows 6-(4-Tert-Butylphenoxy)Pyridin-3-Amine (I3) mediated inhibition of Notch signalling can be rescued with increasing concentration of MAML1. HeLa cells were co-transfected 800 ng of NICD+3 µg of pCDNA3.1 or 800 ng of NICD+1 µg of MAML1-FLAG or 800 ng of NICD+3 µg of MAML1-FLAG expression vectors. To measure Notch pathway activation, pGL4.26-12×CSL luciferase plasmid was also introduced into the cells. SV40 *renilla* was used as an internal control. Cells transfected with different combinations and amounts of plasmid were treated with DMSO or increasing concentration of 6-(4-Tert-Butylphenoxy)Pyridin-3-Amine (I3) (1, 2.5, 5 and 10 μM) for 24 hours. 12×CSL driven luciferase activity was measured using dual luciferase assay system. In the absence of MAML1, 6-(4-Tert-Butylphenoxy)Pyridin-3-Amine (I3) could block Notch signalling activations, but Notch inhibitory effect of 6-(4-Tert-Butylphenoxy)Pyridin-3-Amine (I3) was diminished with increasing amount of MAML1.

Surprisingly, the chemical compound 6-(4-Tert-Butylphenoxy)Pyridin-3-Amine (I3) was identified as a potential Notch inhibitor. Interestingly, 6-(4-Tert-Butylphenoxy)Pyridin-3-Amine (I3) was found to block NICD mediated pathway activation (FIG. 1). Because of its ability to attenuate NICD mediated Notch activation, 6-(4-Tert-Butylphenoxy)Pyridin-3-Amine (I3) is able to block proliferation of NICD overexpressing leukemic cell lines which are resistant to DAPT (a-γ-secretase inhibitor, N—[N-(3,5-difluorophenacetyl-Lalanyl)]-(S)-phenylglycine t-butyl ester) (FIG. 5). The Notch inhibitory potential of 6-(4-Tert-Butylphenoxy)Pyridin-3-Amine (I3) was further confirmed by the down-regulation of Notch target genes in human T-ALL cell lines (FIG. 3) and Affymetrix geneChip array (data not shown). The fact that 6-(4-Tert-Butylphenoxy)Pyridin-3-Amine (I3)

can induce differentiation of C2C12 cells into MHC expressing multinucleated myotubes further validated the anti-Notch role of 6-(4-Tert-Butylphenoxy)Pyridin-3-Amine (I3) (data not shown). The Notch pathway inhibition caused by 6-(4-Tert-Butylphenoxy)Pyridin-3-Amine (I3) can be rescued by the overexpression of MAML1 above certain levels. For example, 6-(4-Tert-Butylphenoxy)Pyridin-3-Amine (I3) was able to block the signalling with 800 ng of NICD and 1 μg of MAML1 was transiently introduced into the cells, however when the amount of MAML1 was increased to 3 μg, 6-(4-Tert-Butylphenoxy)Pyridin-3-Amine (I3) was no longer able to block the pathway activation (FIG. 2). These data suggest that, 6-(4-Tert-Butylphenoxy)Pyridin-3-Amine (I3) may interfere with the Notch transcriptional activation complex thereby inhibiting the signalling activation. Microscopic studies by introduction of MAML at levels where 6-(4-Tert-Butylphenoxy)Pyridin-3-Amine (I3) could still block the pathway activation showed that 6-(4-Tert-Butylphenoxy)Pyridin-3-Amine (I3) treatment does not impede co-localization of NICD, MAML1 and CSL/RBP-jk in the sub-nuclear compartments (data not shown). Without being bound to theory, one of the possible mechanisms of action of 6-(4-Tert-Butylphenoxy)Pyridin-3-Amine (I3) could be to disrupt the recruitment of transcriptional coactivators to the core CSL/RBP-jk-NICD-MAML1 complex. Therefore, the status of additional coactivators involved in the formation of functional transcriptional activation complex still needs to be determined. Under physiological conditions, following the formation of CSL/RBP-jk-NICD-MAML1 complex, CBP/p300 histone acetyltransferase (HAT) is recruited to the complex leading to its autoacetylation and acetylation of histone 3 and 4.

6-(4-Tert-Butylphenoxy)Pyridin-3-Amine (I3), as well as derivatives thereof, were further investigated in an in vivo context to determine their Notch inhibitory as well as toxic side effects in the mice. Notch signalling is essential for the maintenance of normal homoeostasis in the intestine. Genetic ablation or pharmacological inhibition of Notch1 and Notch2 signalling in the intestine leads to goblet cell metaplasia in the intestine. Since, 6-(4-Tert-Butylphenoxy) Pyridin-3-Amine (I3) has been observed to block Notch1 and Notch2 mediated signalling, mice treated with 6-(4-Tert-Butylphenoxy)Pyridin-3-Amine (I3) were expected to develop goblet cell metaplasia. Surprisingly, treatment of mice with 25 mg/kg of 6-(4-Tert-Butylphenoxy)Pyridin-3-Amine (I3) for 7 days (more than a month in case of xenotransplants) did not perturb intestinal homeostasis and without any indication of goblet cell accumulation (data not shown). This unexpected outcome could be due to two reasons. One possible explanation could be that the concentration of 6-(4-Tert-Butylphenoxy)Pyridin-3-Amine (I3) (25 mg/kg) used is not sufficient to block Notch pathway activation in the intestine. However, a second more plausible explanation could be the differences in the composition of transcriptional activation complexes downstream of Notch1 and Notch2 signalling. Due to these possible differences, Notch1 and Notch2 mediated signalling may have different sensitivities against 6-(4-Tert-Butylphenoxy)Pyridin-3-Amine (I3) treatment.

Figure 7:
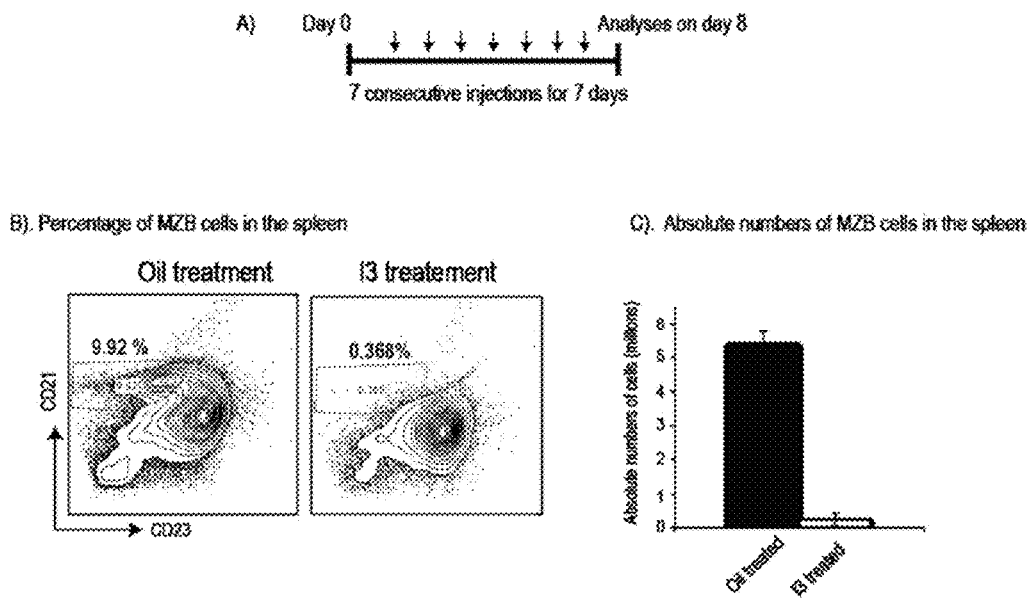
FIG. 7 shows 6-(4-Tert-Butylphenoxy)Pyridin-3-Amine (I3) mimics genetic loss of Notch2 signalling phenotype in the spleen. Loss of Notch signalling in the spleen leads to a reduction in Marginal Zone B cells (MZB) cells in the spleen. A) Schematics of the experimental plan. B) Mice (n=2) were treated with oil or 25 mg/kg of 6-(4-Tert-Butylphenoxy)Pyridin-3-Amine (I3) for 7 consecutive days. Spleens were analyzed on day 8. Using B220 specific antibodies, B cells in the spleen were identified. MZB cells within the B cell compartment were detected using antibodies against CD23 and CD21 cell surface markers. The treatment of mice with 6-(4-Tert-Butylphenoxy)Pyridin-3-Amine (I3) causes a significant reduction in the percentage of MZB cells in the spleen. C) 6-(4-Tert-Butylphenoxy)Pyridin-3-Amine (I3) treatment causes a reduction in the absolute numbers of MZB cells in the spleen when compared to vehicle treated animals.

Notch signalling plays an important role in the regulation of hematopoietic system. For instance, DL4-Notch1 signalling is essential for T cell development in the thymus. Notch2 and MAML1 mediated pathway activation is critical for Marginal Zone B (MZB) cells development in the spleen. To address whether 6-(4-Tert-Butylphenoxy)Pyridin-3-Amine (I3) can impair Notch dependent MZB cell development in the spleen, C57Bl6 mice were treated with 25 mg/kg of 6-(4-Tert-Butylphenoxy)Pyridin-3-Amine (I3) for 7 days and analyzed on day 8. Flow cytometry analyses using antibodies against B220, CD21 and CD23 revealed that 6-(4-Tert-Butylphenoxy)Pyridin-3-Amine (I3) treatment causes a reduction the percentage and absolute numbers of MZB cells in the spleen (FIG. 7).

Figure 8:
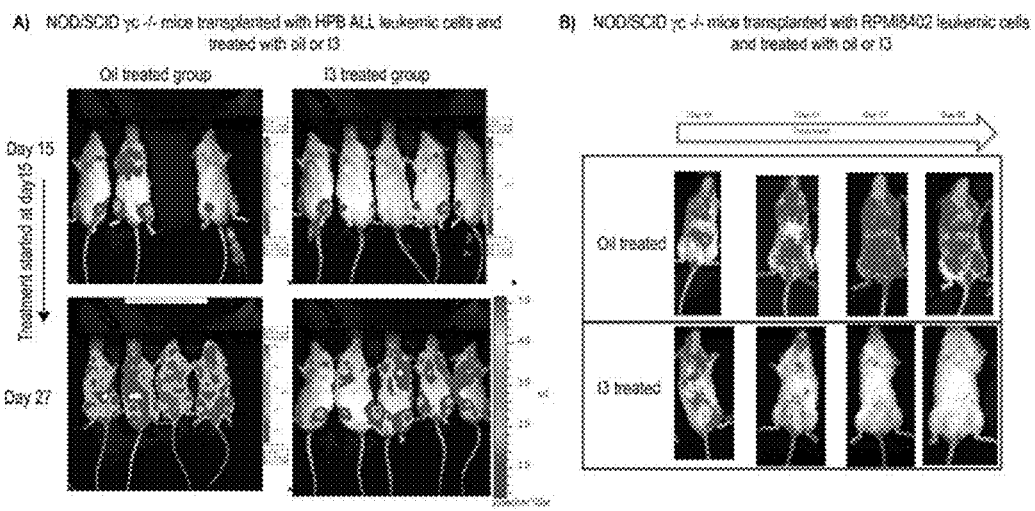
FIG. 8 shows 6-(4-Tert-Butylphenoxy)Pyridin-3-Amine (I3) treatment increases latency of leukemia development in mice. A) NOD/SCID γc$^{-/-}$ mice were injected with 1×10$^6$ HPB ALL (luciferase expressing) cells. On day 15, leukemic cells were established in the bone marrow. Mice were treated with oil or 6-(4-Tert-Butylphenoxy)Pyridin-3-Amine (I3) for every day. Mice were imaged on day 27 using Caliper IVIS (Xenogen) live imaging system. Red and blue colour indicates the intensity of luciferase signal and correlates with the number of leukemic cells. B) 6-(4-Tert-Butylphenoxy)Pyridin-3-Amine (I3) treatment blocks RPMI 8402 leukemic cell growth in xenotransplantation assay. NOD/

Anti-cancer activity of 6-(4-Tert-Butylphenoxy)Pyridin-3-Amine (I3) was investigated in transplant models for human diseases, namely T-cell leukemia and breast cancer. In these studies, 6-(4-Tert-Butylphenoxy)Pyridin-3-Amine (I3) has demonstrated a remarkable ability to slow down the progression and metastasis of very aggressive form of leukemic cell lines (FIG. 8). In addition, in a preliminary study using breast cancer as a model of solid tumors, 6-(4-Tert-Butylphenoxy)Pyridin-3-Amine (I3) treatment has led to a block in tumor progression in the mice (FIG. 9).

The chemical compound 6-(4-Tert-Butylphenoxy)Pyridin-3-Amine (I3) has shown ability to block NICD mediated signalling. Therefore this compound is useful in cancers where Notch driven tumors are resistant to γ-secretase inhibitor treatment.

The present invention also provides a pharmaceutical composition comprising 6-(4-Tert-Butylphenoxy)Pyridin-3-Amine (I3) of formula I, or one of its derivatives having Notch signalling pathway inhibition properties as described herein, or pharmaceutically acceptable salts, solvates, tautomers, isomers thereof, and a pharmaceutically acceptable carrier. As to the appropriate carriers, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002. The term "pharmaceutically acceptable carrier" means a carrier or excipient that is useful in preparing a pharmaceutical composition that is generally safe, and possesses acceptable toxicities. Acceptable carriers include those that are acceptable for veterinary use as well as human pharmaceutical use. A "pharmaceutically acceptable carrier" as used in the specification and claims includes both one and more than one such carrier. Optionally, the pharmaceutical composition of the present invention further comprises one or more additional active agents selected among the non limiting group comprising chemotherapeutic agents for treating cancer. Such chemotherapeutic agents may be selected among the group comprising, for example, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine and Vinorelbine.

The compounds of the invention, namely the 6-(4-Tert-Butylphenoxy)Pyridin-3-Amine (I3) and derivatives thereof, that are used in the treatment and/or prevention of cancers can be incorporated into a variety of formulations and medicaments for therapeutic administration. More particularly, one or more compound(s) as provided herein can be formulated into pharmaceutical compositions by combination with appropriate, pharmaceutically acceptable carriers, and can be formulated into preparations in solid, semi-solid, liquid or gaseous forms, such as tablets, capsules, pills, powders, granules, dragees, gels, slurries, ointments, solutions, suppositories, injections, inhalants and aerosols.

As such, administration of the compounds can be achieved in various ways, including oral, buccal, rectal, parenteral, intraperitoneal, intradermal, transdermal, intracranial and/or intratracheal administration. Moreover, the compound can be administered in a local rather than systemic manner, in a depot or sustained release formulation. The compounds can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. The compounds can be administered alone, in combination with each other, or they can be used in combination with other known compounds. Suitable formulations for use in the present invention are found in Remington's Pharmaceutical Sciences (Mack Publishing Company (1985) Philadelphia, Pa., 17th ed.), which is incorporated herein by reference. Moreover, for a brief review of methods for drug delivery, see, Langer, Science (1990) 249:1527-1533, which is incorporated herein by reference.

The amount of a compound as provided herein that can be combined with a carrier material to produce a single dosage form will vary depending upon the disease treated, the subject in need thereof, and the particular mode of administration. However, as a general guide, suitable unit doses for the compounds of the present invention can, for example, preferably contain between 0.1 mg to about 1000 mg, between 1 mg to about 500 mg, and between 1 mg to about 300 mg of the active compound. In another example, the unit dose is between 1 mg to about 100 mg. Such unit doses can be administered more than once a day, for example, 2, 3, 4, 5 or 6 times a day, but preferably 1 or 2 times per day, so that the total dosage for a 70 kg human adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area. A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release. It can be necessary to use dosages outside these ranges in some cases as will be apparent to those skilled in the art.

The present invention further provides a compound of the invention for use in treating and/or preventing cancers.

As used herein, cancers are preferably Notch dependent cancers and are selected from the non limiting group comprising T cell-Acute lymphoblastic leukemia (T-ALL), chronic myeloid leukemia (CML), chronic lymphocytic leukemia (CLL), Mantle cell lymphoma, breast cancer, pancreatic cancer, prostate cancer, melanoma, brain tumors, tumor angiogenesis, and colorectal cancer.

Preferably, the compounds of the present invention (6-(4-Tert-Butylphenoxy)Pyridin-3-Amine (I3), its derivatives) can be also used in the treatment of cancers where Notch dependent cancers are resistant to γ-secretase inhibitor treatment. Notch signalling dependent human tumors resistant to γ-secretase inhibitor treatment can be determined by the levels of NICD, Notch target genes as well as by mutation status of Notch receptor and other components of the Notch pathway.

The present invention also provides a method for treating and/or preventing cancers, said method comprising administering the 6-(4-Tert-Butylphenoxy)Pyridin-3-Amine (I3), its derivatives, or the pharmaceutical composition of the invention to a subject in need thereof.

In another embodiment, the present invention provides a method of treatment of a disease associated with an up-regulated Notch signalling pathway activity, said method comprising administrating the 6-(4-Tert-Butylphenoxy) Pyridin-3-Amine (I3), a derivative thereof, or the pharmaceutical composition of the invention to a subject in need thereof.

The daily dose of compounds of the present invention will necessarily be varied depending upon the host treated, the particular route of administration, and the severity and kind of the illness being treated. Accordingly the optimum dosage may be determined by the practitioner who is treating any particular patient. Further, it is noted that the clinician or treating physician will know how and when to start, interrupt, adjust, or terminate therapy in conjunction with individual patient response.

For any compound used in the method of the present invention, a therapeutically effective dose can be estimated initially from cell culture assays, animal models, or microdosing of human subjects.

"Treatment" as used herein, refers to both therapeutic treatment and prophylactic or preventative measures. Subjects in need of treatment include those already with the disorder, such as cancer, as well as those in which the disorder, such as cancer, is to be prevented. Hence, the mammal, preferably human, to be treated herein may have been diagnosed as having the disorder, such as cancer, or may be predisposed or susceptible to the disorder, such as cancer.

The term "therapeutically effective amount" refers to an amount of a drug effective to treat a disease or disorder in a mammal. In the case of cancer, the therapeutically effective amount of the drug may reduce the number of tumor or cancer cells, reduce the tumor size; inhibit (i.e., slow to some extent and preferably stop) cancer cells infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compounds of the present invention may prevent growth and/or kill existing cancer cells, it may be cytostatic and/or cytotoxic. The phrase "therapeutically effective amount" is used herein to mean an amount sufficient to prevent, or preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells, or other feature of pathology.

Optionally the compounds of the present invention may be used against cell proliferate diseases in combination (for example either at the same time, or almost at the same time, or one after the other) with conventional treatments such as standard radiotherapy and/or standard chemotherapy. The standard radiotherapy and chemotherapy can be also the concomitant chemo-radiotherapy.

Therefore, optionally, the standard radiotherapy and/or chemotherapy can be performed before, simultaneously or after the administration of a therapeutically effective amount of the compound of the present invention, or pharmaceutical compositions containing thereof.

The term "concomitant chemo-radiotherapy" is used when these two treatments (chemotherapy and radiotherapy) are given either at the same time, or almost at the same time, for instance one after the other, or on the same day, etc.

The term "standard radiotherapy" refers to the use of ionizing radiation as part of cancer treatment to control malignant cells. Preferably the ionizing radiation is γ-irradiation. It is also common to combine radiotherapy with surgery, chemotherapy, hormone therapy, or combinations thereof. Most common cancer types can be usually treated with radiotherapy. The precise treatment intent (curative, adjuvant, neoadjuvant or palliative) will depend on the tumor type, location, and stage, as well as the general health of the subject in need thereof.

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer include, for example, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine or Vinorelbine.

When a chemotherapeutic agent is used in combination with a compound according to the present invention, then this may be used in the form of a medicament containing a combination of these two agents, for simultaneous administration, or they may be used in the form of separate dosage forms, each containing one of the agents, and in the latter case the individual dosage forms may be used e.g. sequentially, i.e. one dosage form with the compound of the invention, followed by a dosage form containing the chemotherapeutic agent (or vice versa). This embodiment of two separate dosage forms may be conceived and provided in the form of a kit.

Also optionally the compounds of the present invention may be used against cell proliferate diseases, such as cancers, in combination with conventional removal of a tumor bulk, by for example segmental resection (biopsy or gross resection).

The term "removal of a tumor bulk" refers to any removal, ablation or resection of a tumor bulk from a subject. The removal can be chemical, radiation or surgical. Preferably said removal is surgical, such as ablation or resection. Resection can be "segmental resection" (or segmentectomy), a surgical procedure to remove part of an organ or gland from a subject. It may also be used to remove a tumor and normal tissue around it. Debulking agent may be also used to remove tumor bulk. The term "debulking agent" includes any molecule (e.g. chemical, biological) or any external/environmental agent (e.g. γ-irradiation) or traditional surgery that would allow killing cancer cells from the tumor bulk (e.g. FL1$^0$ and FLY$^-$ cells as mentioned above).

Another object of the present invention is a kit comprising one or more doses of 6-(4-Tert-Butylphenoxy)Pyridin-3-Amine (I3), or of one of its derivatives having Notch signalling pathway inhibition properties, or the pharmaceutical composition of the present invention for use in a method for treatment and/or prevention of cancers. The kit can further comprise one or more doses of a chemotherapeutic agent. Optionally, the kit may also comprise reagents and/or instructions for use.

Generally, the kit comprises a container and a label or package insert on or associated with the container. Suitable containers include, for example, bottles, vials, syringes, etc. The containers may be formed from a variety of materials such as glass or plastic. The container holds the pharmaceutical composition that is effective for treating the condition and may have a sterile access port (for example the container may be an intravenous solution bag or a vial having a stopper pierceable by a hypodermic injection needle). The label or package insert indicates that the composition is used for treating the condition of choice, such as cancer.

The present invention also relates to the use of the compounds of the invention for inhibiting in vitro or in vivo the Notch signalling pathway in cells. Usually, said cells are cancer cells.

Also envisioned is a method of treating a subject for Notch dependent cancer, comprising
i) determining in cancer cells obtained from a biological sample of said subject whether the cancer is Notch signalling pathway dependent, ii) and treating said subject based upon whether the cancer is Notch dependent cancer by administering a therapeutically effective amount of 6-(4-Tert-Butylphenoxy)Pyridin-3-Amine (I3) of Formula I or one of its derivatives having Notch signalling pathway inhibition properties, or a pharmaceutical composition of the invention.

Usually, the Notch signalling pathway dependency in cancer cells is determined by any method known in the art. As an example, this method can consist in an in vitro γ-secretase complex activity assays as described herein.

This method of treating may further comprise administering at least one conventional cancer treatment. The conventional cancer treatment is administered before, simultaneously or after the administration of the therapeutically effective amount of 6-(4-Tert-Butylphenoxy)Pyridin-3-Amine (I3) of Formula I or one of its derivatives having Notch signalling pathway inhibition properties, or the pharmaceutical composition of the invention.

Usually, the conventional cancer treatment consists in radiotherapy and/or chemotherapy.

The present invention also relates to the use of the compounds of the invention in a method for provoking apoptosis in a cell, either in vitro or in vivo, by inducing G0/G1 cell cycle arrest.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Constructs and Gene Reporter Assays

Mouse DL4-IRES dsRED cDNA was cloned into a pENTR1 vector (Invitrogen®) and finally shuttled into a destination lentivirus vector using Gateway cloning strategy (Invitrogen). A Phosphoglycerate kinase (PGK) promoter drove the expression of DL4 protein. DL4-lentiviral particles were produced in 293T cells by cotransfection of DL4-lentivirus vector, Gag/pol expression plasmid and plasmid encoding for viral envelope proteins. To overexpress Notch1 protein, mouse full length Notch1 cDNA was a cloned in a pCDNA3.1-IRES-puromycin vector. Notch1 cDNA was cloned upstream of IRES-puromycin between HindIII and XbaI restriction sites. A CMV promoter controlled the expression of Notch1 protein.

To measure the Notch signalling activation, CSL/RBP-jk consensus DNA binding sequences were cloned in a head to tail conformation in the pGL4 luciferase vector (Promega), thus named 12×CSL/RBP-jjk luciferase vector. In order to determine the Notch pathway activation in chemical compound screening assay, 12×CSL/RBP-jk consensus DNA binding sequences were cloned into pGL4.26.luciferase vector (Promega). As an internal control for transfection efficiency, SV40 Renilla vector was used (Promega).

NICD-GFP overexpression studies were performed using pEGFP-C1-NICD expression plasmid. The FLAG-CMV2 plasmid expressing MAML1-FLAG was a kind gift from Dr. Lizi Wu, Harvard Medical School, Boston.

Generation of DL4 and N1 Stable HeLa Cells:

In order to generate DL4 and N1 stable cell lines, HeLa cell were bought from ATCC (catalog # CCL-2). To generate DL4 stable lines, cells were transduced with DL4-lentiviral particles. DL4 stable clones were selected using puromycin. High DL4 expressing clones were sorted using antibodies against DL4 with Fluorescence activated cell sorting (FACS). To generate N1 stable line, cell were transfected with a pCDNA3.1+(Invitrogen) plasmid containing mouse full length Notch1 under the control of CMV promoter. To select for Notch1 expressing clones, an IRES puromycin cassette was cloned downstream of Notch1 cDNA. HeLa cells expressing high levels of Notch1 were enriched by FACS using anti-Notch1 antibodies. DL4- and N1-HeLa cells were cultured in DMEM (GIBCO, Invitrogen), 10% FCS and 10 ug/ml of puromycin (Sigma).

High-Throughput Screening and Data Analyses:

For chemical library screen, the coculture assay was performed as follows. N1-HeLa cells were cotransfected in 10 cm tissue culture dishes with 16 µg of pGL4.26.12× CSL.luciferase vector/plate, 4 µg of Notch1 expression plasmid/plate, and 200 ng of SV40 Renilla vector/plate. DL4- and N1-HeLa cells were detached from the plate by using 0.5 mM EDTA (1×PBS). The both cell populations were counted and mixed in 1:1 ratio (5,000:5,000 cells/well in a 384 well plate) and dispensed into 384 well plates (white, clear bottom, Corning) using multidrop Combi plate dispenser. The assay plates were pre-dispensed (using automated Biomek 3000 liquid handler) with chemical compound libraries (Microsource NIMDS, Maybridge Hitfinder and Prestwick) to give a final concentration of 10 µM. The final assay volume was 22 pls. Twenty-four hours later, growth media was aspirated and cells were lysed with 1× Passive lysis buffer for 10 minutes at room temperature. Luciferase activity was measured using Luciferase Assay Reagent II and Renilla values were determined by using Stop and Glow reagent (Dual luciferase assay system, Cat # E1980, Promega). Luciferase and renilla readouts were taken using Tecan® F500 (Tecan) multiplate reader. All the liquid handling steps (aspiration of the medium, dispensing of Passive lysis buffer, Luciferase Assay Reagent II and Stop and Glow reagents) were performed using ELF406 liquid handler.

Data analyses were performed using in-house built analyses software at Biomolecular Screening Facility (BSF) at Ecole Polytechnique Federale de Lausanne (EPFL).

RNA Extraction

Total RNA was extracted from cells using TRIzol® extraction kit (Invitrogen). Briefly, $1 \times 10^6$ cells were washed with ice-cold 1×PBS and lysed in 1 ml of TRIzol® solution for 5 minutes at room temperature to dissociate nucleoprotein complexes. Lysed cells were then treated with 200 µl of chloroform and shaked vigorously for 15-30 seconds and incubated at room temperature for 2-3 minutes. The samples were centrifuged at 14000 rpm using Eppendorf table top centrifuge for 10 minutes at 4° C. Following centrifugation, upper aqueous phase was transferred to new eppendorf tubes. To precipitate total RNA 500 µl of isomyl alcohol was added to the separated aqueous phase and incubated at room temperature for 10 minutes. A RNA pellet was obtained by centrifuging the samples at 4° C. for 10 minutes. RNA pellet obtained was washed with 1 ml ice cold 75% ethanol and spun down at 14000 rpm at 4° C. RNA pellet was dried off of excess of ethanol and resuspended in 40 µl DPEC water.

cDNA Synthesis:

Total RNA extracted from the cell was used to synthesize cDNA by reverse transcription reaction. Reverse transcription was performed using SuperScript™ RT (Invitrogen). RNA concentration was measured using NanoDrop® ND-1000 spectrophotometer (Witec AG) and 500 ng of total RNA was mixed with a 10 mM mix of dNTPs and 100 ng of random primers. The reaction mix was incubated at 65° C. for 5 minutes and quickly incubated on ice for 1 minute. Following incubation on ice, 5× first strand buffer and 0.1M DTT were added and mix was incubated for 2 minutes at 25° C. To start the reverse transcription reaction, 200 U of SuperScrip™ II RT was added to the reaction mix and incubated at 42° C. for 50 minutes. The reaction was stopped by incubating the reaction mix at 75° C. for 15 minutes.

Western Blot Analyses:

Cells were lysed in RIPA buffer (50 mM Tris.Cl, pH 7.5, 150 mM NaCl, 1% nonidet P-40, 0.5% sodium deoxycholate and 0.1% SDS) for 30 minutes at 4° C. Lysed cells were centrifuged to remove the debris at 14000 rpm at 4° C. Supernatant was transferred to a new eppendorf tube. The protein concentration was determined by Bradford assay using spectrophotometer (Ultrospec 3000 pro). 40 µg of protein were denatured in 1×SDS gel loading buffer (100 mM Tris.Cl, pH 6.8, 200 mM DTT, 4% SDS, 0.2% bromophenol, 20% glycerol) by heating at 99° C. for 5 minutes.

Denatured protein samples were stored on ice until loading on to the acrylamide gel. The samples were run on 8% or 10% acrylamide gel in Tris-glycine electrophoresis buffer (25 mM Tris, 250 mM glycine, 0.1% SDS). Following separation on the acrylamide gel, protein samples were transferred on to PVDF membrane (PEQ lab, catalog number 39-3010) using transfer buffer (39 mM glycine, 48 mM Tris base, 0.037% SDS and 20% methanol).

For immunoblotting, membranes were blocked with 5% milk and incubated overnight with primary antibodies at 4° C. Membrane were washed with 1×TBST (1×TBS+0.5% tween 20) for 5 minutes (3 times) and incubated with HRP-conjugated secondary antibodies for one hour at room temperature. Signal was detected with Super Signal West chemiluminescent substrate (Thermo Scientific, catalog number 34077).

Immunofluorescence Staining:

To perform immunofluorescence staining, HeLa cells or C2C12 cells were grown on cover slips. Cells were washed with 1× ice-cold PBS, fixed with 4% PFA for 5 minutes at room temperature and permeabilized using 0.3% Triton X-100. Subsequently permeabilized cells were blocked for 20 minutes with 1% BSA for 20 minutes at room temperature. Cells were incubated with appropriate primary antibodies for one at room temperature. Alexa Fluor-488 conjugated secondary antibodies were used to detect primary antibodies. Cells were counterstained with DAPI and mounted in fluorescent mounting media. Fluorescent images were viewed and captured using Zeiss Axioplan microscope at Bioimaging and optics core facility at EPFL.

was performed using anti-MHC antibody as explained in the section 2.2.6 (Immunofluorescence staining).

Flow Cytometry Analyses:

Fluorescence activated cell sorting (FACS) analyses were performed on CyAn™ ADP instrument platform for flow cytometry at Flow cytometry core facility, EPFL. DL4 and Notch1 expression in DL4- and N1-HeLa cells was determined using anti-DL4 and anti-N1 antibodies respectively. T cell development in the thymus was investigated using antibodies against CD4, CD8 and TCRβ. MZB cell development was monitored using antibodies against B220, CD21 and CD23. In brief, a single cell suspension was prepared from thymus and spleen. $1 \times 10^6$ cells suspended in 50 µl of staining media (HBSS supplemented with 2% NCS and 25 mM HEPES) and stained with appropriate antibody combinations by incubating on ice for 30 minutes.

To quantitate the percentage of apoptotic cells, AnnexinV and 7AAD staining was performed. Thymic cells were suspended in 300 µl of 1× AnnexinV binding buffer (BD Biosciences, San Diego, USA) and incubated with 10 µl of AnnexinV-Cy5 antibody and 10 µl of 7AAD (BD Biosciences, San Diego, USA). Samples were incubated for 15 minutes at room temperature. FACS was performed with in one hour of antibody staining.

Flow cytometry analyses were done on live cells by gating on forward scatter (FSC) and side scatter (SSC). Data were analyzed by FlowJo software (Tree Star, Ashland, Oreg.).

Alamar Blue Proliferation Assay:

Alamarblue® proliferation assays were performed to determine the growth kinetics of Notch inhibitor treated

TABLE 1

List of the antibodies and working dilutions.

| Antibodies | Application | Dilution | Source |
| --- | --- | --- | --- |
| Anti-Val 1744 NICD | WB and ChIP | 1:1000 | Cell Signal, 2421S |
| Anti-Notch1 (C-20) | WB | 1:1000 | Santa Cruz, sc-6014 |
| Anti-RBP-jk | IF | 1:500 | Santa Cruz, sc-28713 |
| Anti-FLAG-M2 | IF | 1:500 | Sigma, F1804 |
| Anti-Hes1 (H-140) | WB | 1:500 | Santa Cruz, sc-25392 |
| Anti-cMyc (9E10) | WB | 1:500 | Abcam, ab11917 |
| Anti-Delta like 4 | Flow cytometry | 1:100 | Produced in-house |
| Anti-Notch1 | Flow cytometry | 1:50 | Produced in-house |
| Anti-Tubulin | WB | 1:3000 | Sigma, |
| Anti-Myosin heavy chain | IF | 1:200 | Sigma, MY-32 |
| HRP-conjugated anti-goat IgG | WB | 1:3000 | Invitrogen, 611620 |
| HRP-conjugated anti-mouse IgG | WB | 1:3000 | GEhealthcare, NA931V |
| HRP-conjugated anti-rabbit IgG | WB | 1:3000 | GEhealthcare, NA934V |
| Alexa Fluor-488 secondary Ab | IF | 1:1000 | Invitrogen |
| Anti-B220-Pacific blue | Flow cytometry | 1:400 | Produced in-house |
| Anti-CD21-FITC | Flow cytometry | 1:200 | eBioscience |
| Anti-CD23-PE | Flow cytometry | 1:400 | BD Pharmingen |
| Anti-TCR β-APC eF780 | Flow cytometry | 1:400 | eBioscience |
| Anti-CD4-FITC | Flow cytometry | 1:800 | Produced in-house |
| Anti-CD8-Alexa 648 | Flow cytometry | 1:600 | Produced in-house |
| Anti-CD71-PE | Flow cytometry | 1:800 | eBioscience |
| Anti-Ter119-APC eF780 | Flow cytometry | 1:200 | eBioscience |
| Anti-AnnexinV-Cy5 | Flow cytometry | 1:50 | BD Pharmingen |

C2C12 Myoblast Differentiation Assay:

C2C12 cells were grown on collagen-coated cover slip in the presence of growth media (10% serum). To induce myoblast differentiation, cells were grown to 100% confluency for 3 days in the presence of differentiation media (2% horse serum) or in the presence of growth media+Notch inhibitors. After 3 days, cells were washed with 1× ice-cold PBS and fixed with 4% PFA. Immunofluorescence staining cells. Alamar Blue® consists of a cell permeable substrate resazurin. In metabolically active and proliferating cells, resazurin is converted to resorufin due to an intrinsic reducing power of live cells and produces a red fluorescence. Therefore production of resorufin serves as an indicator of the viability of the cell population.

Proliferation assays were performed by seeding 5000 cells/well in a 96 well plate. Cells were treated with DMSO or Notch inhibitors for different time intervals. Each treatment for every time interval was carried out in 8 replicates. To determine the growth kinetics, 10 μl of Alamar Blue® (Invitrogen) was added to each well and incubated for 4 hours. Alamarblue readout was taken using Tecan F500 (Tecan) multiplate reader.

Haematoxylin & Eosin Staining:

Organs were harvested, fixed in 4% paraformaldehyde (PFA) overnight at 4° C. and embedded in paraffin. Tissue sections were dewaxed and hydrated using decreasing concentration of ethanol (100%-70%) and finally in distilled water. Sections were stained with Hemotoxylin for 5 minutes, rinsed in acid alcohol for about 20 seconds and then rinsed in running water for 10 minutes. Sections were then stained with Eosin for 5 minutes, washed in water and dehydrated using increasing concentration of ethanol (70%-100%) and cleared in xylene solution. Sections were the mounted using mounting solution. Haematoxylin and Eosin stained sections were viewed and images were captured using Leica DMI4000 microscope.

Alcian Blue Staining:

Intestinal tissue was flushed with ice-cold 1×PBS, fixed in 4% PFA. Tissues were embedded in paraffin and sectioned to a thickness of 4 microns. Intestinal sections were deparaffinized at 60° C. and hydrated with decreasing concentration of alcohol (100%-70%) and finally washed in distilled water. Alcian blue staining was performed for 30 minutes at room temperature washed in running water and finally counterstained in nuclear fast red solution for 5 minutes. Tissue sections were then washed in running water dehydrated in 100% alcohol and cleared in xylene solution. Mounted sections were then viewed and images were captured using Leica DMI4000 microscope.

Experimental Mice:

Mice were kept and bred at Animal facility, EPFL, Lausanne. C57B16 mice were used to assess the intestinal toxicity of the chemical compounds. MMTV-ErbB2/Neu-IRES Cre (FVB background) mice were obtained from Dr. William J Muller, McGill University, Montreal and genotyped using MIVITV-ErbB2/Neu specific primers (Ursini-Siegel et al., 2008). NOD/SCIDγc$^{-/-}$ mice were bought from The Jackson Laboratory (USA) and were kept and bred at Animal facility, EPFL, Lausanne.

Intestinal Toxicity and Effect on Marginal Zone B Cell Development:

C57B16 mice were intra peritoneal (i.p) injected with oil or 25 mg/kg of I3 or 10 mg/kg of CPA, once a day for 5-7 days. Mice were weighed using a weighing scale on day 0, day 3 and day 5. On day 8, intestinal tissue, spleen and thymus were harvested for analyses.

Tumor Transplantation Assay:

The human leukemic cell lines RPMI 8402 and HPB ALL were transduced with a lentivirus containing luciferase gene constitutively expressed downstream of a CMV promoter. The human leukemic cell lines RPMI 8204 (0.5-1×10$^6$ cells) and HPB ALL (1×10$^6$) were suspended in 100 μl of ice-cold 1×PBS and kept on ice until the transplant. NOD/SCIDγc$^{-/-}$ mice were transplanted with the human leukemic cell lines by intravenous (i.v) injection. Mice were monitored for tumor development using Caliper IVIS (Xenogen) live imaging system. Briefly, the luciferase substrate luciferin (Biosynth, L-8820) was dissolved in 1×PBS and was injected (intra peritoneal) into the mice at a concentration of 150 mg/kg of body weight. Mice were imaged 5 minutes after the luciferin injection using Caliper IVIS live imaging system.

At day 13-15, mice were treated with oil or 25 mg/kg of I3 on a daily basis. Images were captured at the end of the experiments.

Primary MMTV-ErbB2/Neu mammary tumors were harvested from the mice and a single cell suspension was prepared. 1×10$^6$ primary tumor cells were suspended in 50 μl of 1×PBS and kept on ice. Three weeks old recipient FVB mice were cleared of their endogenous epithelium and tumor cells were injected into the empty fat pad. Tumor development in the recipient mice was monitored and tumor volumes were measured using digital caliper. Tumor volumes were calculated using following formula: 2×length×(width). Once the tumor reached a volume of about 100 mm$^3$, recipient mice were treated with oil or 25 mg/kg of I3 on alternate days.

Assay Development

In order to identify novel modulators of the Notch pathway, Applicants have established a coculture assay in which DL4 ligand expressing HeLa cells were cultured with N1 HeLa cells, thereby activating the Notch pathway. The use of a DL4 and N1 HeLa cell coculture system mimics physiological conditions of cell-cell communication between ligand and receptor expressing cells. The in vitro generation of a controlled receptor-ligand assay system allowed Applicants to modify and monitor the Notch signal intensity by γ-secretase inhibitors.

DL4: N1 HeLa Cell Coculture Activates Notch Signalling

To set up a coculture assay, Applicants have established DL4 and N1 expressing stable HeLa cell lines. In brief, HeLa cells were transduced with a lentivirus containing DL4 cDNA downstream of the PGK promoter. The D4 expressing cell population was enriched by fluorescence activated cell sorting. Similarly, the N1 stable HeLa cell line was established using a plasmid containing the mouse N1 cDNA followed by an IRES Puromycin selection cassette. This system allowed Applicants to select for only Notch1 expressing clones when selected using puromycin. The expression levels of DL4 and N1 proteins in the respective cell lines were detected using anti-DL4 and anti-N1 antibodies. Quantification of the protein levels by flow cytometry showed high level expression of DL4 and N1 compared to parental HeLa cells (data not shown).

To assess the Notch pathway activation potential of the stable cell lines, DL4 and N1 stable HeLa cells (DL4-HeLa and N1-HeLa, respectively) were cocultured in 1:1 ratio in a 6-well plate and grown to confluency. The cocultured cells were treated with DMSO or DAPT (10 μM) for 24 hours. For comparison, parental HeLa cells were also cocultured with DL4-HeLa cells and were grown in the presence or absence of DAPT for 24 hours. Western blot analyses for the active form of Notch1 (NICD) using VAL1744 antibodies was performed and revealed only modest levels of NICD when parental HeLa cells were cocultured with DL4 HeLa cells (data not shown), accounting for a low level of endogenous Notch1 in HeLa cells. On the other hand, in the absence of ligand (DL4-HeLa cells) or in the presence of GSI (DAPT) NICD levels were not detected, indicating a loss of Notch signalling (data not shown). However, cocultures of DL4- and N1-HeLa cells revealed significantly higher levels of NICD, which can be blocked by DAPT treatment (data not shown). Transient introduction of full length Notch1 cDNA into N1-HeLa cells further enhanced the robustness of the coculture assay as indicated by the increased levels of NICD protein (data not shown). Inhibiting the N1 cleavage with DAPT can abrogate the increase in Notch signalling activity (data not shown). These results confirmed that high levels of the Notch pathway activation could be achieved in the DL4:N1 coculture assay that responds to GSI inhibition.

The establishment of DL4:N1 coculture assay in a 6 well plate format allowed Applicants to assess receptor-ligand interaction mediated Notch signalling activation. GSI (DAPT) treatment of the coculture system can block receptor-ligand interaction driven Notch signalling.

Establishment of High-Through Put Screening (HTS) Compatible Assay

Initially, DL4:N1 coculture assay was established in a 6-well plate. In order to set up a high-through put screen (HTS), the assay system was further optimized to robustly work in a 384 well plate format.

The assay was scaled-down to a 384 well plate format for screening of chemical compound libraries. In order to accomplish this, N1-HeLa cells were transfected with a reporter plasmids and N1 expression vector. Twelve hours later, chemical compounds were dispensed into a 384 well plate along with DMSO and DAPT as negative and positive controls. DL4- and N1-HeLa cells were mixed in a 1:1 ratio (5000:5000 cells/well) and added to 384 well plates using multidropCombi plate dispenser. Luciferase readout was measured using dual luciferase assay system. To optimize and determine the reproducibility of the assay, half of the plate was treated with DMSO (192 wells) and the second half was treated with 10 DAPT (192 wells). DAPT treatment led to a 10-fold downregulation of Notch signalling activation. The Z' value for this assay was higher than 0.5. A Z' value of >0.5 confirms the reliability and reproducibility of the assays for a HTS campaign.

Example 2

6-(4-Tert-Butylphenoxy)Pyridin-3-Amine (I3) as a Novel Notch Signalling Inhibitor I3 Inhibits NICD Mediated Activation of Notch Signalling:

To validate the Notch inhibitory activity and determine the IC50 value of the I3 compound, the DL4:N1 coculture assay system was used. The cells in the coculture assay were treated for 24 hours with an increasing concentration of I3 (2-10 µM). The activation of the Notch pathway was measured using a Notch driven luciferase reporter assay. As shown in FIG. 1A, I3 blocks Notch signalling in a concentration dependent manner with an IC50 value in the lower µM range.

To determine whether over expression of NICD can rescue I3 mediated inhibition of Notch signalling, HeLa cells were co-transfected with a NICD expression plasmid and 12×CSL luciferase construct. The transfected cells were treated with an increasing concentration of I3 and DAPT. Surprisingly, treatment of NICD expressing cells with I3 could block pathway activation in a dose-dependent manner, while DAPT had no effect on the signalling activation (FIG. 1B). This data suggests that I3 mediated inhibition of the Notch pathway is due to its activity downstream of the S3 cleavage event.

Next Applicants investigated whether I3 could block pathway activation via other Notch receptors or is it specific to Notch1 signalling. To address this, a coculture assay was used where Notch signalling was activated via DL4:N1 or DL4:N2 ligand receptor pairs. The treatment of cells in these two coculture assays with I3 caused an inhibition of Notch signalling via both DL4:N1 and DL4:N2 ligand-receptor pairs (FIG. 1C). Similarly, I3 could also block pathway activation by Notch1-intracellular domain (NICD) and Notch2-intracellular domain (N2-ICD), suggesting that I3 is not specific for NICD mediated activation (FIG. 1D).

6-(4-Tert-Butylphenoxy)Pyridin-3-Amine does not Block Nuclear Localization of NICD In vitro data from NICD transfected HeLa cells suggested that 6-(4-Tert-Butylphenoxy)Pyridin-3-Amine (I3) blocks Notch signalling by acting downstream of S3 cleavage event. This raises several possibilities about the mechanism of action of 6-(4-Tert-Butylphenoxy)Pyridin-3-Amine (I3). For example, 6-(4-Tert-Butylphenoxy)Pyridin-3-Amine (I3) treatment could impair nuclear localization of the NICD. A second possible mechanism of inhibition could be targeting of one or more individual components of the transcriptional activation complex in the nucleus. To test whether 6-(4-Tert-Butylphenoxy)Pyridin-3-Amine (I3) has an impact on nuclear transport of NICD, HeLa cell were transfected with a NICD-GFP fusion construct and treated with DMSO and 6-(4-Tert-Butylphenoxy)Pyridin-3-Amine (I3). This allowed Applicants to follow transport of fusion protein within the cell. In parallel, the 6-(4-Tert-Butylphenoxy) Pyridin-3-Amine (I3) mediated pathway inhibition was determined by Notch driven luciferase measurement (data not shown). Microscopic studies showed that in DMSO treated cells NICD-GFP fusion protein translocate to the nucleus, which was not perturbed upon 6-(4-Tert-Butylphenoxy)Pyridin-3-Amine (I3) treatment (data not shown). This data rule out nuclear exclusion of NICD as a mechanism of action of 16-(4-Tert-Butylphenoxy)Pyridin-3-Amine (I3).

Over Expression of MAML1 Above a Certain Threshold can Rescue 6-(4-Tert-Butylphenoxy)Pyridin-3-Amine (I3) Induced Notch Signalling Inhibition:

As 6-(4-Tert-Butylphenoxy)Pyridin-3-Amine (I3) mediated blockage of Notch signalling does not involve nuclear exclusion of NICD, Applicants addressed whether 6-(4-Tert-Butylphenoxy)Pyridin-3-Amine (I3) blocks interaction and thereby sub-nuclear localization of NICD, MAML1 and CSL-RBP-jk (all parts of the core transcriptional activation complex). To resolve this, HeLa cells were co-transfected with 800 ng of NICD-GFP plasmid, 1 µg of MAML1-FLAG expression vector and grown on cover slips. The transfected HeLa cells were treated with DMSO or 6-(4-Tert-Butylphenoxy)Pyridin-3-Amine (I3) (10 µM) for 24 hours. The ability of 6-(4-Tert-Butylphenoxy)Pyridin-3-Amine (I3) to block Notch activation at this concentration of NICD and MAML1 was verified by Notch driven luciferase measurement (data not shown). Following treatment, the cells were fixed with 4% PFA, blocked with 1% BSA and stained with antibodies against FLAG tagged MAML1 and CSL-RBP-jk. NICD-GFP fusion protein was visualized by tracing the GFP protein. When expressed alone, NICD-GFP protein was localized in the nucleus in a diffused manner and 6-(4-Tert-Butylphenoxy)Pyridin-3-Amine (I3) treatment did not alter its nuclear localization. However overexpression of NICD-GFP and MAML1 led to co-localization of both proteins into sub-nuclear compartments (possibly nuclear bodies). The 6-(4-Tert-Butylphenoxy)Pyridin-3-Amine (I3) treatment of the cells did not perturb the translocation and co-localization of NICD-GFP and MAML1 into sub-nuclear compartment (data not shown).

Similarly, the location of CSL/RBP-jk was investigated using antibodies specific against this protein. As shown in FIG. 22C, MAML1-FLAG and CSL/RBP-jk co-localized in sub-nuclear compartments and 6-(4-Tert-Butylphenoxy) Pyridin-3-Amine (I3) treatment did not perturb their distribution in the nucleus (data not shown). This data suggest that 6-(4-Tert-Butylphenoxy)Pyridin-3-Amine (I3) treatment does not perturb co-localization of components of the Notch transcriptional activation complex in the nucleus. However, whether it blocks interaction between various components of the complex still need to be investigated.

To further investigate the mechanism of action of 6-(4-Tert-Butylphenoxy)Pyridin-3-Amine (I3), Applicants speculated that 6-(4-Tert-Butylphenoxy)Pyridin-3-Amine (I3) might be targeting one of the components of the transcriptional activation complex. The over expression of this target protein may titrate out 6-(4-Tert-Butylphenoxy)Pyridin-3-Amine (I3) compound and thus rescue 6-(4-Tert-Butylphenoxy)Pyridin-3-Amine (I3) induced pathway inhibition. To address this question, HeLa cells were co-transfected with 800 ng of NICD-GFP plasmid and with an increasing amount (0, 1 and 3 μg) of MAML1-FLAG expression vector. The Notch pathway activation was measured by introducing 12×CSL luciferase plasmid. As shown in FIG. 2, in HeLa cells transfected with NICD alone or NICD+1 μg of MAML1, 6-(4-Tert-Butylphenoxy)Pyridin-3-Amine (I3) treatment can block Notch signalling in a concentration dependent manner. However, when the amount of MAML1 plasmid was increased to 3 μg, 6-(4-Tert-Butylphenoxy) Pyridin-3-Amine (I3) treatment was no longer able to inhibit the activation of Notch signalling (FIG. 2). Therefore, over expression of MAML1 above a certain threshold could rescue 6-(4-Tert-Butylphenoxy)Pyridin-3-Amine (I3) mediated inhibition of the Notch pathway. This data suggest that MAML1 itself might be the target of 6-(4-Tert-Butylphenoxy)Pyridin-3-Amine (I3) compound. An increase in the concentration of MAML1 may be able to titrate out the inhibitor and thus rendering it incapable of blocking the signalling cascade.

Figure 3:
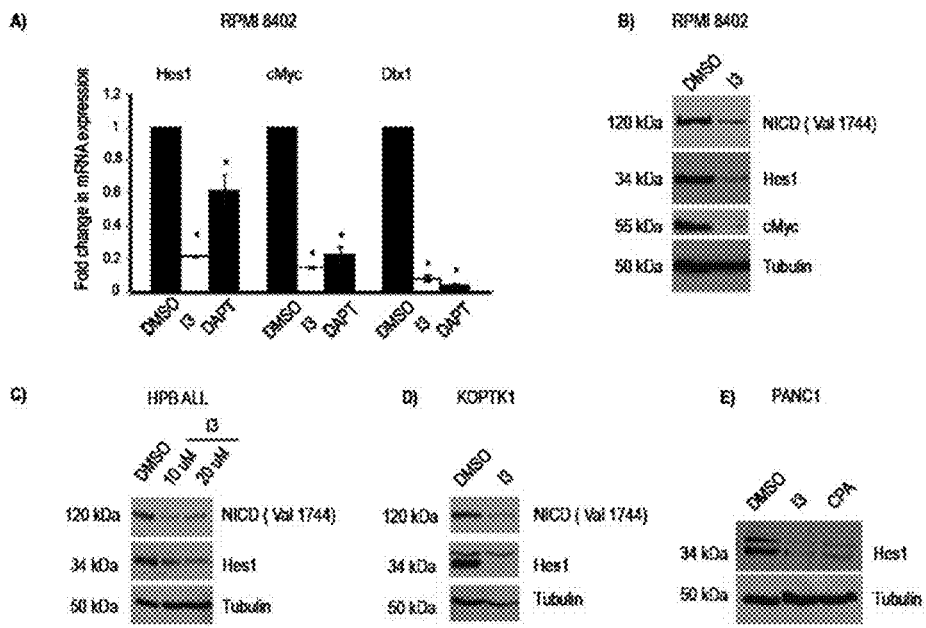
FIG. 3 shows 6-(4-Tert-Butylphenoxy)Pyridin-3-Amine (I3) inhibits Notch signalling and downregulates its target genes in human cancer cell lines. A) RPMI 8402 cells were treated with DMSO, 6-(4-Tert-Butylphenoxy)Pyridin-3-Amine (I3) and DAPT (10 μM) for 24 hours and analyzed for the expression of Notch target genes, Hes1, cMyc and Dtx1 by qRT-PCR. Data normalized to HPRT as a housekeeping gene. B) Whole cell lysate from 6-(4-Tert-Butylphenoxy)Pyridin-3-Amine (I3) treated cells was analyzed by Western blot. Using antibodies against NICD (Val1744), Hes1 and cMyc, the protein levels of NICD and Notch target genes were determined. C and D) The human T-ALL cell lines HPB ALL and KOPTK1 were treated with DMSO or 6-(4-Tert-Butylphenoxy)Pyridin-3-Amine (I3) for 24 hours. Western blot analyses were performed using NICD (Val1744) and Hes1 specific antibodies. Tubulin served as a loading control. E) Whole cell lysate from DMSO, 6-(4-Tert-Butylphenoxy)Pyridin-3-Amine (I3) treated PANC1 cells (pancreatic cancer cell line) were analyzed by Western blot. Hes1 protein levels were determined using Hes1 specific antibodies. Statistical analyses were done using student's two-tailed t.test. *=p value <0.05.

6-(4-Tert-Butylphenoxy)Pyridin-3-Amine (I3) Treatment Decreases Notch Signalling in Human Cancer Cell Lines Aberrant activation of Notch signalling plays an important role in tumor initiation and/or maintenance of human cancers. To determine whether 6-(4-Tert-Butylphenoxy) Pyridin-3-Amine (I3) treatment can block Notch signalling in human cancer cells, various cancer cell lines (T-ALL cell lines RPMI 8402, HPBALL, KOPTK1 and pancreatic cancer cell line PANC1) were treated with 6-(4-Tert-Butylphenoxy)Pyridin-3-Amine (I3) for 24 hours. The effect on Notch signalling was determined by measuring the expression levels of Notch target genes. 6-(4-Tert-Butylphenoxy)Pyridin-3-Amine (I3) treatment of human cancer cell lines (RPMI 8402, HPBALL, KOPTK1 and PANC1) for 24 hours and subsequent analyses of Notch target genes by qRT-PCR or Western blot analyses showed that 6-(4-Tert-Butylphenoxy)Pyridin-3-Amine (I3) induced a statistically significant downregulation of Notch target genes such as Hes1, cMyc and Dtx1 at the mRNA as well as at the protein levels (FIG. 3). The downregulation of Notch target genes correlates with reduced levels of NICD (FIGS. 3B, C and D).

Figure 4:
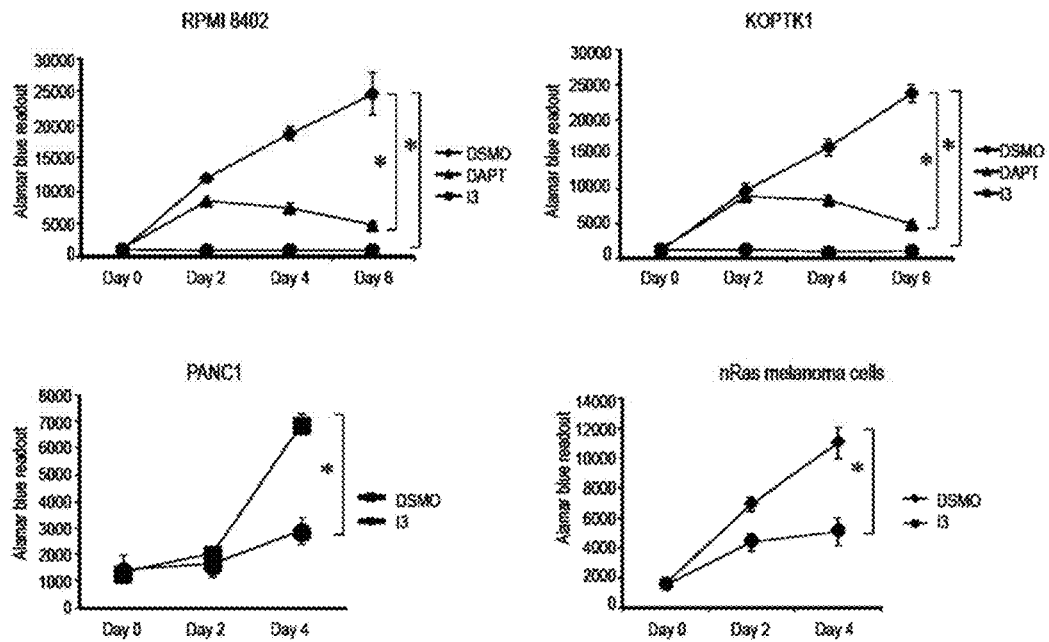
FIG. 4 shows 6-(4-Tert-Butylphenoxy)Pyridin-3-Amine (I3) induces a proliferative block in human cancer cells. Human T-ALL cell lines RPMI 8402 and KOPTK1, and pancreatic cancer cell line PANC1 as well as nRas driven melanoma cells were seeded in a 96 well plate and treated with 10 μM concentration of 6-(4-Tert-Butylphenoxy)Pyridin-3-Amine (I3) and DAPT for several days. Their growth inhibitory effects were compared with cells treated with equal amount of DMSO. Using Alamar blue assay, the growth kinetics of RPMI 8402 and KOPTK1 were followed for upto 6 days, while PANC1 and nRas melanoma cells were monitored for 4 days. 6-(4-Tert-Butylphenoxy)Pyridin-3-Amine (I3) treatment of RPMI 8402, KOPTK1. PANC1 and nRas melanoma cells caused a significant reduction in their growth potential. Statistical analyses were done using student's t.test. *=p value<0.05. ns=not significant.

As treatment of the human T-ALL cell lines and PANC1 pancreatic cancer cell line with 6-(4-Tert-Butylphenoxy) Pyridin-3-Amine (I3) induced a downregulation of Notch signalling, Applicants questioned whether this inhibition of the pathway translates into growth arrest in cancer cells. To this end, RPMI 8402, KOPTK1, PANC1 and nRas driven melanoma cell lines were grown in the presence or absence of 6-(4-Tert-Butylphenoxy)Pyridin-3-Amine (I3) for several days and their proliferative index was measured using the Alamar blue assay. In addition, B-lymphocyte RAJI cell lines with no known Notch mutations were used as a control (data not shown). As shown in FIG. 4, 6-(4-Tert-Butylphenoxy)Pyridin-3-Amine (I3) and DAPT treatment induced a significant proliferation block in T-ALL cell lines RPMI 8402, KOPTK1 and pancreatic cancer line PANC1. Similarly, 6-(4-Tert-Butylphenoxy)Pyridin-3-Amine (I3) significantly inhibited the growth of nRas driven melanoma cell lines (FIG. 4). However neither DAPT nor 6-(4-Tert-Butylphenoxy)Pyridin-3-Amine (I3) had any effect on the proliferation of Notch-independent RAJI cells (data not shown).

6-(4-Tert-Butylphenoxy)Pyridin-3-Amine (I3) but not DAPT Blocks Notch Signalling in NICD Overexpressing Human T-ALL and Breast Cancer Cell Line 6-(4-Tert-Butylphenoxy)Pyridin-3-Amine (I3) can block NICD mediated activation of the Notch pathway (FIG. 1). To determine whether 6-(4-Tert-Butylphenoxy)Pyridin-3-Amine (I3) can also induce a proliferation block in NICD overexpressing cells, the human T-ALL cell line DND41 (DND41-Parental) was transduced with a NICD expressing lentivirus to generate DND41-NICD cell line. These two cell lines were treated with DMSO, 6-(4-Tert-Butylphenoxy) Pyridin-3-Amine (I3) and DAPT. The treatment of DND41-parental cell line with DAPT and 6-(4-Tert-Butylphenoxy) Pyridin-3-Amine (I3) led to a downregulation of Hes1 when compared to DMSO treated cells. However, when DND41-NICD cells were treated with DMSO, 6-(4-Tert-Butylphenoxy)Pyridin-3-Amine (I3) and DAPT, only 6-(4-Tert-Butylphenoxy)Pyridin-3-Amine (I3), but not DAPT treatment caused a downregulation of Hes1 (FIG. 5A). In addition, these two cell lines were also monitored over several days for anti-proliferative effects of 6-(4-Tert-Butylphenoxy) Pyridin-3-Amine (I3) and DAPT. It was observed that while both 6-(4-Tert-Butylphenoxy)Pyridin-3-Amine (I3) and DAPT treatment caused a significant proliferative block in the DND41-Parental cell line (FIG. 5B), only 6-(4-Tert-Butylphenoxy)Pyridin-3-Amine (I3) was able to induce a growth arrest in DND41-NICD cells (FIG. 5C). This data further strengthen the notion that the 6-(4-Tert-Butylphenoxy)Pyridin-3-Amine (I3) compound can block NICD mediated pathway activation and proliferation in human cancer cells.

To further strengthen the notion that 6-(4-Tert-Butylphenoxy)Pyridin-3-Amine (I3) can block NICD mediated pathway activation and proliferation of human cancer cells, HCC1187 human breast cancer cell lines was treated with this compound. HCC1187 cell line harbors a SECC22B-Notch2 chromosomal translocation, thus generating constitutively active form of N2-ICD (FIG. 5D). Due to this mutation, HCC1187 cell lines do not respond to γ-secretase inhibitors such as DAPT. As shown is FIG. 5E, while DAPT treatment did not inhibit proliferation of HCC1187 cell lines, 6-(4-Tert-Butylphenoxy)Pyridin-3-Amine (I3) treatment significantly induced a proliferation block in these cell line.

6-(4-Tert-Butylphenoxy)Pyridin-3-Amine (I3) Induces G0/G1 Cell Cycle Arrest and Apoptosis in Human T Cell Acute Lymphoblastic Leukemia Cell Lines As shown in FIGS. 4 and 5, 6-(4-Tert-Butylphenoxy) Pyridin-3-Amine (I3) treatment of human leukemic cell lines and human breast cancer cell lines negatively regulate proliferation. This 6-(4-Tert-Butylphenoxy)Pyridin-3-Amine (I3) mediated proliferative arrest could be due to induction of apoptosis or cell cycle arrest during different phases of cell cycle. In addition, inhibition of Notch signalling using γ-secretase inhibitors has been shown to induce G0/G1 cell cycle arrest in human TALL cell lines. Therefore to further elucidate the mechanisms responsible for 6-(4-Tert-Butylphenoxy)Pyridin-3-Amine (I3) mediated proliferative arrest cell cycle and apoptosis analyses were carried out. Human TALL cell lines (RPMI8402, KOPTK1, TALL1, CUTL1 and HPB ALL) and human breast cancer cell line HCC1187 were treated with 6-(4-Tert-Butylphenoxy)Pyridin-3-Amine (I3) or DMSO for 2 days or 7 days. To investigate cell death, Annexin V staining was performed and proportion of apoptotic (AnnexinV positive) cell population was determined by flow cytometry analyses after 7 days of treatment. As shown in FIG. 6A, 6-(4-Tert-Butylphenoxy)Pyridin-3-Amine (I3) treatment induces significant apoptosis in RPMI8402, CUTL1, KOPTK1, TALL1 and HPB ALL. Similarly, 6-(4-Tert-Butylphenoxy)Pyridin-3-Amine induces apoptosis in human breast cancer cell line HCC1187 (FIG. 6C).

In addition to induction of apoptosis, the proliferative arrest observed in 6-(4-Tert-Butylphenoxy)Pyridin-3-Amine (I3) treated human leukemic cell lines and breast cancer cell line also appears to be due to cell cycle arrest in G0/G1 phase of the cell cycle. Leukemic cell lines (RPMI8402, KOPTK1 and TALL1) and breast cancer cell lines were treated with 6-(4-Tert-Butylphenoxy)Pyridin-3-Amine (I3) for 48 hours and cell cycle status was determined using Ki67 and Hoechst stain. As shown in FIGS. 6B and 6D, 6-(4-Tert-Butylphenoxy)Pyridin-3-Amine (I3) induces an arrest in the G0/G1 phase of the cell cycle, a phenotype normally observed due to inhibition of Notch signalling.

6-(4-Tert-Butylphenoxy)Pyridin-3-Amine (I3) Mediated Notch Signalling Inhibition Induces C2C12 Myoblast Differentiation To further confirm the Notch inhibitory potential of 6-(4-Tert-Butylphenoxy)Pyridin-3-Amine (I3) in different systems, C2C12 myoblast differentiation was used as a functional assay. The Notch pathway activation in C2C12 myoblasts retains them in an undifferentiated state, while abrogation of Notch signalling induces their differentiation. C2C12 myoblasts were treated with DMSO, 6-(4-Tert-Butylphenoxy)Pyridin-3-Amine (I3) and DAPT and grown to 100% confluency for 3 days. After three days, cells were fixed and stained with antibodies against Myosin Heavy Chain (MHC) protein. Cell nuclei were counterstained with DAPI. C2C12 myoblasts grown in the presence of 10% serum (growth medium) maintain their undifferentiated state, while the cells treated with DAPT and 6-(4-Tert-Butylphenoxy)Pyridin-3-Amine (I3) started to differentiate into multinucleated MHC positive myotubes (data not shown).

6-(4-Tert-Butylphenoxy)Pyridin-3-Amine (I3) does not Impede Upon Wnt and Hedgehog Signalling Cascades One of the concerns about the activity of the chemical compound 6-(4-Tert-Butylphenoxy)Pyridin-3-Amine (I3) is its specificity towards the Notch signalling pathway.

In order to test whether 6-(4-Tert-Butylphenoxy)Pyridin-3-Amine (I3) could also block other developmental pathways, Applicants have tested its ability to block the Wnt and Hedgehog signalling pathways. In summary, to measure Wnt signalling, HeLa cells were transfected with a plasmid containing a promoter consisting of TCF/LEF binding sites and thereby driving the expression of a luciferase gene (TOP-luciferase). To activate the Wnt pathway, a plasmid encoding for β-catenin was co-transfected into HeLa cells. The co-transfected cells were incubated in the presence or absence of the 6-(4-Tert-Butylphenoxy)Pyridin-3-Amine (I3) chemical compound. Transient introduction of β-catenin leads to an upregulation of Wnt signalling as measured by β-catenin-TCF/LEF driven luciferase activity. Importantly, 6-(4-Tert-Butylphenoxy)Pyridin-3-Amine (I3) treatment of cells with activated Wnt signalling does not block the Wnt pathway activation (data not shown).

Using a similar strategy, Hedgehog signalling was activated in HeLa cells by introducing the Gli1 transcription factor and pathway activation was monitored using a promoter sequence containing Gli1 binding sites driving the luciferase expression. The treatment of these cells with 6-(4-Tert-Butylphenoxy)Pyridin-3-Amine (I3) did not inhibit the Hedgehog signalling cascade (data not shown). Taken together these data suggest that the 6-(4-Tert-Butylphenoxy)Pyridin-3-Amine (I3) chemical compound may not impair other developmental pathways and might be specific for Notch signalling inhibition. However it still needs to be determined whether the resistance of Wnt and Hedgehog signalling towards 6-(4-Tert-Butylphenoxy)Pyridin-3-Amine (I3) is cell type specific or whether it is a general phenomenon.

In Vivo Effects of 6-(4-Tert-Butylphenoxy)Pyridin-3-Amine (I3) in C57BL6 Mice

Notch signalling regulates homeostasis of several organs during development. For example, Notch1 mediated pathway activation is essential for T cell development in the thymus (Radtke et al., 1999). However, the Notch1 driven T cell development does not appear to be dependent on MAML1, as the loss of MAML1 did not perturb T cell development in the mice. This could be due to a compensatory mechanism by MAML2 and MAML3 family members for the loss of MAML1. In the spleen, Notch2 driven signalling exclusively via MAML1 is required for MZB cell development. Genetic ablation loss of Notch2 and MAML1 cause a block in the development of MZB cells (Wu et al., 2007, Saito et al., 2003). In addition, Notch signalling via both Notch1 and Notch2 is essential for the maintenance of the crypt compartment. A compound genetic ablation of Notch1 and Notch2 in the intestine leads to goblet cell metaplasia. Applicants therefore, investigated whether 6-(4-Tert-Butylphenoxy)Pyridin-3-Amine (I3) could impair above-mentioned Notch-dependent developmental processes.

In in vitro culture assays, chemical compound 6-(4-Tert-Butylphenoxy)Pyridin-3-Amine (I3) was able to block Notch1 and Notch2 mediated pathway activation. Therefore, Applicants hypothesized that treatment of mice with 6-(4-Tert-Butylphenoxy)Pyridin-3-Amine (I3) may lead to a goblet cell metaplasia of the intestine. To test this hypothesis, mice were intra peritoneally (i.p) injected with 25 mg/kg of 6-(4-Tert-Butylphenoxy)Pyridin-3-Amine (I3) for 7 consecutive days. On day 8, animals were sacrificed and intestinal tissues were fixed and embedded in paraffin. Histological analyses were carried out using Alcian blue to stain for goblet cells. Surprisingly, despite its ability to block both Notch1 and Notch2 mediated pathway activation in in vitro cultures, the intestinal tissue of 6-(4-Tert-Butylphenoxy) Pyridin-3-Amine (I3) treated mice was completely normal with intact architecture and no indication of goblet cell metaplasia (data not shown). Similarly, the effect of 6-(4-Tert-Butylphenoxy)Pyridin-3-Amine (I3) on body weight changes was also monitored. Mice were injected for 5 consecutive days with 25 mg/kg of 6-(4-Tert-Butylphenoxy) Pyridin-3-Amine (I3) and the changes in body mass were recorded. The treatment of mice with 6-(4-Tert-Butylphenoxy)Pyridin-3-Amine (I3) did not cause a loss in the body weight.

6-(4-Tert-Butylphenoxy)Pyridin-3-Amine (I3) Treatment Induces a Block in MZB Cell Development Applicants hypothesized that 6-(4-Tert-Butylphenoxy) Pyridin-3-Amine (I3) mediated inhibition of Notch2 signalling should lead to a block in MZB cell development in the spleen. MZB cell development was assessed by flow cytometry staining of splenocytes with antibodies directed against B220, CD21 and CD23. As shown in FIG. 7B treatment of mice with 6-(4-Tert-Butylphenoxy)Pyridin-3-Amine (I3) leads to a reduction in the percentage of MZB cell population in the spleen. In addition, the loss of MZB cell population in the spleen also reflects in the absolute number of MZB cells (FIG. 7C).

Therefore, 6-(4-Tert-Butylphenoxy)Pyridin-3-Amine (I3) mediated block in MZB cell development mimics loss of Notch2 and MAML1 phenotype. However, it is still need to be seen, whether 6-(4-Tert-Butylphenoxy)Pyridin-3-Amine (I3) exert its Notch inhibitory effect only via MAML1 or it could block Notch signalling via other MAML family members as well.

6-(4-Tert-Butylphenoxy)Pyridin-3-Amine (I3) Treatment Slows Tumor Growth of Human T Cell Leukemia in a Xenotransplantation Model Activation of Notch signalling due to activating mutations in different components of the pathway are known to cause more than 50% of the human T cell acute lymphoblastic leukemias. Therefore, Applicants decided to investigate the anti-cancer activity of the chemical compound 6-(4-Tert-Butylphenoxy)Pyridin-3-Amine (I3) in Notch driven human T cell leukemia in vivo. To achieve this goal, xenotransplant models of human leukemia were established using NOD/SCID $\gamma c^{-/-}$ mice. Human T-ALL cell lines HPB ALL and RPMI 8402 were used for this purpose. The HPB ALL cell line harbours a L1575P mutation in the heterodimerization domain and an insertion in the PEST domain of the Notch1 receptor, thereby constitutively activating the Notch1 signalling. Similarly, RPMI 8402 cells exhibit ligand independent Notch signalling activation due to an insertion at 1584 a.a residue in the heterodimerization domain and also an inactivating mutation (R465H) in the E3 ligase FBW7. Both these cells line were found to respond to 6-(4-Tert-Butylphenoxy)Pyridin-3-Amine (I3) treatment in in vitro culture assays in terms of proliferation and/or downregulation of the Notch target genes. To determine whether these cell lines establish leukemia in a xenotransplant setting, one million cells from each line were intra venously (i.v) injected into NOD/SCID$\gamma c^{-/-}$ mice. The animals developed leukemia with 100% penetrance and die within 4 weeks after transplantation.

Once RPMI 8402 and HPB ALL cell lines were shown to develop leukemia in a xenotransplantation assay, they were transduced with a lentivirus constitutively expressing luciferase gene. This allowed Applicants to visualize and monitor the leukemia progression in the mice using the Caliper IVIS (Xenogen) live imaging detection system. In order to determine the anti-cancer efficacy of 6-(4-Tert-Butylphenoxy)Pyridin-3-Amine (I3) in established tumors, a maintenance experiment was performed. One million HPB ALL cells were injected (i.v) into NOD/SCID $\gamma c^{-/-}$ mice. Mice were monitored for leukemia development by detecting luciferase expressing leukemic cells. Once the disease was established around day 15, the mice were split into two groups. One group was treated with oil as a control and the second group was treated with 25 mg/kg of 6-(4-Tert-Butylphenoxy)Pyridin-3-Amine (I3) on a daily basis. As shown in FIG. 8A, the mice treated with oil develop leukemia with 100% penetrance while leukemia in the 6-(4-Tert-Butylphenoxy)Pyridin-3-Amine (I3) treated mice did not progress at the same rate as in the oil treated group (FIG. 8A).

Similarly in a preliminary experiment, NOD/SCID $\gamma c^{-/-}$ mice were transplanted with $5 \times 10^5$ RPMI 8402 cells and treated with oil or 6-(4-Tert-Butylphenoxy)Pyridin-3-Amine (I3) following the establishment of the disease. As shown in FIG. 8B, animals treated with oil, developed leukemia while 6-(4-Tert-Butylphenoxy)Pyridin-3-Amine (I3) treated mice were free of the disease. Furthermore, histological analyses revealed that in oil treated mice, leukemic cells progressed to infiltrate the liver, but 6-(4-Tert-Butylphenoxy)Pyridin-3-Amine (I3) treated mice did not develop any metastatic lesions in the liver (data not shown). Since these animals were treated with the chemical compound 6-(4-Tert-Butylphenoxy)Pyridin-3-Amine (I3) for 27 days, the intestinal tissue was analyzed to detect any toxicity in the gut. Alcian blue staining of intestinal tissue did not reveal any abnormality in the goblet cell numbers and intestinal architecture (data not shown).

Taken together Applicants' data from xenotransplantation model for human leukemia suggest that 6-(4-Tert-Butylphenoxy)Pyridin-3-Amine (I3) has the ability to slow down disease progression of an already established leukemia. Because of its ability to impact tumor progression, I3 may be a suitable candidate for further development as an anti-cancer agent.

MMTV-ErbB2 Mouse Mammary Tumors Exhibit Notch Signalling Activation and Effect of 6-(4-Tert-Butylphenoxy)Pyridin-3-Amine (I3) on Mammary Tumor Progression In human breast cancer, high levels of Notch1 and Jagged1 proteins correlated with a poor survival of breast cancer patients. In addition, activation of Notch signalling in human breast cancer also facilitates bone and lung metastasis. Therefore in order to determine anti-cancer potential of chemical compound 6-(4-Tert-Butylphenoxy)Pyridin-3-Amine (I3) in breast cancer, a mouse model of breast cancer was investigated. The mouse mammary tumor virus (MMTV) driven overexpression of ErbB2 is known to cause mouse mammary tumors. MMTV-ErbB2 transgenic mice develop mammary tumors with a latency of about 5-6 months along with the development of lung metastasis. One of the characteristics of MMTV-ErbB2 mouse mammary tumors is the presence of predominantly luminal epithelial cell types. Notch signalling is known to drive luminal cell differentiation from mouse mammary stem cells. Therefore Applicants hypothesized that the activation of the Notch pathway in MMTV-ErbB2 mammary tumors may contribute towards tumorigenesis in part by favouring luminal epithelial cell differentiation. To this end, Applicants investigated the levels of Notch signalling activation in MMTV-ErbB2-IRES-Cre mammary tumors by measuring the levels of Hes1 by Western blotting. As shown in FIG. 9A, MMTV-ErbB2 driven mammary tumors express very high levels of Hes1 protein compared to age matched normal mammary glands. To investigate the effect of 6-(4-Tert-Butylphenoxy)Pyridin-3-Amine (I3) on breast cancer development, MMTV-ErbB2 mammary tumors were harvested from FVB mice carrying the MMTV-ErbB2 transgene. A single cell suspension was prepared and $5 \times 10^5$ tumor cells were injected into an empty fat pad of a recipient FVB mouse. Once palpable tumors had developed, recipient mice were treated with either oil or 25 mg/kg of 6-(4-Tert-Butylphenoxy)Pyridin-3-Amine (I3) on alternate days until the end of the experiment. The tumor volume was measured and recorded on regular intervals. Preliminary results showed that the treatment of tumor bearing recipient mice with 6-(4-Tert-Butylphenoxy)Pyridin-3-Amine (I3) caused significant tumor growth retardation when compared to mice treated with oil alone (FIG. 9B). This data showed that 6-(4-Tert-Butylphenoxy)Pyridin-3-Amine (I3) has the ability to slow down the growth of established breast cancer.

6-(4-Tert-Butylphenoxy)Pyridin-3-Amine (I3) Blocks Notch Signalling in Primary Human T Cell Acute Lymphoblastic Leukemias To further investigate the Notch inhibitory effect of 6-(4-Tert-Butylphenoxy)Pyridin-3-Amine (I3) in a relevant pathological condition, primary human TALL samples were profiled for the activation of Notch signalling. An accumulation of active form of Notch (NICD) was used as a biomarker for pathway activation. Several primary human TALL exhibited an accumulation of oncogenic NICD and treatment of these tumors with 6-(4-Tert-Butylphenoxy)Pyridin-3-Amine (I3) leads to a downregulation of this protein. Moreover, the downregulation of NICD in these primary human TALL samples correlates with a proliferative arrest (data not shown). On the contrary, primary human TALL samples that do not show detectable levels of NICD, did not respond to 6-(4-Tert-Butylphenoxy)Pyridin-3-Amine (I3) treatment (data not shown).

These data indicates that an accumulation of NICD can be used as a biomarker for Notch pathway activation and predict treatment outcome using Notch inhibitor 6-(4-Tert-Butylphenoxy)Pyridin-3-Amine (I3).

Different Derivatives of 6-(4-Tert-Butylphenoxy)Pyridin-3-Amine (I3) Exhibit an Ability to Block Notch Signalling Activation in DL4-N1 Coculture Assay In order to enhance the Notch inhibitory activity as well as efficacy of parental 6-(4-Tert-Butylphenoxy)Pyridin-3-Amine (I3) compound, different chemical derivatives of I3 were tested in DL4-N1 coculture assay. Screening of more than 40 different chemical derivatives of 6-(4-Tert-Butylphenoxy)Pyridin-3-Amine (I3) yielded following compounds for their ability to block Notch pathway activation in coculture assay (FIG. 10).
I3-A). 6-(4-cyclohexyl phenoxy)pyri din-3-amine
I3-B) 6-(4-(tert-Pentyl)phenoxy)pyridin-3-amine (CAS #1036533-91-1)
I3-C) 4-(4-(tert-butyl)phenoxy)aniline (CAS #56705-89-6)
I3-D). 6-(4-Butylphenoxy)pyridin-3-amine
I3-E). 4-(4-(tert-pentyl)phenoxy)aniline (CAS #328032-81-1)
I3-F). 4-(4-cyclohexylphenoxy)aniline (CAS #70682-64-3)
I3-G) 6-(4-((3r,5r,7r)-adamantan-1-yl)phenoxy)pyridin-3-amine
I3-H). 6-(3-(tert-butyl)phenoxy)pyridin-3-amine (CAS #1098366-43-8)
I3-I). 4-(4-(tert-butyl)phenoxy)-3-fluoroaniline (CAS #946785-77-9)
I3-J). 4-(4-isopropylphenoxy)aniline
I3-K). 6-(4-(2,4,4-trimethylpentan-2-yl)phenoxy)pyridin-3-amine
I3-L). 4-(4-cyclohexylphenoxy)-3-fluoroaniline
I3-M). 3-fluoro-4-(4-(tert-pentyl)phenoxy)aniline
I3-N). 6-(4-(2-methylpentan-2-yl)phenoxy)pyridin-3-amine
I3-O). 4-(4-((3r, 5r,7r)-adamantan-1-yl)phenoxy)aniline
I3-P). 4-(4-((3r,5r,7r)-adamantan-1-yl)phenoxy)-3-fluoroaniline As shown in FIG. 10, some of these derivatives (I3-A, I3-B, I3-C, I3-E, I3-G, I3-H, I3-M and I3-N) block Notch signalling to comparable levels to parental compound I3, while derivatives I3-F and I3-I appears to have enhanced activity Example 3

Chemical synthesis of the Derivative and Precursors Thereof 4-(2-methylpentan-2-yl)phenol

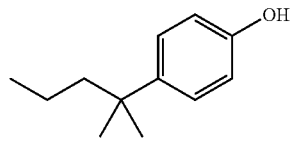

4-Butyrylphenol (1000 mg, 6.09 mmol, 1.00 eq) was suspended in toluene (25 mL) and DCM (5 mL) and cooled to 0° C. 2M Me$_3$Al solution in toluene (7 mL, 14.01 mmol, 2.30 eq) was added dropwise whereby the starting material was dissolved. After stirring at room temperature for 15 h, the reaction mixture was again cooled to 0° C. and TMSOSO$_2$CF$_3$ (1.1 mL, 6.09 mmol, 1.00 eq) was added dropwise. After stirring at room temperature for 3 d, the reaction was quenched by pouring the mixture into ice-water. After acidification with 40% H$_3$PO$_4$, the product was extracted with ethyl acetate (3×) and the organic layers were washed with H$_3$PO$_4$-acidic sat. aq. NaCl solution. The solvent was removed under reduced pressure at 30° C. The resulting crude product was purified by flash column chromatography (SiO$_2$; DCM/petrolether 1:1 to 2:1) to give the title compound as colourless oil (188 mg, with a purity of around 90% (by NMR), 0.95 mmol, 15% yield). R$_f$=0.60 (DCM/MeOH 4%). HRMS (ESI) calcd. for C$_{12}$H$_{17}$O$^-$ [M−H]$^-$ 177.1279. found: 177.1284. $^1$H NMR (400 MHz, CDCl$_3$) δ 7.24-7.18 (m, 2H, aromatic H), 6.82-6.76 (m, 2H, aromatic H), 5.12 (s, 1H, OH), 1.60-1.52 (m, 2H, C(CH$_3$)$_2$CH$_2$CH$_2$CH$_3$), 1.27 (s, 6H, C(CH$_3$)$_2$CH$_2$CH$_2$CH$_3$), 1.16-1.01 (m, 2H, C(CH$_3$)$_2$CH$_2$CH$_2$CH$_3$), 0.83 (t, J=7.3 Hz, 3H, C(CH$_3$)$_2$CH$_2$CH$_2$CH$_3$). $^{13}$C NMR (101 MHz, CDCl$_3$) δ 153.03, 142.29, 127.11, 114.85, 47.35, 37.25, 29.23, 18.09, 14.90.
General Procedure A:

The respective nitropyridines or nitrobenzenes and the particular phenols were dissolved in DMF or DMSO. Anhydrous K$_2$CO$_3$ was added and the reaction mixture was stirred at room temperature, unless otherwise stated, until complete conversion. The reaction was then quenched by the addition of H₂O and the product was extracted with EtOAc or Et₂O. The organic layers were washed with 1M aq. NaOH solution (1×) and afterwards with sat. aq. NaCl solution (1×). The solvent was removed to dryness under reduced pressure at 30° C. The residue was resolved in DCM and filtered through cotton to remove inorganic salts. The crude product was purified by flash column chromatography to afford the corresponding title compounds (I3-n, I3-nA to I3-nP).

2-(4-(tert-butyl)phenoxy)-5-nitropyridine, I3-n

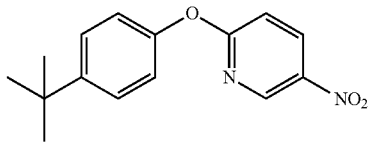 [SMILES: CC(C)(C)c1ccc(Oc2ccc([N+](=O)[O-])cn2)cc1]

Following procedure A, 2-chloro-5-nitropyridine (501 mg, 3.16 mmol, 1.00 eq) and 4-tert-butylphenol (611 mg, 4.07 mmol, 1.29 eq) were dissolved in DMF (6.0 mL). Anhydrous K₂CO₃ (654 mg, 4.73 mmol, 1.50 eq) was added and the reaction mixture was stirred at room temperature for 14 h. After extraction with Et₂O, the crude product was purified by flash column chromatography (SiO₂; EtOAc/petrolether 1:100 to 1:50) to afford the title compound as colourless solid (820 mg, 3.01 mmol, 95% yield). $R_f$=0.40 (EtOAc/PE 1:20). HRMS (ESI) calcd. for $C_{15}H_{17}N_2O_3^+$ [M+H]⁺ 273.1234. found: 273.1229. ¹H NMR (400 MHz, CDCl₃) δ 9.06 (d, J=2.8 Hz, 1H, aromatic H), 8.46 (dd, J=9.1, 2.8 Hz, 1H, aromatic H), 7.53-7.42 (m, 2H, aromatic H), 7.17-7.05 (m, 2H, aromatic H), 7.01 (d, J=9.1 Hz, 1H, aromatic H), 1.35 (s, 9H, C(CH₃)₃). ¹³C NMR (101 MHz, CDCl₃) δ 167.20, 150.49, 148.98, 145.26, 140.29, 134.95, 126.99, 120.84, 111.38, 34.72, 31.57.

2-(4-cyclohexylphenoxy)-5-nitropyridine, I3-nA

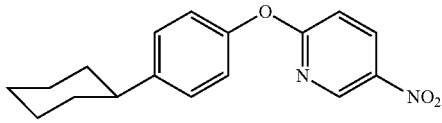 [SMILES: O=[N+]([O-])c1ccc(Oc2ccc(C3CCCCC3)cc2)nc1]

Following procedure A, 2-chloro-5-nitropyridine (300 mg, 1.89 mmol, 1.00 eq) and 4-cyclohexylphenol (417 mg, 2.37 mmol, 1.25 eq) were dissolved in DMSO (6 mL). Anhydrous K₂CO₃ (397 mg, 2.87 mmol, 1.52 eq) was added and the reaction mixture was stirred at room temperature for 27 h. After extraction with Et₂O, the crude product was purified by flash column chromatography (SiO₂; EtOAc/petrolether 1:100 to 1:75) to afford the title compound as colourless solid (600 mg, 2.01 mmol, quant. yield). $R_f$=0.35 (EtOAc/PE 1:20). FIRMS (ESI) calcd. for $C_{17}H_{19}N_2O_3^+$ [M+H]⁺ 299.1390. found: 299.1392. ¹H NMR (400 MHz, CDCl₃) δ 9.06 (d, J=2.9 Hz, 1H, aromatic H), 8.46 (dd, J=9.1, 2.9 Hz, 1H, aromatic H), 7.31-7.22 (m, 2H, aromatic H), 7.07 (dd, J=8.7, 2.3 Hz, 2H, aromatic H), 7.00 (d, J=9.1 Hz, 1H, aromatic H), 2.58-2.51 (m, 1H, cyclohexyl H), 2.01-1.64 (m, 5H, cyclohexyl H), 1.56-1.10 (m, 5H, cyclohexyl H). ¹³C NMR (101 MHz, CDCl₃) δ 167.18, 150.71, 145.88, 145.17, 140.22, 134.89, 128.30, 121.12, 111.30, 44.08, 34.59, 26.95, 26.19.

5-nitro-2-(4-(tert-pentyl)phenoxy)pyridine, I3-nB

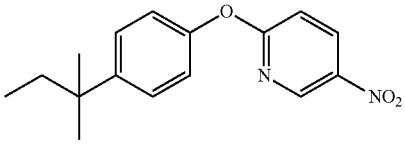 [SMILES: CCC(C)(C)c1ccc(Oc2ccc([N+](=O)[O-])cn2)cc1]

Following procedure A, 2-chloro-5-nitropyridine (303 mg, 1.91 mmol, 1.00 eq) and 4-tert-pentylphenol (397 mg, 2.42 mmol, 1.27 eq) were dissolved in DMSO (6 mL). Anhydrous K₂CO₃ (403 mg, 2.92 mmol, 1.53 eq) was added and the reaction mixture was stirred at room temperature for 7 h. After extraction with Et₂O, the crude product was purified by flash column chromatography (SiO₂; EtOAc/petrolether 1:100) to afford the title compound as colourless solid (530 mg, 1.85 mmol, 97% yield). $R_f$=0.31 (EtOAc/PE 1:20). HRMS (ESI) calcd. for $C_{16}H_{19}N_2O_3^+$ [M+H]⁺ 287.1390. found: 287.1381. ¹H NMR (400 MHz, CDCl₃) δ 9.07-9.05 (m, 1H, aromatic H), 8.45 (dd, J=9.4, 2.4 Hz, 1H, aromatic H), 7.40 (d, J=8.6 Hz, 2H, aromatic H), 7.09 (d, J=8.6 Hz, 2H, aromatic H), 6.99 (d, J=9.2 Hz, 1H, aromatic H), 1.67 (q, J=7.4 Hz, 2H, Ar—C(CH₃)₂CH₂CH₃), 1.31 (s, 6H, Ar—C(CH₃)₂CH₂CH₃), 0.73 (t, J=7.4 Hz, 3H, Ar—C(CH₃)₂CH₂CH₃). ¹³C NMR (101 MHz, CDCl₃) δ 167.17, 150.46, 147.34, 145.20, 140.27, 134.90, 127.56, 120.72, 111.28, 37.89, 37.06, 28.55, 9.26.

1-(tert-butyl)-4-(4-nitrophenoxy)benzene, I3-nC

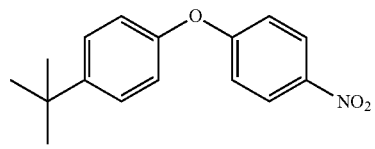

Following procedure A, 4-fluoronitrobenzene (500 mg, 3.54 mmol, 1.00 eq) and 4-tert-butylphenol (671 mg, 4.46 mmol, 1.26 eq) were dissolved in DMF (6.0 mL). Anhydrous K₂CO₃ (857 mg, 6.20 mmol, 1.75 eq) was added and the reaction mixture was stirred at room temperature for 52 h. After extraction with EtOAc, the crude product was purified by flash column chromatography (SiO₂; EtOAc/petrolether 1:100) to afford the title compound as pale yellow solid (860 mg, 3.17 mmol, 89% yield). $R_f$=0.72 (EtOAc/PE 1:9). HRMS (ESI) calcd. for $C_{16}H_{18}NO_3^+$ [M+H]⁺ 272.1281. found: 272.1272. ¹H NMR (400 MHz, CDCl₃) δ 8.24-8.16 (m, 2H, aromatic H), 7.49-7.39 (m, 2H, aromatic H), 7.06-6.97 (m, 4H, aromatic H), 1.35 (s, 9H, C(CH₃)₃). ¹³C NMR (101 MHz, CDCl₃) δ 163.82, 152.29, 148.59, 142.54, 127.27, 126.03, 120.15, 116.98, 34.67, 31.58.

2-(4-butylphenoxy)-5-nitropyridine, I3-nD

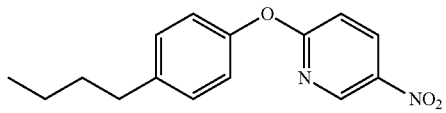 [SMILES: CCCCc1ccc(Oc2ccc([N+](=O)[O-])cn2)cc1]

Following procedure A, 2-chloro-5-nitropyridine (103 mg, 0.65 mmol, 1.00 eq) and 4-butylphenol (126 mg, 0.84 mmol, 1.29 eq) were dissolved in DMF (2.5 mL). Anhydrous $K_2CO_3$ (143 mg, 1.04 mmol, 1.59 eq) was added and the reaction mixture was stirred at room temperature for 6 h. After extraction with $Et_2O$, the crude product was purified by flash column chromatography ($SiO_2$; EtOAc/petrolether 1:100) to afford the title compound as colourless solid (190 mg, 0.70 mmol, quant. yield). $R_f$=0.33 (EtOAc/PE 1:20). HRMS (ESI) calcd. for $C_{15}H_{17}N_2O_3^+$ [M+H]$^+$ 273.1234. found: 273.1226. $^1$H NMR (400 MHz, CDCl$_3$) δ 9.05 (dd, J=2.9, 0.6 Hz, 1H, aromatic H), 8.46 (dd, J=9.1, 2.8 Hz, 1H, aromatic H), 7.32-7.21 (m, 2H, aromatic H), 7.11-7.02 (m, 2H, aromatic H), 7.00 (dd, J=9.0, 0.6 Hz, 1H, aromatic H), 2.69-2.60 (m, 2H, Ar—CH$_2$CH$_2$CH$_2$CH$_3$), 1.70-1.57 (m, 2H, Ar—CH$_2$CH$_2$CH$_2$CH$_3$), 1.39 (dq, J=14.6, 7.3 Hz, 2H, Ar—CH$_2$CH$_2$CH$_2$CH$_3$), 0.95 (t, J=7.3 Hz, 3H, Ar—CH$_2$CH$_2$CH$_2$CH$_3$). $^{13}$C NMR (101 MHz, CDCl$_3$) δ 167.27, 150.75, 145.22, 140.86, 140.30, 134.92, 129.91, 121.22, 111.32, 35.21, 33.67, 22.51, 14.08.

1-nitro-4-(4-(tert-pentyl)phenoxy)benzene, I3-nE

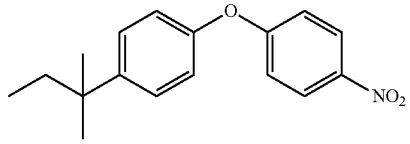 [SMILES: CCC(C)(C)c1ccc(Oc2ccc([N+](=O)[O-])cc2)cc1]

Following procedure A, 4-fluoronitrobenzene (318 mg, 2.25 mmol, 1.00 eq) and 4-tert-pentylphenol (460 mg, 2.28 mmol, 1.24 eq) were dissolved in DMSO (6 mL). Anhydrous $K_2CO_3$ (465 mg, 3.37 mmol, 1.49 eq) was added and the reaction mixture was stirred at room temperature for 2 h. After extraction with $Et_2O$, the crude product was purified by flash column chromatography ($SiO_2$; EtOAc/petrolether 1:100) to afford the title compound as colourless solid (533 mg, 1.87 mmol, 83% yield). $R_f$=0.70 (EtOAc/PE 1:20). HRMS (ESI) calcd. for $C_{17}H_{20}NO_3^+$ [M+H]$^+$ 285.1365. found: 285.1359. $^1$H NMR (400 MHz, CDCl$_3$) δ 8.25-8.14 (m, 2H, aromatic H), 7.44-7.32 (m, 2H, aromatic H), 7.06-6.96 (m, 4H, aromatic H), 1.66 (q, J=7.4 Hz, 2H, Ar—C(CH$_3$)$_2$CH$_2$CH$_3$), 1.31 (s, 6H, Ar—C(CH$_3$)$_2$CH$_2$CH$_3$), 0.71 (t, J=7.4 Hz, 3H, Ar—C(CH$_3$)$_2$CH$_2$CH$_3$). $^{13}$C NMR (101 MHz, CDCl$_3$) δ 163.81, 152.24, 146.94, 142.56, 127.91, 126.01, 120.06, 116.99, 37.89, 37.06, 28.63, 9.27.

1-cyclohexyl-4-(4-nitrophenoxy)benzene, I3-nF

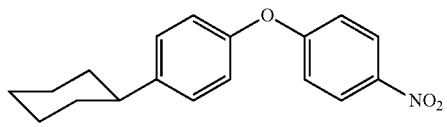 [SMILES: O=[N+]([O-])c1ccc(Oc2ccc(C3CCCCC3)cc2)cc1]

Following procedure A, 4-fluoronitrobenzene (325 mg, 2.30 mmol, 1.00 eq) and 4-cyclohexylphenol (519 mg, 2.94 mmol, 1.28 eq) were dissolved in DMSO (6 mL). Anhydrous $K_2CO_3$ (513 mg, 3.72 mmol, 1.61 eq) was added and the reaction mixture was stirred at room temperature for 48 h. After extraction with $Et_2O$, the crude product was purified by flash column chromatography ($SiO_2$; EtOAc/petrolether 1:100 to 1:50) to afford the title compound as pale yellow solid (640 mg, 2.15 mmol, 93% yield). $R_f$=0.55 (EtOAc/PE 1:20). FIRMS (ESI) calcd. for $C_{18}H_{20}NO_3^+$ [M+H]$^+$ 298.1438. found: 298.1442. $^1$H NMR (400 MHz, CDCl$_3$) δ 8.31-8.11 (m, 2H, aromatic H), 7.26 (d, J=2.3 Hz, 2H, aromatic H), 7.13-6.92 (m, 4H, aromatic H), 2.57-2.50 (m, 1H, cyclohexyl H), 2.09-1.67 (m, 5H, cyclohexyl H), 1.59-1.18 (m, 5H, cyclohexyl H). $^{13}$C NMR (101 MHz, CDCl$_3$) δ 163.89, 152.61, 145.58, 142.57, 128.66, 126.04, 120.49, 116.99, 44.14, 34.72, 26.99, 26.23.

2-(4-((3r,5r,7r)-adamantan-1-yl)phenoxy)-5-nitropyridine, I3-nG

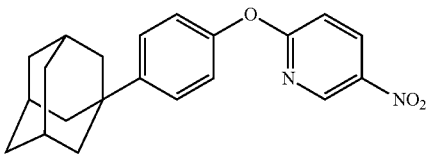 [SMILES: O=[N+]([O-])c1ccc(Oc2ccc(C34CC5CC(CC(C5)C3)C4)cc2)nc1]

Following procedure A, 2-chloro-5-nitropyridine (300 mg, 1.89 mmol, 1.00 eq) and 4-adamantylphenol (546 mg, 2.39 mmol, 1.26 eq) were dissolved in DMSO (6 mL). Anhydrous $K_2CO_3$ (662 mg, 4.79 mmol, 2.53 eq) was added and the reaction mixture was stirred at room temperature for 42 h. After extraction with $Et_2O$, the crude product was purified by flash column chromatography ($SiO_2$; EtOAc/petrolether 1:100 to 1:50) to afford the title compound as colourless solid (664 mg, 1.89 mmol, quant. yield). $R_f$=0.36 (EtOAc/PE 1:20). FIRMS (ESI) calcd. for $C_{21}H_{23}N_2O_3^+$ [M+H]$^+$ 351.1703. found: 351.1701. $^1$H NMR (400 MHz, CDCl$_3$) δ 9.06 (d, J=2.8 Hz, 1H, aromatic H), 8.45 (dd, J=9.1, 2.8 Hz, 1H, aromatic H), 7.52-7.39 (m, 2H, aromatic H), 7.16-7.06 (m, 2H, aromatic H), 7.00 (d, J=9.1 Hz, 1H, aromatic H), 2.13-2.10 (m, 3H, adamantyl H), 1.94 (d, J=3.0 Hz, 5H, adamantyl H), 1.87-1.70 (m, 5H, adamantyl H). $^{13}$C NMR (101 MHz, CDCl$_3$) δ 167.19, 150.51, 149.18, 145.20, 140.26, 134.89, 126.53, 120.83, 111.32, 43.35, 36.82, 36.18, 29.02.

2-(3-(tert-butyl)phenoxy)-5-nitropyridine, I3-nH

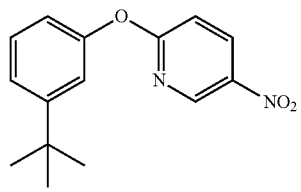

Following procedure A, 2-chloro-5-nitropyridine (300 mg, 1.89 mmol, 1.00 eq) and 3-tert-butylphenol (358 mg, 2.38 mmol, 1.26 eq) were dissolved in DMSO (6 mL). Anhydrous $K_2CO_3$ (420 mg, 3.04 mmol, 1.60 eq) was added and the reaction mixture was stirred at room temperature for 70 h. After extraction with $Et_2O$, the crude product was purified by flash column chromatography (SiO$_2$; EtOAc/petrolether 1:100) to afford the title compound as colourless solid (512 mg, 1.88 mmol, 99% yield). R$_f$=0.37 (EtOAc/PE 1:20). HRMS (ESI) calcd. for C$_{15}$H$_{17}$N$_2$O$_3^+$ [M+H]$^+$ 273.1234. found: 273.1232. $^1$H NMR (400 MHz, CDCl$_3$) δ 9.08-9.04 (m, 2H, aromatic H), 8.47 (dd, J=9.1, 2.8 Hz, 1H, aromatic H), 7.39 (t, J=7.9 Hz, 1H, aromatic H), 7.33 (ddd, J=7.9, 1.8, 1.2 Hz, 1H, aromatic H), 7.17 (t, J=2.1 Hz, 1H, aromatic H), 7.01 (dd, J=9.1, 0.5 Hz, 1H, aromatic H), 6.98 (ddd, J=7.9, 2.4, 1.2 Hz, 1H, aromatic H), 1.34 (s, 9H, C(CH$_3$)$_3$). $^{13}$C NMR (101 MHz, CDCl$_3$) δ 167.21, 153.88, 152.76, 145.26, 140.31, 134.93, 129.50, 123.17, 118.62, 118.47, 111.28, 35.02, 31.36.

1-(4-(tert-butyl)phenoxy)-2-fluoro-4-nitrobenzene, I3-nI

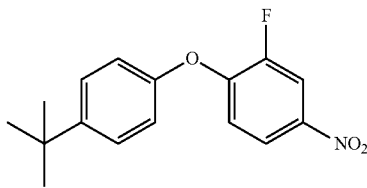 [SMILES: CC(C)(C)c1ccc(Oc2ccc([N+](=O)[O-])cc2F)cc1]

Following procedure A, 3,4-difluoronitrobenzene (401 mg, 2.52 mmol, 1.00 eq) and 4-tert-butylphenol (477 mg, 3.18 mmol, 1.26 eq) were dissolved in DMSO (6 mL). Anhydrous K$_2$CO$_3$ (522 mg, 3.78 mmol, 1.50 eq) was added and the reaction mixture was stirred at room temperature for 19 h. After extraction with Et$_2$O, the crude product was purified by flash column chromatography (SiO$_2$; EtOAc/petrolether 1:50) to afford the title compound as colourless oil (722 mg, 2.52 mmol, 99% yield). R$_f$=0.54 (EtOAc/PE 1:20). HRMS (ESI) calcd. for C$_{16}$H$_{17}$FNO$_3^+$ [M+H]$^+$ 290.1187. found: 290.1194. $^1$H NMR (400 MHz, CDCl$_3$) δ 8.07 (dd, J=10.3, 2.7 Hz, 1H, aromatic H), 7.96 (ddd, J=9.1, 2.7, 1.5 Hz, 1H, aromatic H), 7.49-7.38 (m, 2H, aromatic H), 7.09-6.99 (m, 2H, aromatic H), 6.96 (dd, J=9.1, 8.0 Hz, 1H, aromatic H), 1.35 (s, 9H, C(CH$_3$)$_3$). $^{13}$C NMR (101 MHz, CDCl$_3$) δ 153.35, 152.23, 151.93, 151.82, 150.84, 148.70, 142.40, 142.33, 127.29, 120.68, 120.64, 119.38, 117.73, 117.71, 113.28, 113.05, 34.65, 31.54.

1-(4-cyclohexylphenoxy)-2-fluoro-4-nitrobenzene, I3-nJ

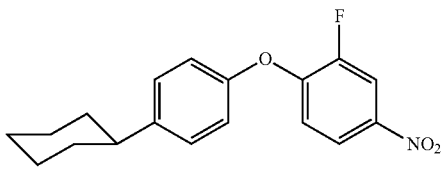

Following procedure A, 3,4-difluoronitrobenzene (509 mg, 3.20 mmol, 1.00 eq) and 4-cyclohexylphenol (691 mg, 3.93 mmol, 1.23 eq) were dissolved in DMSO (6 mL). Anhydrous K$_2$CO$_3$ (664 mg, 4.81 mmol, 1.50 eq) was added and the reaction mixture was stirred at room temperature for 23 h. After extraction with Et$_2$O, the crude product was purified by flash column chromatography (SiO$_2$; EtOAc/petrolether 1:50) to afford the title compound as pale yellow solid (1002 mg, 3.18 mmol, 99% yield). R$_f$=0.51 (EtOAc/PE 1:20). FIRMS (ESI) calcd. for C$_{15}$H$_{19}$FNO$_3^+$ [M+H]$^+$ 316.1343. found: 316.1348. $^1$H NMR (400 MHz, CDCl$_3$) δ 8.09 (dd, J=10.3, 2.7 Hz, 1H, aromatic H), 7.97 (ddd, J=9.1, 2.7, 1.4 Hz, 1H, aromatic H), 7.33-7.22 (m, 2H, aromatic H), 7.08-6.99 (m, 2H, aromatic H), 6.96 (dd, J=9.1, 8.0 Hz, 1H, aromatic H), 2.58-251 (m, 1H, cyclohexyl H), 1.98-1.73 (m, 5H, cyclohexyl H), 1.52-1.20 (m, 5H, cyclohexyl H). $^{13}$C NMR (101 MHz, CDCl$_3$) δ 153.35, 152.51, 152.01, 151.90, 150.84, 145.68, 142.39, 142.32, 128.67, 120.70, 120.66, 119.73, 117.70, 117.68, 113.30, 113.08, 44.09, 34.69, 26.97, 26.21.

2-fluoro-4-nitro-1-(4-(tert-pentyl)phenoxy)benzene, I3-nK

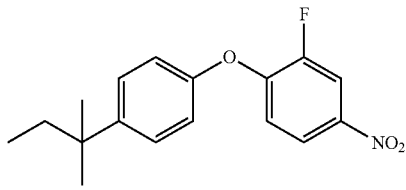 [SMILES: CCC(C)(C)c1ccc(Oc2ccc([N+](=O)[O-])cc2F)cc1]

Following procedure A, 3,4-difluoronitrobenzene (502 mg, 3.16 mmol, 1.00 eq) and 4-tert-pentylphenol (693 mg, 4.22 mmol, 1.34 eq) were dissolved in DMSO (6 mL). Anhydrous K$_2$CO$_3$ (656 mg, 4.75 mmol, 1.50 eq) was added and the reaction mixture was stirred at room temperature for 22 h. After extraction with Et$_2$O, the crude product was purified by flash column chromatography (SiO$_2$; EtOAc/petrolether 1:50) to afford the title compound as pale yellow oil (943 mg, 3.11 mmol, 99% yield). R$_f$=0.61 (EtOAc/PE 1:20). HRMS (ESI) calcd. for C$_{17}$H$_{19}$NO$_3^+$ [M+H]$^+$ 304.1343. found: 304.1332. $^1$H NMR (400 MHz, CDCl$_3$) δ 8.08 (dd, J=10.3, 2.7 Hz, 1H, aromatic H), 7.96 (ddd, J=9.1, 2.7, 1.5 Hz, 1H, aromatic H), 7.42-7.35 (m, 2H, aromatic H), 7.07-6.99 (m, 2H, aromatic H), 6.95 (dd, J=9.1, 8.0 Hz, 1H, aromatic H), 1.66 (q, J=7.4 Hz, 2H, Ar—C(CH$_3$)$_2$CH$_2$CH$_3$), 1.31 (s, 6H, Ar—C(CH$_3$)$_2$CH$_2$CH$_3$), 0.71 (t, J=7.4 Hz, 3H, Ar—C(CH$_3$)$_2$CH$_2$CH$_3$). $^{13}$C NMR (101 MHz, CDCl$_3$) δ 153.40, 152.19, 151.98, 151.87, 150.88, 147.11, 127.97, 120.71, 120.68, 119.34, 117.73, 117.71, 113.11, 37.92, 37.08, 28.64.

2-(4-(2-methylpentan-2-yl)phenoxy)-5-nitropyridine, I3-nL

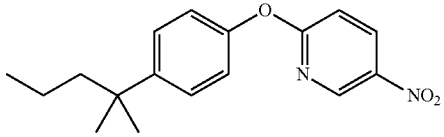 [SMILES: CCCC(C)(C)c1ccc(Oc2ccc([N+](=O)[O-])cn2)cc1]

Following procedure A, 4-(2-methylpentan-2-yl)phenol (52 mg, 0.29 mmol, 1.00 eq) and 2-chloro-5-nitropyridine (57 mg, 0.36 mmol, 1.23 eq) were dissolved in DMSO (6 mL). Anhydrous K$_2$CO$_3$ (66 mg, 0.48 mmol, 1.65 eq) was added and the reaction mixture was stirred at room temperature for 27 h. After extraction with Et$_2$O, the crude product was purified by flash column chromatography (SiO$_2$; EtOAc/petrolether 1:50) to afford the title compound as colourless solid (86 mg, 0.29 mmol, 98% yield). $R_f$=0.50 (EtOAc/PE 1:10). HRMS (ESI) calcd. for $C_{17}H_{21}N_2O_3^+$ [M+H]$^+$ 301.1547. found: 301.1545. $^1$H NMR (400 MHz, CDCl$_3$) δ 9.07 (d, J=2.7 Hz, 1H, aromatic H), 8.46 (dd, J=9.1, 2.8 Hz, 1H, aromatic H), 7.45-7.35 (m, 2H, aromatic H), 7.14-7.05 (m, 2H, aromatic H), 6.99 (dd, J=9.0, 0.6 Hz, 1H, aromatic H), 1.65-1.54 (m, 2H, C(CH$_3$)$_2$CH$_2$CH$_2$CH$_3$), 1.32 (s, 6H, C(CH$_3$)$_2$CH$_2$CH$_2$CH$_3$), 1.19-1.05 (m, 2H, C(CH$_3$)$_2$CH$_2$CH$_2$CH$_3$), 0.84 (t, J=7.3 Hz, 3H, C(CH$_3$)$_2$CH$_2$CH$_2$CH$_3$). $^{13}$C NMR (101 MHz, CDCl$_3$) δ 167.17, 150.43, 147.69, 145.21, 140.26, 134.90, 127.44, 120.72, 111.29, 47.27, 37.74, 29.07, 18.08, 14.87.

(3r,5r,7r)-1-(4-(4-nitrophenoxy)phenyl)adamantane, I3-nM

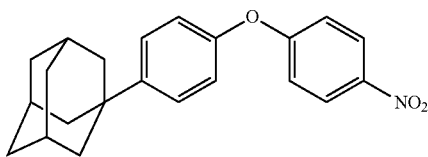 [SMILES: O=[N+]([O-])c1ccc(Oc2ccc(C34CC5CC(CC(C5)C3)C4)cc2)cc1]

Following procedure A, 4-fluoronitrobenzene (303 mg, 2.15 mmol, 1.00 eq) and 4-adamantylphenol (600 mg, 2.63 mmol, 1.22 eq) were dissolved in DMSO (6 mL). Anhydrous K$_2$CO$_3$ (450 mg, 3.26 mmol, 1.52 eq) was added and the reaction mixture was stirred at room temperature for 20 h. After extraction with Et$_2$O, the crude product was purified by flash column chromatography (SiO$_2$; EtOAc/petrolether 1:100 to 1:50) to afford the title compound as pale yellow solid (736 mg, 2.11 mmol, 98% yield). $R_f$=0.73 (EtOAc/PE 1:10). HRMS (ESI) calcd. for $C_{22}H_{24}NO_3^+$ [M+H]$^+$ 350.1751. found: 350.1760. $^1$H NMR (400 MHz, CDCl$_3$) δ 8.27 8.10 (m, 2H, aromatic H), 7.46-7.35 (m, 2H, aromatic H), 7.08-6.95 (m, 4H, aromatic H), 2.13-2.10 (m, 3H, adamantyl H), 1.93 (d, J=2.9 Hz, 6H, adamantyl H), 1.88-1.70 (m, 6H, adamantyl H). $^{13}$C NMR (101 MHz, CDCl$_3$) δ 163.85, 152.30, 148.86, 142.53, 126.86, 126.85, 126.03, 120.18, 117.00, 43.40, 36.82, 36.17, 29.03.

(3r,5r,7r)-1-(4-(2-fluoro-4-nitrophenoxy)phenyl) adamantane, I3-nN

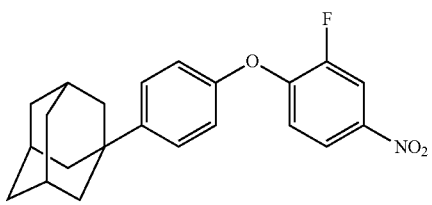 [SMILES: O=[N+]([O-])c1ccc(Oc2ccc(C34CC5CC(CC(C5)C3)C4)cc2)c(F)c1]

Following procedure A, 3,4-difluoronitrobenzene (303 mg, 1.90 mmol, 1.00 eq) and 4-adamantylphenol (533 mg, 2.34 mmol, 1.23 eq) were dissolved in DMSO (6 mL). Anhydrous K$_2$CO$_3$ (395 mg, 2.86 mmol, 1.50 eq) was added and the reaction mixture was stirred at room temperature for 4 h. After extraction with Et$_2$O, the crude product was purified by flash column chromatography (SiO$_2$; EtOAc/ petrolether 1:100) to afford the title compound as colourless solid (703 mg, 1.91 mmol, quant. yield). $R_f$=0.69 (EtOAc/PE 1:10). HRMS (APPI) calcd. for $C_{22}H_{22}FNO^+$ [M]+ 367.1584. found: 367.1581. $^1$H NMR (400 MHz, CDCl$_3$) δ 8.08 (dd, J=10.3, 2.7 Hz, 1H, aromatic H), 7.96 (ddd, J=9.1, 2.7, 1.5 Hz, 1H, aromatic H), 7.46-7.36 (m, 2H, aromatic H), 7.06-7.00 (m, 2H, aromatic H), 6.95 (dd, J=9.1, 8.0 Hz, 1H, aromatic H), 2.17-2.07 (m, 3H, adamantyl H), 1.92 (d, J=2.9 Hz, 5H, adamantyl H), 1.87-1.71 (m, 5H, adamantyl H). $^{13}$C NMR (101 MHz, CDCl$_3$) δ 153.36, 153.35, 152.24, 152.21, 151.99, 151.88, 150.85, 150.83, 148.98, 126.89, 120.70, 120.66, 119.44, 119.42, 117.72, 117.70, 113.30, 113.07, 43.38, 36.81, 36.17, 29.02.

2-(4-isopropylphenoxy)-5-nitropyridine, I3-n0

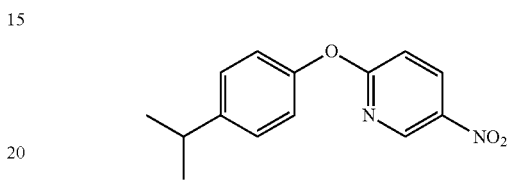

Following procedure A, 2-chloro-5-nitropyridine (303 mg, 1.91 mmol, 1.00 eq) and 4-iso-propylphenol (331 mg, 2.43 mmol, 1.27 eq) were dissolved in DMF (6.0 mL). Anhydrous K$_2$CO$_3$ (398 mg, 2.88 mmol, 1.51 eq) was added and the reaction mixture was stirred at room temperature for 24 h. After extraction with Et$_2$O, the crude product was purified by flash column chromatography (SiO$_2$; EtOAc/ petrolether 1:100) to afford the title compound as pale yellow solid (490 mg, 1.90 mmol, 99% yield). $R_f$=0.40 (EtOAc/PE 1:20). HRMS (ESI) calcd. for $C_{14}H_{15}N_2O_3^+$ [M+H]$^+$ 259.1077. found: 259.1072. $^1$H NMR (400 MHz, CDCl$_3$) δ 9.04 (d, J=3.4 Hz, 1H, aromatic H), 8.44 (dd, J=9.1, 2.8 Hz, 1H, aromatic H), 7.37-7.28 (m, 2H, aromatic H), 7.12-7.06 (m, 2H, aromatic H), 7.03-6.97 (m, 1H, aromatic H), 2.96 (hept, J=6.9 Hz, 1H, CH(CH$_3$)$_2$), 1.30 (d, J=7.0 Hz, 6H, CH(CH$_3$)$_2$). $^{13}$C NMR (101 MHz, CDCl$_3$) δ 167.08, 150.67, 146.49, 145.02, 140.18, 134.81, 127.84, 121.11, 111.24, 33.62, 24.03.

5-nitro-2-(4-(2,4,4-trimethylpentan-2-yl)phenoxy) pyridine, I3-nP

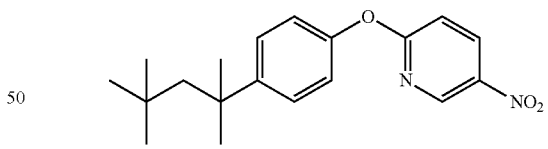

Following procedure A, 2-Chloro-5-nitropyridine (303 mg, 1.91 mmol, 1.00 eq) and 4-tert-octylphenol (495 mg, 2.40 mmol, 1.25 eq) were dissolved in DMSO (5 mL). Anhydrous K$_2$CO$_3$ (426 mg, 3.08 mmol, 1.61 eq) was added and the reaction mixture was stirred at 40° C. for 28 h. After extraction with Et$_2$O, the crude product was purified by flash column chromatography (SiO$_2$; EtOAc/petrolether 1:50) to afford the title compound as colourless solid (598 mg, 1.82 mmol, 95% yield). $R_f$=0.65 (EtOAc/PE 1:10). FIRMS (ESI) calcd. for $C_{19}H_{25}N_2O_3^+$ [M+H]$^+$ 329.1860. found: 329.1854. $^1$H NMR (400 MHz, CDCl$_3$) δ 9.07 (d, J=2.8 Hz, 1H, aromatic H), 8.45 (dd, J=9.1, 2.8 Hz, 1H, aromatic H), 7.52-7.40 (m, 2H, aromatic H), 7.14-7.03 (m, 2H, aromatic H), 6.97 (d, J=9.1 Hz, 1H, aromatic H), 1.76 (s, 2H, Ar—C(CH$_3$)$_2$CH$_2$C(CH$_3$)$_3$), 1.40 (s, 6H, Ar—C(CH$_3$)$_2$CH$_2$C(CH$_3$)$_3$), 0.75 (s, 9H, Ar—C(CH$_3$)$_2$CH$_2$C(CH$_3$)$_3$). $^{13}$C NMR (101 MHz, CDCl$_3$) δ 167.24, 150.49, 148.12, 145.30, 140.29, 134.92, 127.78, 120.57, 111.15, 57.28, 38.63, 32.55, 31.93, 31.62.

General Procedure B:

The respective nitro derivatives (I3-n, I3-nA to I3-nP) were first dissolved in MeOH or toluene, or directly added to a suspension of catalytic amounts of Pd (10%) on activated carbon powder in MeOH. The flask was purged with H$_2$ (6×) and the reaction mixture was stirred at room temperature until complete conversion. The reaction mixture was then filtered through Celite. The solvent was removed under reduced pressure at 30° C. and the crude product was purified by flash column chromatography to give the corresponding title compounds (I3, I3-A to I3-P).

6-(4-(tert-butyl)phenoxy)pyridin-3-amine, I3

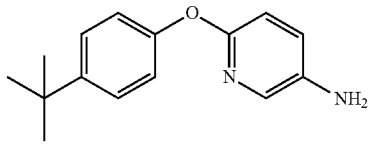 [SMILES: CC(C)(C)c1ccc(Oc2ccc(N)cn2)cc1]

Following procedure B, I3-n (300 mg, 1.10 mmol, 1.00 eq) was added to a suspension of Pd (10%) on activated carbon powder (82 mg, 0.08 mmol Pd, 0.07 eq) in MeOH (15 mL). The flask was purged with H$_2$ (6×) and the reaction mixture was stirred at room temperature for 2 h. The crude product was purified by flash column chromatography (SiO2; DCM/MeOH 1%) to give the title compound as pale beige solid (250 mg, 1.03 mmol, 94% yield). R$_f$=0.40 (DCM/MeOH 4%). HRMS (ESI) calcd. for C$_{15}$H$_{19}$N$_2$O$^+$ [M+H]$^+$ 243.1492. found: 243.1487. $^1$H NMR (400 MHz, CDCl$_3$) δ 7.69 (d, J=3.0 Hz, 1H, aromatic H), 7.39-7.31 (m, 2H, aromatic H), 7.03 (dd, J=8.6, 3.0 Hz, 1H, aromatic H), 7.00-6.93 (m, 2H, aromatic H), 6.72 (d, J=8.6 Hz, 1H, aromatic H), 3.48 (s, 1H, NH$_2$), 1.31 (s, 9H, C(CH$_3$)$_3$). $^{13}$C NMR (101 MHz, CDCl$_3$) δ 156.62, 153.28, 146.33, 138.82, 134.06, 126.86, 126.47, 119.24, 112.36, 34.33, 31.52.

6-(4-cyclohexylphenoxy)pyridin-3-amine, I3-A

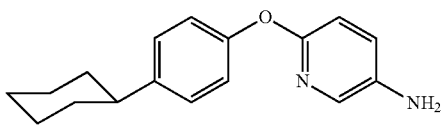

Following procedure B, I3-nA (201 mg, 0.67 mmol, 1.00 eq) was added to a suspension of Pd (10%) on activated carbon powder (47 mg, 0.04 mmol Pd, 0.07 eq) in MeOH (15 mL). The flask was purged with H$_2$ (6×) and the reaction mixture was stirred at room temperature for 5 h. The crude product was purified by flash column chromatography (SiO$_2$; DCM/MeOH 1%) to give the title compound as beige solid (190 mg, 0.71 mmol, quant. yield). R$_f$=0.36 (DCM/MeOH 4%). HRMS (ESI) calcd. for C$_{17}$H$_{21}$N$_2$O$^+$ [M+H]$^+$ 269.1648. found: 269.1643. $^1$H NMR (400 MHz, CDCl$_3$) δ 7.70 (d, J=2.9 Hz, 1H, aromatic H), 7.22-7.13 (m, 2H, aromatic H), 7.04 (dd, J=8.6, 3.0 Hz, 1H, aromatic H), 7.01-6.92 (m, 2H, aromatic H), 6.73 (dd, J=8.8, 0.7 Hz, 1H, aromatic H), 3.36 (s, 2H, NH$_2$), 2.51-2.44 (m, 1H, cyclohexyl H), 1.97-1.67 (m, 5H, cyclohexyl H), 1.49-1.15 (m, 5H, cyclohexyl H). $^{13}$C NMR (101 MHz, CDCl$_3$) δ 156.88, 153.61, 143.47, 138.67, 134.21, 127.92, 126.96, 119.68, 112.38, 43.99, 34.68, 27.01, 26.25.

6-(4-(tert-pentyl)phenoxy)pyridin-3-amine, I3-B

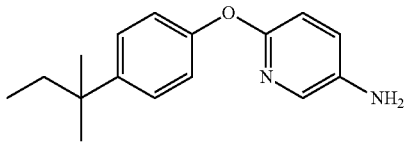

Following procedure B, I3-nB (200 mg, 0.70 mmol, 1.00 eq) was added to a suspension of Pd (10%) on activated carbon powder (52 mg, 0.05 mmol Pd, 0.07 eq) in MeOH (15 mL). The flask was purged with H$_2$ (6×) and the reaction mixture was stirred at room temperature for 3 h. The crude product was purified by flash column chromatography (SiO$_2$; DCM/MeOH 0.5%) to give the title compound as beige solid (107 mg, 0.42 mmol, 60% yield). R$_f$=0.41 (DCM/MeOH 4%). HRMS (ESI) calcd. for C$_{16}$H$_{21}$N$_2$O$^+$ [M+H]$^+$ 257.1648. found: 257.1648. $^1$H NMR (400 MHz, CDCl$_3$) δ 7.73 (d, J=2.9 Hz, 1H, aromatic H), 7.34-7.23 (m, 2H, aromatic H), 7.06 (dd, J=8.6, 3.0 Hz, 1H, aromatic H), 7.02-6.94 (m, 2H, aromatic H), 6.73 (d, J=8.6 Hz, 1H, aromatic H), 3.35 (s, 2H, NH$_2$), 1.62 (q, J=7.4 Hz, 2H, Ar—C(CH$_3$)$_2$CH$_2$CH$_3$), 1.27 (s, 6H, Ar—C(CH$_3$)$_2$CH$_2$CH$_3$), 0.70 (t, J=7.4 Hz, 3H, Ar—C(CH$_3$)$_2$CH$_2$CH$_3$). $^{13}$C NMR (101 MHz, CDCl$_3$) δ 156.80, 153.36, 144.75, 138.72, 134.30, 127.19, 126.97, 119.13, 112.51, 37.63, 37.04, 28.64, 9.26.

4-(4-(tert-butyl)phenoxy)aniline, I3-C

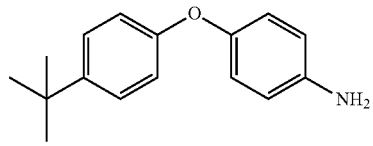

Following procedure B, I3-nC (300 mg, 1.11 mmol, 1.00 eq) was added to a suspension of Pd (10%) on activated carbon powder (59 mg, 0.06 mmol Pd, 0.05 eq) in MeOH (15 mL). The flask was purged with H$_2$ (6×) and the reaction mixture was stirred at room temperature for 3.5 h. The crude product was purified by flash column chromatography (SiO$_2$; ethyl acetate/petrolether 1:100 to 1:10) to give the title compound as dark yellow oil (244 mg, 1.01 mmol, 91% yield). R$_f$=0.78 (DCM/MeOH 4%). HRMS (ESI) calcd. for C$_{16}$H$_{20}$NO$^+$ [M+H]$^+$ 242.1539. found: 242.1530. $^1$H NMR (400 MHz, CDCl$_3$) δ 7.33-7.27 (m, 2H, aromatic H), 6.91-6.84 (m, 4H, aromatic H), 6.72-6.66 (m, 2H, aromatic H), 3.49 (s, 2H, NH$_2$), 1.31 (s, 9H, C(CH$_3$)$_3$). $^{13}$C NMR (101 MHz, CDCl$_3$) δ 156.55, 149.24, 145.05, 142.30, 126.45, 121.08, 116.90, 116.49, 34.33, 31.66.

6-(4-butylphenoxy)pyridin-3-amine, I3-D

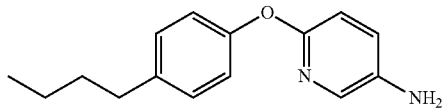 [SMILES: CCCCc1ccc(Oc2ccc(N)cn2)cc1]

Following procedure B, I3-nD (170 mg, 0.62 mmol, 1.00 eq) was added to a suspension of Pd (10%) on activated carbon powder (53 mg, 0.05 mmol Pd, 0.08 eq) in MeOH (15 mL). The flask was purged with $H_2$ (6×) and the reaction mixture was stirred at room temperature for 1.5 h. The crude product was purified by flash column chromatography ($SiO_2$; DCM/MeOH 1%) to give the title compound as brown oil (133 mg, 0.55 mmol, 88% yield). $R_f$=0.38 (DCM/MeOH 4%). HRMS (ESI) calcd. for $C_{15}H_{19}N_2O^+$ $[M+H]^+$ 243.1492. found: 243.1485. $^1$H NMR (400 MHz, $CDCl_3$) δ 7.69 (d, J=3.1 Hz, 1H, aromatic H), 7.20-7.09 (m, 2H, aromatic H), 7.03 (dd, J=8.6, 3.0 Hz, 1H, aromatic H), 7.00-6.91 (m, 2H, aromatic H), 6.72 (d, J=8.6 Hz, 1H, aromatic H), 3.36 (s, 2H, $NH_2$), 2.67-2.51 (m, 2H, Ar—$CH_2CH_2CH_2CH_3$), 1.66-1.52 (m, 2H, Ar—$CH_2CH_2CH_2CH_3$), 1.41-1.31 (m, 2H, Ar—$CH_2CH_2CH_2CH_3$), 0.93 (t, =7.3 Hz, 3H, Ar—$CH_2CH_2CH_2CH_3$). $^{13}$C NMR (101 MHz, $CDCl_3$) δ 156.83, 153.55, 138.75, 138.26, 134.12, 129.48, 126.90, 119.74, 112.28, 35.02, 33.74, 22.40, 14.02.

4-(4-(tert-pentyl)phenoxy)aniline, I3-E

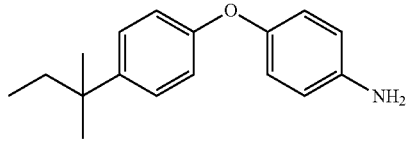

Following procedure B, I3-nE (313 mg, 1.10 mmol, 1.00 eq) was dissolved in MeOH (10 mL) and added to a suspension of Pd (10%) on activated carbon powder (52 mg, 0.05 mmol Pd, 0.04 eq) in MeOH (5 mL). The flask was purged with $H_2$ (6×) and the reaction mixture was stirred at room temperature for 3 h. The crude product was purified by filtration through a thin $SiO_2$ layer (DCM/MeOH 4%) to give the title compound as beige oil (293 mg, 1.15 mmol, quant. yield). $R_f$=0.09 (EtOAc/PE 1:20). HRMS (ESI) calcd. for $C_{17}H_{22}N_2O^+$ $[M+H]^+$ 256.1696. found: 256.1692. $^1$H NMR (400 MHz, $CDCl_3$) δ 7.29-7.19 (m, 2H, aromatic H), 6.98-6.81 (m, 4H, aromatic H), 6.76-6.61 (m, 2H, aromatic H), 3.47 (s, 2H, $NH_2$), 1.63 (q, J=7.4 Hz, 2H, Ar—$C(CH_3)_2CH_2CH_3$), 1.28 (s, 6H, Ar—$C(CH_3)_2CH_2CH_3$), 0.71 (t, J=7.4 Hz, 3H, Ar—$C(CH_3)_2CH_2CH_3$). $^{13}$C NMR (101 MHz, $CDCl_3$) δ 156.45, 149.08, 143.29, 142.55, 127.08, 121.04, 116.79, 116.33, 37.50, 37.06, 28.69, 9.27.

4-(4-cyclohexylphenoxy)aniline, I3-F

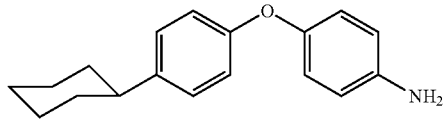

Following procedure B, I3-nF (352 mg, 1.18 mmol, 1.00 eq) was dissolved in toluene (5 mL) and added to a suspension of Pd (10%) on activated carbon powder (38 mg, 0.04 mmol Pd, 0.03 eq) in MeOH (10 mL). The flask was purged with $H_2$ (6×) and the reaction mixture was stirred at room temperature for 2 h. The crude product was purified by flash column chromatography ($SiO_2$; DCM) to give the title compound as beige solid (315 mg, 1.18 mmol, quant. yield). $R_f$=0.86 (DCM/MeOH 4%). HRMS (ESI) calcd. for $C_{18}H_{22}NO^+$ $[M+H]^+$ 268.1696. found: 268.1692. $^1$H NMR (400 MHz, $CDCl_3$) δ 7.17-7.07 (m, 2H, aromatic H), 6.94-6.82 (m, 4H, aromatic H), 6.72-6.62 (m, 2H, aromatic H), 3.49 (s, 2H, $NH_2$), 2.51-2.44 (m, 1H, cyclohexyl H), 1.98-1.68 (m, 5H, cyclohexyl H), 1.46-1.21 (m, 5H, cyclohexyl H). $^{13}$C NMR (101 MHz, $CDCl_3$) δ 156.87, 149.13, 142.53, 142.05, 127.81, 121.02, 117.22, 116.33, 43.90, 34.79, 27.05, 26.27.

6-(4-((3r,5r,7r)-adamantan-1-yl)phenoxy)pyridin-3-amine, I3-G

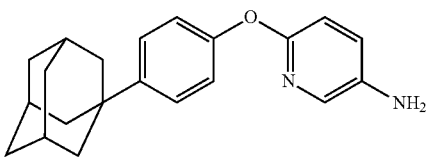 [SMILES: Nc1ccc(Oc2ccc(C34CC5CC(CC(C5)C3)C4)cc2)nc1]

Following procedure B, I3-nG (278 mg, 0.79 mmol, 1.00 eq) was dissolved in toluene (10 mL) and added to a suspension of Pd (10%) on activated carbon powder (56 mg, 0.05 mmol Pd, 0.07 eq) in MeOH (10 mL). The flask was purged with $H_2$ (3×) and the reaction mixture was stirred at room temperature for 3 h. The crude product was purified by flash column chromatography ($SiO_2$; DCM/MeOH 0% to 1%) to give the title compound as colourless solid (176 mg, 0.55 mmol, 69% yield). $R_f$=0.43 (DCM/MeOH 4%). HRMS (ESI) calcd. for $C_{21}H_{25}N_2O^+$ $[M+H]^+$ 321.1961. found: 321.1959. $^1$H NMR (400 MHz, $CDCl_3$) δ 7.71 (d, J=3.0 Hz, 1H, aromatic H), 7.37-7.29 (m, 2H, aromatic H), 7.08-6.96 (m, 3H, aromatic H), 6.74 (d, J=8.6 Hz, 1H, aromatic H), 3.40 (s, 2H, $NH_2$), 2.12-2.09 (m, 3H, adamantyl H), 1.93 (dd, J=9.7, 3.0 Hz, 5H, adamantyl H), 1.86-1.70 (m, 5H, adamantyl H). $^{13}$C NMR (101 MHz, $CDCl_3$) δ 156.73, 153.37, 151.35, 146.65, 138.76, 134.15, 128.14, 126.86, 126.06, 125.54, 124.88, 119.29, 112.40, 43.36, 43.22, 36.87, 36.84, 35.87, 29.02.

6-(3-(tert-butyl)phenoxy)pyridin-3-amine, I3-H

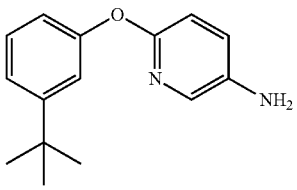 [SMILES: CC(C)(C)c1cccc(Oc2ccc(N)cn2)c1]

Following procedure B, I3-nH (362 mg, 1.33 mmol, 1.00 eq) was dissolved in MeOH (10 mL) and added to a suspension of Pd (10%) on activated carbon powder (44 mg, 0.04 mmol Pd, 0.03 eq) in MeOH (5 mL). The flask was purged with $H_2$ (5×) and the reaction mixture was stirred at room temperature for 2 h. The crude product was purified by flash column chromatography (SiO$_2$; DCM/MeOH 0% to 1%) to give the title compound as pale brown oil (303 mg, 1.25 mmol, 94% yield). R$_f$=0.44 (DCM/MeOH 4%). HRMS (ESI) calcd. for C$_{15}$H$_{19}$N$_2$O$^+$ [M+H]$^+$ 243.1492. found: 243.1493. $^1$H NMR (400 MHz, CDCl$_3$) δ 7.92 (d, J=3.0 Hz, 1H, aromatic H), 7.48-7.40 (m, 1H, aromatic H), 7.32 (ddd, J=7.8, 1.9, 1.0 Hz, 1H, aromatic H), 7.29-7.27 (m, 1H, aromatic H), 7.24 (d, J=3.0 Hz, 1H, aromatic H), 7.01 (ddd, J=8.0, 2.4, 1.0 Hz, 1H, aromatic H), 6.92 (dd, J=8.6, 0.7 Hz, 1H, aromatic H), 3.40 (s, 2H, NH$_2$) 1.48 (s, 9H, C(CH$_3$)$_3$). $^{13}$C NMR (101 MHz, CDCl$_3$) δ 156.81, 155.65, 153.31, 138.69, 134.40, 129.10, 126.99, 120.85, 117.23, 116.69, 112.54, 34.89, 31.41.

4-(4-(tert-butyl)phenoxy)-3-fluoroaniline, I3-I

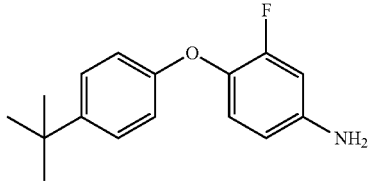 [SMILES: CC(C)(C)c1ccc(Oc2ccc(N)cc2F)cc1]

Following procedure B, I3-nI (501 mg, 1.73 mmol, 1.00 eq) was dissolved in MeOH (I3 mL) and added to a suspension of Pd (10%) on activated carbon powder (56 mg, 0.05 mmol Pd, 0.03 eq) in MeOH (2 mL). The flask was purged with H$_2$ (5×) and the reaction mixture was stirred at room temperature for 1.5 h. The crude product was purified by flash column chromatography (SiO$_2$; DCM) to give the title compound as colourless solid (455 mg, 1.75 mmol, quant. yield). R$_f$=0.76 (DCM/MeOH 1%). HRMS (ESI) calcd. for C$_{16}$H$_{19}$FNO$^+$[M+H]$^+$ 260.1445. found: 260.1442. $^1$H NMR (400 MHz, CDCl$_3$) δ 7.37-7.29 (m, 2H, aromatic H), 6.94 (t, J=8.8 Hz, 1H, aromatic H), 6.91-6.85 (m, 2H, aromatic H), 6.52 (dd, J=12.0, 2.7 Hz, 1H, aromatic H), 6.42 (ddd, J=8.6, 2.7, 1.3 Hz, 1H, aromatic H), 3.61 (s, 2H, NH$_2$), 1.33 (s, 9H, C(CH$_3$)$_3$). $^{13}$C NMR (101 MHz, CDCl$_3$) δ 156.58, 156.44, 154.12, 145.02, 144.42, 144.33, 134.83, 134.71, 126.41, 123.92, 123.90, 115.43, 110.97, 110.93, 103.93, 103.72, 34.25, 31.59.

4-(4-cyclohexylphenoxy)-3-fluoroaniline, I3-J

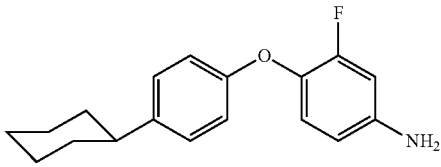 [SMILES: Nc1ccc(Oc2ccc(C3CCCCC3)cc2)c(F)c1]

Following procedure B, I3-nJ (550 mg, 1.74 mmol, 1.00 eq) was dissolved in MeOH (12 mL) and added to a suspension of Pd (10%) on activated carbon powder (46 mg, 0.04 mmol Pd, 0.03 eq) in MeOH (3 mL). The flask was purged with H$_2$ (6×) and the reaction mixture was stirred at room temperature for 2 h. The crude product was purified by flash column chromatography (SiO$_2$; DCM/petrolether 1:1 to 2:1) to give the title compound as pale rose solid (489 mg, 1.71 mmol, 98% yield). R$_f$=0.81 (DCM/MeOH 4%). HRMS (ESI) calcd. for C$_{18}$H$_{21}$FNO$^+$ [M+H]$^+$ 286.1602. found: 286.1613. $^1$H NMR (400 MHz, CDCl$_3$) δ 7.19-7.10 (m, 2H, aromatic H), 6.93 (t, J=8.8 Hz, 1H, aromatic H), 6.90-6.83 (m, 2H, aromatic H), 6.51 (dd, J=12.1, 2.7 Hz, 1H, aromatic H), 6.41 (ddd, J=8.6, 2.7, 1.2 Hz, 1H, aromatic H), 3.66 (s, 2H, NH$_2$), 2.52-2.45 (m, 1H, cyclohexyl H), 1.96-1.72 (m, 5H, cyclohexyl H), 1.53-1.18 (m, 5H, cyclohexyl H). $^{13}$C NMR (101 MHz, CDCl$_3$) δ 156.74, 156.55, 154.09, 144.39, 144.30, 142.04, 134.86, 134.74, 127.79, 123.89, 115.76, 110.93, 110.90, 103.90, 103.69, 43.80, 34.72, 26.99, 26.22.

3-fluoro-4-(4-(tert-pentyl)phenoxy)aniline, I3-K

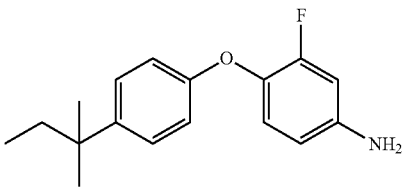

Following procedure B, I3-nK (497 mg, 1.64 mmol, 1.00 eq) was dissolved in MeOH (I3 mL) and added to a suspension of Pd (10%) on activated carbon powder (28 mg, 0.03 mmol Pd, 0.02 eq) in MeOH (2 mL). The flask was purged with H$_2$ (6×) and the reaction mixture was stirred at room temperature for 1.5 h. The crude product was purified by flash column chromatography (SiO$_2$; ethyl acetate/petrolether 1:10 to 1:7.5) to give the title compound as orange oil (463 mg, 1.69 mmol, quant. yield). R$_f$=0.28 (EtOAc/petrolether 1:5). HRMS (ESI) calcd. for C$_{17}$H$_{21}$FNO$^+$ [M+H]$^+$ 274.1602. found: 274.1599. $^1$H NMR (400 MHz, CDCl$_3$) δ 7.26-7.17 (m, 2H, aromatic H), 6.92 (t, J=8.8 Hz, 1H, aromatic H), 6.89-6.80 (m, 2H, aromatic H), 6.51 (dd, J=12.0, 2.7 Hz, 1H, aromatic H), 6.42 (ddd, J=8.7, 2.7, 1.2 Hz, 1H, aromatic H), 3.65 (s, 2H, NH$_2$), 1.61 (q, J=7.4 Hz, 2H, Ar—C(CH$_3$)$_2$CH$_2$CH$_3$), 1.26 (s, 6H, Ar—C(CH$_3$)$_2$CH$_2$CH$_3$), 0.69 (t, J=7.4 Hz, 3H, Ar—C(CH$_3$)$_2$CH$_2$CH$_3$). $^{13}$C NMR (101 MHz, CDCl$_3$) δ 156.61, 156.37, 154.15, 144.34, 144.25, 143.34, 134.98, 134.86, 123.95, 123.92, 115.41, 110.98, 110.95, 104.00, 103.78, 37.07, 28.68, 9.26.

6-(4-(2-methylpentan-2-yl)phenoxy)pyridin-3-amine, I3-L

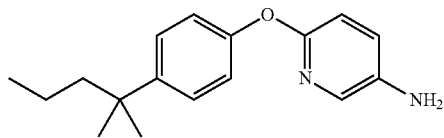

Following procedure B, I3-nL (50 mg, 0.17 mmol, 1.00 eq) was dissolved in MeOH (12 mL) and added to a suspension of Pd (10%) on activated carbon powder (31 mg, 0.03 mmol Pd, 0.17 eq) in MeOH (3 mL). The flask was purged with H$_2$ (6×) and the reaction mixture was stirred at room temperature for 1.5 h. The crude product was purified by flash column chromatography (SiO$_2$; DCM/MeOH 1%) to give the title compound as pale orange oil (39 mg, 0.14 mmol, 87% yield). R$_f$=0.41 (DCM/MeOH 4%). HRMS (ESI) calcd. for C$_{17}$H$_{23}$N$_2$O$^+$ [M+H]$^+$ 271.1805. found: 271.1796. $^1$H NMR (400 MHz, CDCl$_3$) δ 7.73 (d, J=2.9 Hz, 1H, aromatic H), 7.32-7.26 (m, 2H, aromatic H), 7.07 (dd, J=8.6, 3.0 Hz, 1H, aromatic H), 7.01-6.94 (m, 2H, aromatic H), 6.74 (d, J=8.6 Hz, 1H, aromatic H), 3.35 (s, 2H, NH$_2$), 1.61-1.51 (m, 2H, C(CH$_3$)$_2$CH$_2$CH$_2$CH$_3$), 1.27 (s, 6H, C(CH$_3$)$_2$CH$_2$CH$_2$CH$_3$), 1.16-1.01 (m, 2H, C(CH$_3$)$_2$CH$_2$CH$_2$CH$_3$), 0.82 (t, J=7.3 Hz, 3H, C(CH$_3$)$_2$CH$_2$CH$_2$CH$_3$). $^{13}$C NMR (101 MHz, CDCl$_3$) δ 156.82, 153.32, 145.10, 138.67, 134.32, 128.12, 127.09, 126.99, 119.62, 119.13, 112.53, 47.31, 37.49, 29.17, 18.08, 14.90.

4-(4-((3r,5r,7r)-adamantan-1-yl)phenoxy)aniline, I3-M

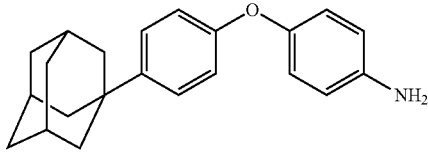

Following procedure B, I3-nM (615 mg, 1.76 mmol, 1.00 eq) was dissolved in toluene (15 mL) and added to a suspension of Pd (10%) on activated carbon powder (126 mg, 0.12 mmol Pd, 0.07 eq) in MeOH (10 mL). The flask was purged with H$_2$ (6×) and the reaction mixture was stirred at room temperature for 19 h. The crude product was purified by flash column chromatography (SiO$_2$; DCM) to give the title compound as beige solid (538 mg, 1.68 mmol, 96% yield). R$_f$=0.39 (DCM/MeOH 1%). HRMS (ESI) calcd. for C$_{22}$H$_{26}$NO$^+$[M+H]$^+$ 320.2009. found: 320.2006. $^1$H NMR (400 MHz, CDCl$_3$) δ 7.32-7.25 (m, 2H, aromatic H), 6.93-6.86 (m, 4H, aromatic H), 6.72-6.65 (m, 2H, aromatic H), 3.56 (s, 2H, NH$_2$), 2.14-2.06 (m, 3H, adamantyl H), 1.90 (d, J=2.9 Hz, 5H, adamantyl H), 1.84-1.71 (m, 5H, adamantyl H). $^{13}$C NMR (101 MHz, CDCl$_3$) δ 156.59, 149.02, 145.32, 142.51, 125.98, 121.10, 116.84, 116.34, 43.45, 36.88, 35.78, 29.07.

4-(4-((3r,5r,7r)-adamantan-1-yl)phenoxy)-3-fluoroaniline, I3-N

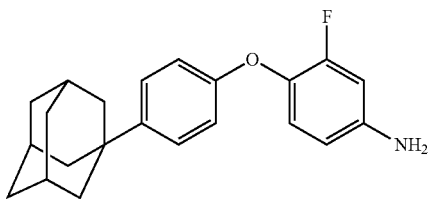 [SMILES: Nc1ccc(Oc2ccc(C34CC5CC(CC(C5)C3)C4)cc2)c(F)c1]

Following procedure B, I3-nN (570 mg, 1.55 mmol, 1.00 eq) was dissolved in toluene (10 mL) and added to a suspension of Pd (10%) on activated carbon powder (143 mg, 0.13 mmol Pd, 0.09 eq) in MeOH (10 mL). The flask was purged with H$_2$ (6×) and the reaction mixture was stirred at room temperature for 7 h. The crude product was purified by flash column chromatography (SiO$_2$; DCM) to give the title compound as colourless solid (510 mg, 1.51 mmol, 97% yield). R$_f$=0.67 (DCM/MeOH 1%). HRMS (ESI) calcd. for C$_{22}$H$_{25}$FNO$^+$ [M+H]$^+$ 338.1915. found: 338.1916. $^1$H NMR (400 MHz, CDCl$_3$) δ 7.32-7.23 (m, 2H, aromatic H), 6.92 (t, J=8.8 Hz, 1H, aromatic H), 6.89-6.81 (m, 2H, aromatic H), 6.51 (dd, J=12.0, 2.7 Hz, 1H, aromatic H), 6.41 (ddd, J=8.7, 2.7, 1.2 Hz, 1H, aromatic H), 3.64 (s, 2H, NH$_2$), 2.11-2.07 (m, 3H, adamantyl H), 1.89 (d, J=2.9 Hz, 5H, adamantyl H), 1.83-1.70 (m, 5H, adamantyl H). $^{13}$C NMR (101 MHz, CDCl$_3$) δ 156.60, 156.47, 154.15, 145.37, 144.33, 144.24, 134.91, 134.79, 125.98, 123.97, 123.95, 115.47, 110.98, 110.95, 103.98, 103.76, 43.43, 36.86, 35.76, 29.06.

6-(4-isopropylphenoxy)pyridin-3-amine, I3-O

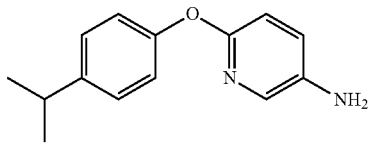

Following procedure B, I3-n0 (202 mg, 0.78 mmol, 1.00 eq) was added to a suspension of Pd (10%) on activated carbon powder (76 mg, 0.07 mmol Pd, 0.09 eq) in MeOH (15 mL). The flask was purged with H$_2$ (6×) and the reaction mixture was stirred at room temperature for 1 h. The crude product was purified by flash column chromatography (SiO$_2$; DCM/MeOH 1%) to give the title compound as beige solid (150 mg, 0.66 mmol, 84% yield). R$_f$=0.42 (DCM/MeOH 4%). FIRMS (ESI) calcd. for C$_{14}$H$_{17}$N$_2$O$^+$[M+H]$^+$ 229.1335. found: 229.1326. $^1$H NMR (400 MHz, CDCl$_3$) δ 7.70 (d, J=2.9 Hz, 1H, aromatic H), 7.24-7.14 (m, 2H, aromatic H), 7.05 (dd, J=8.6, 3.0 Hz, 1H, aromatic H), 7.01-6.93 (m, 2H, aromatic H), 6.73 (d, J=8.6 Hz, 1H, aromatic H), 3.33 (s, 2H, NH$_2$), 2.89 (hept, J=6.9 Hz, 1H, CH(CH$_3$)$_2$), 1.24 (d, J=7.0 Hz, 6H, CH(CH$_3$)$_2$). $^{13}$C NMR (101 MHz, CDCl$_3$) δ 156.88, 153.59, 144.19, 138.68, 134.19, 127.55, 126.97, 119.76, 112.35, 77.48, 77.16, 76.84, 33.57, 24.20.

6-(4-(2,4,4-trimethylpentan-2-yl)phenoxy)pyridin-3-amine, I3-P

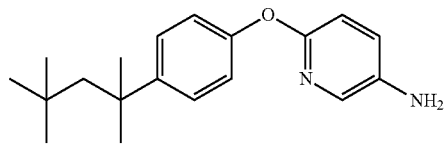

Following procedure B, I3-nP (283 mg, 0.86 mmol, 1.00 eq) was dissolved in toluene (4 mL) and added to a suspension of Pd (10%) on activated carbon powder (78 mg, 0.07 mmol Pd, 0.09 eq) in MeOH (15 mL). The flask was purged with H$_2$ (5×) and the reaction mixture was stirred at room temperature for 2 h. The crude product was purified by flash column chromatography (SiO$_2$; DCM/MeOH 2%) to give the title compound as colourless solid (235 mg, 0.79 mmol, 91% yield). R$_f$=0.49 (DCM/MeOH 4%). HRMS (ESI) calcd. for C$_{19}$H$_{27}$N$_2$O$^+$ [M+H]$^+$ 299.2118. found: 299.2112. $^1$H NMR (400 MHz, CDCl$_3$) δ 7.73 (dd, J=3.0, 0.7 Hz, 1H, aromatic H), 7.37-7.29 (m, 2H, aromatic H), 7.06 (dd, J=8.6, 3.0 Hz, 1H, aromatic H), 6.99-6.93 (m, 2H, aromatic H), 6.71 (dd, J=8.6, 0.7 Hz, 1H, aromatic H), 3.10 (s, 2H, NH$_2$), 1.72 (s, 2H, Ar—C(CH$_3$)$_2$CH$_2$C(CH$_3$)$_3$), 1.36 (s, 6H, Ar—C(CH$_3$)$_2$CH$_2$C(CH$_3$)$_3$), 0.73 (s, 9H, Ar—C(CH$_3$)$_2$CH$_2$C(CH$_3$)$_3$). $^{13}$C NMR (101 MHz, CDCl$_3$) δ 156.87, 153.39, 145.48, 138.70, 134.39, 127.37, 126.94, 118.96, 112.41, 57.20, 38.36, 32.50, 31.93, 31.68.

The invention claimed is:

1. A method for identifying modulators of NOTCH signalling in a cell culture, comprising
   (i) co-culturing mammalian cells expressing a NOTCH ligand and mammalian cells expressing a NOTCH receptor to form a co-culture, wherein said mammalian cells expressing a NOTCH ligand are HeLa cells that have been transfected with a NOTCH ligand expression system and said mammalian cells expressing a NOTCH receptor are HeLa cells that have been transfected with a NOTCH receptor expression system;
   (ii) incubating the co-culture with and without a candidate modulator of NOTCH signalling to be tested
   (iii) quantifying the amount of a NOTCH intracellular domain (NICD) that has been released from a NOTCH receptor; and/or
   (iv) quantifying the NICD-mediated modulation of a NOTCH signalling specific reporter system, wherein a reduction in the signal of the NOTCH signalling specific reporter system, a reduction of the amount of NICD, the absence of NICD and/or the absence of the signal of the NOTCH signalling specific reporter system in said co-culture that has been incubated with a candidate modulator of NOTCH signalling, compared to the signal of the NOTCH signalling specific reporter system and/or the amount of NICD in said co-culture that has been incubated without a candidate modulator of NOTCH signalling, is indicative of NOTCH signalling modulation.

2. The method according to claim 1, wherein the expressed NOTCH ligand is selected from the group consisting of Delta 1 (DL1), Delta 3 (DL3), Delta 4 (DL4), Jagged 1 and Jagged 2.

3. The method according to claim 2, wherein the expressed NOTCH ligand is DL4.

4. The method according to claim 1, wherein the expressed NOTCH receptor is selected from the group consisting of a NOTCH1 receptor, a NOTCH2 receptor, a NOTCH3 receptor and a NOTCH4 receptor.

5. The method according to claim 4, wherein the expressed NOTCH receptor is a NOTCH1 receptor or a NOTCH2 receptor.

6. The method according to claim 1, wherein the NICD is released from the NOTCH receptor which is expressed by said mammalian cells expressing a NOTCH receptor.

7. The method according to claim 1, wherein the mammalian cells expressing a NOTCH ligand and the mammalian cells expressing a NOTCH receptor are co-cultured in a ratio of 1:5 to 5:1.

8. The method according to claim 1, wherein the mammalian cells expressing a NOTCH ligand and the mammalian cells expressing a NOTCH receptor are co-cultured in a ratio of 1:1.

9. The method according to claim 1, wherein the mammalian cells expressing a NOTCH ligand and the mammalian cells expressing a NOTCH receptor have about 100% confluency prior to incubation with and without a candidate modulator of NOTCH signalling to be tested.

10. The method according to claim 1, wherein said mammalian cells that have been transfected with a NOTCH ligand expression system have been stably transfected with a NOTCH ligand expression system; and/or
    wherein said mammalian cells that have been transfected with a NOTCH receptor expression system have been stably transfected with a NOTCH receptor expression system.

11. The method according to claim 1, wherein said mammalian cells that have been transfected with a NOTCH ligand expression system have been transiently transfected with a NOTCH ligand expression system; and/or
    wherein said mammalian cells that have been transfected with a NOTCH receptor expression system have been transiently transfected with a NOTCH receptor expression system.

12. The method according to claim 1, wherein said mammalian cells expressing a NOTCH receptor have been transfected with at least one plasmid encoding a NOTCH signalling specific reporter system.

13. The method according to claim 12, wherein the NOTCH signalling specific reporter system comprises a C promoter binding factor 1 (CBF1), suppressor of hairless, Lag1 (CSL) transcription factor binding site in the promoter region and a reporter protein.

14. The method according to claim 13, wherein the reporter protein is selected from the group consisting of a reporter luciferase, a reporter beta-galactosidase and a reporter fluorescent protein.

15. The method according to claim 14, wherein said reporter fluorescent protein is selected from the group consisting of GFP, eGFP, tomato, cherry, dsRED, Venus and Cyan.

16. The method according to claim 13, wherein the reporter protein is a luciferase.

17. The method according to claim 13, wherein the reporter protein is a firefly (*Photinus pyralis*) luciferase.

18. The method according to claim 12, wherein said mammalian cells expressing a NOTCH receptor have been further transfected with at least one plasmid encoding a further reporter system.

19. The method according to claim 18, wherein said further reporter system comprises a *Renilla* (*Renilla reniformis*) luciferase.

20. The method according to claim 1, wherein said NOTCH ligand expression system is a lentivirus containing a NOTCH ligand cDNA and/or wherein said NOTCH receptor expression system is a lentivirus containing a plasmid comprising mouse NOTCH receptor cDNA.

21. The method according to claim 1, wherein the cells of said cell culture are lysed prior to
    quantifying the amount of a NOTCH intracellular domain (NICD) that has been released from a NOTCH receptor; and/or
    quantifying the NICD-mediated modulation of a NOTCH signalling specific reporter system.

22. The method according to claim 1, wherein the amount of NICD in (iii) is quantified using Western blotting.

23. A method for identifying modulators of NOTCH signalling by high throughput screening of a library comprising candidate modulators of NOTCH signalling comprising the steps of:
    (a) providing an assay in wells of a microwell plate wherein the assay comprises a co-culture comprising mammalian cells expressing a NOTCH ligand and mammalian cells expressing a NOTCH receptor, wherein said mammalian cells expressing a NOTCH ligand are HeLa cells that have been transfected with a NOTCH ligand expression system and said mammalian cells expressing a NOTCH receptor are HeLa cells that have been transfected with a NOTCH receptor expression system;
    (b) incubating the co-culture of said assay with and without a candidate modulator of NOTCH signalling to be tested; and (c)(i) quantifying the amount of a NOTCH intracellular domain (NICD) that has been released from the NOTCH receptor; and/or
(c)(ii) quantifying the NICD-mediated modulation of a NOTCH signalling specific reporter system;
wherein a reduction in the signal of the NOTCH signalling specific reporter system, a reduction of the amount of NICD, the absence of NICD and/or the absence of the signal of the NOTCH signalling specific reporter system in said co-culture that has been incubated with a candidate modulator of NOTCH signalling, compared to the signal of the NOTCH signalling specific reporter system and/or the amount of NICD in said co-culture that has been incubated without a candidate modulator of NOTCH signalling, is indicative of NOTCH signalling modulation.

24. The method according to claim 23, wherein incubation in step (b) lasts from 30 min to 48 h.

25. The method according to claim 23, wherein incubation in step (b) lasts at least 12 hours.

* * * * *